US008093140B2

(12) United States Patent
Chen et al.

(10) Patent No.: US 8,093,140 B2
(45) Date of Patent: *Jan. 10, 2012

(54) AMORPHOUS GE/TE DEPOSITION PROCESS

(75) Inventors: Philip S. H. Chen, Bethel, CT (US); William Hunks, Waterbury, CT (US); Tianniu Chen, Rocky Hill, CT (US); Matthias Stender, New Milford, CT (US); Chongying Xu, New Milford, CT (US); Jeffrey F. Roeder, Brookfield, CT (US); Weimin Li, New Milford, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 671 days.

This patent is subject to a terminal disclaimer.

(21) Appl. No.: 12/263,403

(22) Filed: Oct. 31, 2008

(65) Prior Publication Data

US 2009/0112009 A1    Apr. 30, 2009

Related U.S. Application Data

(60) Provisional application No. 60/984,370, filed on Oct. 31, 2007, provisional application No. 61/050,179, filed on May 2, 2008, provisional application No. 61/051,274, filed on May 7, 2008, provisional application No. 61/052,018, filed on May 9, 2008, provisional application No. 61/076,428, filed on Jun. 27, 2008.

(51) Int. Cl.
*H01L 21/00* (2006.01)
*B32B 15/04* (2006.01)
*C07F 7/00* (2006.01)

(52) U.S. Cl. ............... 438/482; 428/457; 257/E21.662; 556/35; 556/81

(58) Field of Classification Search .............. 556/35, 556/81; 428/457, 482; 257/E21.662; 438/438
See application file for complete search history.

(56) References Cited

U.S. PATENT DOCUMENTS

| | | | |
|---|---|---|---|
| 4,927,670 A | 5/1990 | Erbil | |
| 4,948,623 A | 8/1990 | Beach et al. | |
| 4,960,916 A | 10/1990 | Pazik | |
| 4,962,214 A | 10/1990 | Villacorta et al. | |
| 5,296,716 A | 3/1994 | Ovshinsky et al. | |
| 5,453,494 A | 9/1995 | Kirlin et al. | |
| 5,596,522 A | 1/1997 | Ovshinsky et al. | |
| 6,005,127 A | 12/1999 | Todd et al. | |
| 6,086,779 A | 7/2000 | Bishop et al. | |
| 6,123,993 A | 9/2000 | Xu et al. | |
| 6,146,608 A | 11/2000 | Todd et al. | |
| 6,269,979 B1 | 8/2001 | Dumont | |
| 6,331,211 B1 | 12/2001 | Xu et al. | |
| 6,511,718 B1 | 1/2003 | Paz de Araujo et al. | |
| 6,646,122 B1 | 11/2003 | Nuhlen et al. | |
| 6,787,186 B1 | 9/2004 | Hintermaier | |
| 6,861,559 B2 | 3/2005 | Odom | |
| 6,869,638 B2 | 3/2005 | Baum et al. | |
| 6,872,963 B2 | 3/2005 | Kostylev et al. | |
| 6,984,591 B1 | 1/2006 | Buchanan et al. | |
| 6,998,289 B2 | 2/2006 | Hudgens et al. | |
| 7,029,978 B2 | 4/2006 | Dodge | |
| 7,087,482 B2 | 8/2006 | Yeo et al. | |
| 7,115,927 B2 | 10/2006 | Hideki et al. | |
| 7,173,271 B2 | 2/2007 | Chang | |
| 7,312,165 B2 | 12/2007 | Jursich et al. | |
| 7,371,429 B2 | 5/2008 | Lee et al. | |
| 7,399,666 B2 | 7/2008 | Ahn et al. | |
| 7,402,851 B2 | 7/2008 | Hideki et al. | |
| 7,419,698 B2 | 9/2008 | Jones | |
| 7,425,735 B2 | 9/2008 | Park et al. | |
| 7,462,900 B2 | 12/2008 | Hideki et al. | |
| 7,476,917 B2 | 1/2009 | Hideki et al. | |
| 7,518,007 B2 | 4/2009 | Seo et al. | |
| 7,569,417 B2 | 8/2009 | Lee et al. | |
| 7,615,401 B2 | 11/2009 | Park et al. | |
| 7,638,787 B2 | 12/2009 | An et al. | |
| 7,666,789 B2 | 2/2010 | Choi et al. | |
| 7,667,218 B2 | 2/2010 | Yamamoto et al. | |
| 7,704,787 B2 | 4/2010 | Hideki et al. | |
| 7,727,884 B2 | 6/2010 | Bae et al. | |
| 7,728,172 B2 | 6/2010 | Lee et al. | |
| 7,737,290 B2 | 6/2010 | Gordon et al. | |
| 7,803,657 B2 | 9/2010 | Choi et al. | |
| 7,838,329 B2* | 11/2010 | Hunks et al. ............ | 438/102 |
| 7,858,152 B2 | 12/2010 | Ovshinsky et al. | |
| 7,902,048 B2 | 3/2011 | Shin et al. | |

(Continued)

FOREIGN PATENT DOCUMENTS

DE     102008026889 A1     2/2009

(Continued)

OTHER PUBLICATIONS

Abrutis, A., et al., "Hot-Wire Chemical Vapor Deposition of Chalcogenide Materials for Phase Change Memory Applications", "Chem. Mater.", 2008, pp. 3557-3559, vol. 20.

Milanov, A.P., et al., "Bis(2-butyl-N, N-diisopropylamidinato) dichlorohafnium (IV)", "Crystal Structure Communications", 2005, pp. 370-372, vol. 61, No. 7.

Gupta, A. et al., "Triorganoantimony(V) complexes with internally functionallized oximes: synthetic, spectroscopic and structural aspects..", "Journal of Organometallic Chemistry", 2002, pp. 118-126, vol. 645.

Raj, P. et al., "Triorganoantimony(V) complexes with internally functionallized oximes: synthetic, spectroscopic and structural aspects..", "Journal of Organometallic Chemistry", 1992, pp. 118-126, vol. 645 (Only Abstract Provided).

(Continued)

*Primary Examiner* — Porfirio Nazario Gonzalez
(74) *Attorney, Agent, or Firm* — Steven J. Hultqiuist; Hultquist IP; Maggie Chappuis

(57) ABSTRACT

Germanium, tellurium, and/or antimony precursors are usefully employed to form germanium-, tellurium- and/or antimony-containing films, such as films of GeTe, GST, and thermoelectric germanium-containing films. Processes for using these precursors to form amorphous films are also described. Further described is the use of [{nBuC(iPrN)$_2$}$_2$Ge] or Ge butyl amidinate to form GeTe smooth amorphous films for phase change memory applications.

20 Claims, 12 Drawing Sheets

U.S. PATENT DOCUMENTS

| | | | |
|---|---|---|---|
| 7,935,564 | B2 | 5/2011 | Breitwisch et al. |
| 7,960,205 | B2 | 6/2011 | Xiao et al. |
| 2002/0004266 | A1 | 1/2002 | Hashimoto et al. |
| 2002/0090815 | A1 | 7/2002 | Koike et al. |
| 2003/0135061 | A1 | 7/2003 | Norman et al. |
| 2004/0038808 | A1 | 2/2004 | Hampden-Smith et al. |
| 2004/0197945 | A1 | 10/2004 | Woelk et al. |
| 2004/0215030 | A1 | 10/2004 | Norman |
| 2005/0002227 | A1 | 1/2005 | Hideki et al. |
| 2005/0082624 | A1 | 4/2005 | Gousev et al. |
| 2005/0208699 | A1 | 9/2005 | Furkay et al. |
| 2005/0283012 | A1 | 12/2005 | Xu et al. |
| 2005/0287747 | A1 | 12/2005 | Chakravarti et al. |
| 2006/0006449 | A1 | 1/2006 | Jeong et al. |
| 2006/0027451 | A1 | 2/2006 | Park et al. |
| 2006/0035462 | A1 | 2/2006 | Millward |
| 2006/0049447 | A1 | 3/2006 | Lee et al. |
| 2006/0115595 | A1 | 6/2006 | Shenai-Khatkhate et al. |
| 2006/0138393 | A1 | 6/2006 | Seo et al. |
| 2006/0141155 | A1 | 6/2006 | Gordon et al. |
| 2006/0172067 | A1 | 8/2006 | Ovshinsky et al. |
| 2006/0172083 | A1 | 8/2006 | Lee et al. |
| 2006/0180811 | A1 | 8/2006 | Lee et al. |
| 2007/0121363 | A1 | 5/2007 | Lung |
| 2007/0154637 | A1 | 7/2007 | Shenai-Khatkhate et al. |
| 2007/0160760 | A1 | 7/2007 | Shin et al. |
| 2008/0003359 | A1 | 1/2008 | Gordon et al. |
| 2008/0054244 | A1 | 3/2008 | Lee et al. |
| 2008/0118636 | A1 | 5/2008 | Shin et al. |
| 2008/0145702 | A1 | 6/2008 | Shin et al. |
| 2008/0210924 | A1 | 9/2008 | Shin |
| 2008/0254218 | A1 | 10/2008 | Lei et al. |
| 2008/0254232 | A1 | 10/2008 | Gordon et al. |
| 2008/0272355 | A1 | 11/2008 | Cho et al. |
| 2008/0286446 | A1 | 11/2008 | Kamepalli et al. |
| 2009/0050869 | A1 | 2/2009 | Kim et al. |
| 2009/0074652 | A1 | 3/2009 | Dussarrat |
| 2009/0097305 | A1 | 4/2009 | Bae et al. |
| 2009/0124039 | A1 | 5/2009 | Roeder et al. |
| 2009/0142881 | A1 | 6/2009 | Xiao et al. |
| 2009/0162973 | A1 | 6/2009 | Gatineau et al. |
| 2009/0191330 | A1 | 7/2009 | Xiao |
| 2009/0215225 | A1 | 8/2009 | Stender et al. |
| 2009/0275164 | A1 | 11/2009 | Chen et al. |
| 2009/0280052 | A1 | 11/2009 | Xiao et al. |
| 2009/0299084 | A1 | 12/2009 | Okubo et al. |
| 2009/0305458 | A1 | 12/2009 | Hunks et al. |
| 2009/0321733 | A1 | 12/2009 | Gatineau et al. |
| 2010/0055831 | A1 | 3/2010 | An et al. |
| 2010/0159637 | A1 | 6/2010 | Lee et al. |
| 2010/0317150 | A1 | 12/2010 | Hunks et al. |
| 2010/0320434 | A1 | 12/2010 | Choi et al. |
| 2011/0124182 | A1 | 5/2011 | Zheng |

FOREIGN PATENT DOCUMENTS

| | | | |
|---|---|---|---|
| EP | 1675194 | A2 | 6/2006 |
| EP | 1995236 | A1 | 11/2008 |
| EP | 2067876 | A2 | 6/2009 |
| EP | 2130942 | A2 | 12/2009 |
| JP | 58038296 | A | 3/1983 |
| JP | 2001-067720 | A | 3/2001 |
| JP | 2008-131046 | A | 6/2008 |
| JP | 2009-149980 | A | 7/2009 |
| KR | 20050084997 | A | 8/2005 |
| KR | 10-2006-0091160 | A | 8/2006 |
| KR | 10-2008-0052362 | A | 6/2008 |
| KR | 10-2009-0054925 | A | 6/2009 |
| SU | 768457 | A | 10/1980 |
| WO | 2004046417 | A2 | 6/2004 |
| WO | 2006012052 | A2 | 2/2006 |
| WO | 2007067604 | A2 | 6/2007 |
| WO | 2007140813 | A1 | 12/2007 |
| WO | 2008002546 | A1 | 1/2008 |
| WO | 2008057616 | A2 | 5/2008 |
| WO | 2009039187 | A1 | 3/2009 |
| WO | 2009134989 | A2 | 11/2009 |
| WO | 2010055423 | A2 | 5/2010 |

OTHER PUBLICATIONS

Raj, P. et al., "Synthesis and geometry of complex triorganoantimony (V) cations", "Journal of Organometallic Chemistry", 1992, pp. 1471-1494, vol. 22, No. 10 (Only Abstract Provided).

Anderson, Q. et al., "Synthesis and Characterization of the First Pentaphenylcyclopentadienyl Copper Complex (Ph5CP)Cu(PPh3)", "Organometallics", 1998, pp. 4917-4920, vol. 17.

Artaud-Gillet, M.C. et al., "Evaluation of copper organometallic sources for CuGaSe2 photovoltaic applications", "Journal of Crystal Growth", 2003, pp. 163-168, vol. 248.

Macomber, D. et al., "n5—Cyclopentadienyl- and n5-Pentamethylcyclopentadienyl copper compunds Containng Phosphine, Carbonyl, and n2-Acetyle", "J. Am. Chem.", 1983, pp. 5325-5329, vol. 105.

Ren, H. et al., "Sythesis and structures of cyclopentadienyl N-heterocyclic carbene copper complexes", "Journal of Organometallic Chemistry", 2006, pp. 4109-4113, vol. 691.

Lee, J. et al., "GeSbTe deposition for the PRAM application", "Applied Surface Science", 2007, pp. 3969-3976, vol. 253, Publisher.

Herrmann, W. et al., "Stable Cyclic Germanediyls ('Cyclogermylenes'): Synthesis, Structure, Metal Complexes, and Thermolyses,", "Angew. Chem. Int. Ed. Engl.", 1992, pp. 1485-1488, vol. 31, No. 11.

Kim, R., et al., "Structural Properties of Ge2Sb2Te5 thin films by metal organic chemical vapor deposition for phase change memory . . . ", "Applied Physics Letters", 2006, vol. 89, No. 102107.

Meller, A., et al., "Synthesis and Isolation of New Germanium (II) Compounds and of Free Germylenes", 1984, pp. 2020-2029, vol. 118 (English Abstract).

Anderson, Herbert H., "Dialkylaminogermanes and Dialkylaminosilanes", "J. Amer. Chem. Soc.", Mar. 20, 1952, pp. 1421-1423, vol. 74, No. 6.

Kim, S. et al., "Electrical Properties and Crystal Structures of Nitrogen Doped Ge2Sb2Te5 Thin Film for Phase Change Memory", "Thin Solid Films", Oct. 30, 2004, pp. 322-326, vol. 469-470.

Oakley, Sarah H., et al., "Structural consequences of the prohibition of hydrogen bonding in copper-guanidine systems", "Inorg. Chem.", 2004, pp. 5168-5172, vol. 43, No. 16.

Shi, Y. et al., "Titanium dipyrrolylmethane derivatives: rapid intermolecular alkyne hydroamination", "Chemical Commun.", Feb. 4, 2003, pp. 586-587, Publisher: Royal Society of Chemistry.

Co-pending Unpublished U.S. Appl. No. 12/392,009, filed Feb. 24, 2009.

Chorley, R. et al., "Subvalent Group 14 metal compounds. The X-ray crystal structures of two monomeric Group 14 metal bisamides, Ge[N(SiMe,).", "Inorganica Chemica Acta", 1992, pp. 203-209, Publisher: Elsevier.

Foley, S. et al., "Facile Formation of Rare Terminal Chalcogenido Germanium Complexes with Alkyllamidinates as Supporting Ligands", "J. Am. Chem", 1997, pp. 10359-10363, vol. 119.

Karsch, H. et al., "Bis(amidinate) Complexes of Silicon and Germanium", "Eur. J. Inorg. Chemistry", 1998, pp. 433-436.

Lappert, M. et al., "monomeric, coloured germanium (II) and tin (II) di-t-butylamides, and the crystal and molecular structure of Ge (NCMe2.).", "J.C.S. Chem. Comm.", 1980, pp. 621-622.

Lee, S. et al., "GeSbTe deposition for the PRAM application", "Applied Surface Science", , pp. 3969-3976, vol. 253, Publisher: Elsevier, (2007).

Mathur, S. et al., "Germanium Nanowires and Core-Shell Nanostructures by Chemical Vapor Deposition of [Ge (C5H5)2]", "Chem. Mater.", May 15, 2004, pp. 2449-2456, vol. 16.

Stauf, G. et al., "Low Temperature ALD of Germanium for Phase Change Memory Thin Films", "AVS 7th International Conference on Atomic Layer Deposition", Jun. 24, 2007, pp. 18, Publisher: ALD 2007, San Diego.

Veprek, S. et al., "Organometallic chemical vapor deposition of germanium from a cyclic germylene, 1,3-Di-tert-butyl-1,3,2-diazagermolidin..", "Chem. Mater.", 1996, pp. 825-831, vol. 8, Publisher: American Chemical Society.

* cited by examiner

AMORPHOUS GE/TE DEPOSITION PROCESS

CROSS-REFERENCE TO RELATED APPLICATIONS

The benefit of priority of U.S. Provisional Patent Application 61/051,274 filed May 7, 2008, U.S. Provisional Patent Application 61/052,018 filed May 9, 2008, U.S. Provisional Patent Application 61/076,428 filed Jun. 27, 2008, U.S. Provisional Patent Application 60/984,370 filed Oct. 31, 2007 and U.S. Provisional Patent Application 61/050,179 filed May 2, 2008 is hereby claimed under the provisions of 35 USC 119. The disclosures of said U.S. Provisional Patent Application 61/051,274, U.S. Provisional Patent Application 61/052,018, U.S. Provisional Patent Application 61/076,428, U.S. Provisional Patent Application 60/984,370 and U.S. Provisional Patent Application 61/050,179 are hereby incorporated herein by reference, in their respective entireties, for all purposes.

FIELD OF THE INVENTION

The present invention relates to a chemical vapor deposition process for forming amorphous films including germanium, tellurium and/or antimony on substrates, including, for example, germanium telluride (GeTe) and germanium antimony telluride (GST) films, as well as phase change random access memory devices and other devices incorporating such films. In particular, the present invention relates to amorphous GeTe and GST films formed from CVD processes, and devices formed from these films.

DESCRIPTION OF THE RELATED ART

Phase change random access memory (PCRAM) has attracted a great deal of interest recently for highly integrated non-volatile memory devices. In PCRAM cells, the high level of reset current that is required for switching the GST material from the crystalline to the amorphous state has been the major obstacle to the further scaling of PCRAM. Confining an alloy of germanium, antimony, and tellurium (GST) material into the contact plug, which greatly reduces the heat dissipation to the surrounding material, profoundly reduces the reset current. Therefore, it is necessary to deposit the GST film using a process that offers good conformality, such as atomic layer deposition (ALD) or chemical vapor deposition (CVD) processes. The ALD process is very time consuming, as it builds up the film "layer by layer". On the contrary, the CVD process offers a high deposition rate. Unfortunately, the CVD process tends to yield crystalline GeTe. The crystalline GeTe significantly reduces the conformality of the GST film, and often creates voids in the contact plug.

It would be advantageous to provide new processes for forming GST, GeTe, and other films in an amorphous manner, but with a relatively high deposition rate. The present invention provides such processes.

SUMMARY OF THE INVENTION

Improved chemical vapor deposition processes for forming amorphous GeTe and GST films on substrates, for applications such as PCRAM highly integrated non-volatile memory devices, are disclosed. The germanium and tellurium precursors described herein can be reacted in a reducing environment with ammonia, or, in some embodiments, in a nitrogen atmosphere, at a controlled temperature and pressure, to yield amorphous GeTe.

In one embodiment, the temperature of the deposition is 320° C. or less, and the pressure is 8 torr or less. In another embodiment, the temperature is 350° C. or less, and the pressure is 0.8 torr or less. Deposition of Ge from the germanium precursors (such as GeM or Ge amidinate) is fast at low temperatures. However, Te incorporation may result in the formation of crystalline GeTe. By controlling both the temperature and pressure, an amorphous GeTe film can be attained. This amorphous GeTe film remains relatively smooth after crystallization. This process can also be extended to other dialkyl Te precursors, such as di-isopropyl Te.

In another aspect, the present invention relates to a process for depositing an amorphous GeTe material on a substrate by chemical vapor deposition from a precursor which is vaporized to form a precursor vapor which is then contacted with the substrate. Representative precursors for depositing the amorphous GeTe films include Ge butylamidinate, (Ge-BAMDN) and [{nBuC(iPrN)$_2$}$_2$Ge], also referred to herein as GeM.

In one specific aspect of the invention, Ge butyl amidinate or GeM ({nBuC(iPrN)2}2Ge) can be employed with t-butyl Te, to yield amorphous GeTe, e.g., at a temperature of 320° C. and a pressure of 8 torr, or at a temperature of 350° C. and pressure of 0.8 torr when ammonia is utilized as a co-reactant.

In another aspect of the invention, a process for crystallizing an amorphous GeTe film to yield a relatively smooth GeTe film is described.

In a further aspect, the invention relates to a method of forming a GeTe, GST, antimony, or other such film on a substrate, involving volatilizing a germanium, antimony, or tellurium precursor described herein to form a precursor vapor, and contacting such precursor vapor with a substrate to form the germanium-, antimony-, and/or tellurium-containing film thereon.

In another aspect, the invention relates to a precursor composition for forming a germanium-containing film, comprising [{nBuC(iPrN)$_2$}$_2$Ge], also referred to herein as GeM.

Another aspect of the invention relates to a smooth amorphous germanium telluride or germanium-antimony-telluride film.

A further aspect of the invention relates to a method of forming a smooth amorphous germanium telluride film, comprising volatilizing [{nBuC(iPrN)$_2$}$_2$Ge] and a diakyl tellurium precursor to form a precursor vapor and contacting the precursor vapor with a substrate to form the smooth amorphous germanium telluride film on the substrate.

In another aspect, the invention relates to a method of forming a phase change random access memory device, comprising forming a germanium telluride film of amorphous character, comprising chemical vapor deposition of germanium from a germanium precursor comprising [{nBuC(iPrN)$_2$}$_2$Ge] or Ge butylamidinate.

The invention in another aspect relates to a method of making a PCRAM device, comprising forming a GeTe or GST film on a substrate for fabrication of said device, wherein said forming comprises depositing a film layer on the substrate from the vapor of a precursor described herein, using the processes for depositing amorphous germanium, tellurium, and or antimony layers described herein.

The precursors can be used to form a GST film on a substrate, by depositing one or more of the antimony-containing precursors described herein along with one or more germanium and tellurium-containing precursors on the substrate from a vapor comprising the precursors.

The precursors can also be used to form PCRAM devices, by forming a GST film on a substrate for fabrication of said device as described above.

In yet another aspect, the invention relates to a method of combating pre-reaction of the precursors described herein in a vapor deposition process for forming a film on a substrate, wherein the precursor is susceptible to pre-reaction adversely affecting the film, said method comprising introducing to said process a pre-reaction-combating agent selected from the group consisting of (i) heteroatom (O, N, S) organo Lewis base compounds, (ii) free radical inhibitors, and (iii) deuterium-containing reagents.

Another aspect of the invention relates to a method of combating pre-reaction of the precursors described herein in a vapor deposition process in which multiple feed streams are flowed to a deposition locus to form a film on a substrate, wherein at least one of said multiple feed streams includes a precursor susceptible to pre-reaction adversely affecting the film, said method comprising introducing to at least one of said multiple feed streams or supplied materials therefor, or to the deposition locus, a pre-reaction-combating agent selected from the group consisting of (i) heteroatom (O, N, S) organo Lewis base compounds, (ii) free radical inhibitors, and (iii) deuterium-containing reagents.

A still further aspect of the invention relates to a composition, comprising a precursor and a pre-reaction-combating agent for said precursor, said pre-reaction-combating agent being selected from the group consisting of (i) heteroatom (O, N, S) organo Lewis base compounds, (ii) free radical inhibitors, and (iii) deuterium-containing reagents.

In a further aspect, the invention relates to a method of combating pre-reaction of a vapor phase precursor as described herein in contact with a substrate for deposition of a film component thereon, comprising contacting said substrate, prior to said contact of the vapor phase precursor therewith, with a pre-reaction-combating agent selected from the group consisting of (i) heteroatom (O, N, S) organo Lewis base compounds, (ii) free radical inhibitors, and (iii) deuterium-containing reagents.

In a further aspect, the invention relates to a process wherein the pre-reaction combating reagent is introduced to passivate the surface of a growing film or slow the deposition rate, followed by reactivation using an alternative precursor or co-reactant (for example $H_2$, $NH_3$, plasma, $H_2O$, hydrogen sulfide, hydrogen selenide, diorganotellurides, diorganosulfides, diorganoselenides, etc.). Such passivation/retardation followed by reactivation thus may be carried out in an alternating repetitive sequence, for as many repetitive cycles as desired, in ALD or ALD-like processes. Prereaction-combating agents can be selected from the group consisting of (i) heteroatom (O, N, S) organo Lewis base compounds, (ii) free radical inhibitors, and (iii) deuterium-containing reagents.

Another aspect of the invention relates to a vapor phase deposition process for forming a film on a substrate involving cyclic contacting of the substrate with at least one film precursor described herein that is undesirably pre-reactive in the vapor phase, such process comprising introducing to said film during growth thereof a pre-reaction-combating reagent that is effective to passivate a surface of said film or to slow rate of deposition of said film, and after introducing said pre-reaction-combating reagent, reactivating said film with a different film precursor.

The invention relates in a further aspect to a method of forming a germanium-containing film on a substrate by a vapor deposition process, comprising volatilizing a germanium precursor to form a germanium precursor vapor, optionally combining the precursor vapor with a component selected from the group consisting of ammonia, hydrogen, helium, argon, and nitrogen, and contacting the precursor vapor with a substrate for vapor deposition of the germanium-containing film thereon, wherein the germanium precursor is selected from the group consisting of the following germanium compositions:

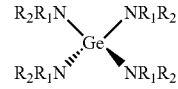

I wherein:
$R_1$ and $R_2$ may be the same as or different from one another, and are independently selected from H, $C_1$-$C_6$ alkyl, $C_2$-$C_5$ alkenyl, $C_5$-$C_{10}$ cycloalkyl, $C_6$-$C_{10}$ aryl, and —$Si(R_3)_3$ wherein each $R_3$ is independently selected from $C_1$-$C_6$ alkyl;

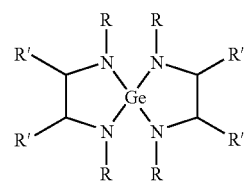

II wherein:
R and R' may be the same as or different from one another, and each R and R' is independently selected from H, $C_1$-$C_6$ alkyl, $C_2$-$C_5$ alkenyl, $C_5$-$C_{10}$ cycloalkyl, $C_6$-$C_{10}$ aryl, and —$Si(R_3)_3$ wherein each $R_3$ is independently selected from $C_1$-$C_6$ alkyl;

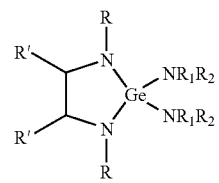

III wherein:
R, R', $R_1$ and $R_2$ may be the same as or different from one another, and each is independently selected from H, $C_1$-$C_6$ alkyl, $C_2$-$C_5$ alkenyl, $C_5$-$C_{10}$ cycloalkyl, $C_6$-$C_{10}$ aryl, and —$Si(R_3)_3$ wherein each $R_3$ is independently selected from $C_1$-$C_6$ alkyl;

$$(R)_{4-n}Ge(NR_1R_2)_n \quad\quad IV$$

wherein:
R, $R_1$, and $R_2$ may be the same as or different from one another, and each is independently selected from H, $C_1$-$C_6$ alkyl, $C_2$-$C_5$ alkenyl, $C_5$-$C_{10}$ cycloalkyl, $C_6$-$C_{10}$ aryl, and —$Si(R_3)_3$ wherein each $R_3$ is independently selected from $C_1$-$C_6$ alkyl; and
n is an integer from 0 to 4 inclusive;

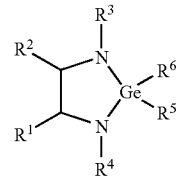

V wherein:
R¹, R², R³, R⁴, R⁵ and R⁶ may be the same as or different from one another, and each is independently selected from H, $C_1$-$C_6$ alkyl, $C_2$-$C_5$ alkenyl, $C_5$-$C_{10}$ cycloalkyl, $C_6$-$C_{10}$ aryl, and —Si(R₃)₃ wherein each $R_3$ is independently selected from $C_1$-$C_6$ alkyl;

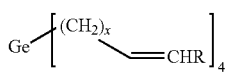

VI wherein:
R is selected from H, $C_1$-$C_6$ alkyl, and $C_6$-$C_{10}$ aryl; and x is 0, 1 or 2;

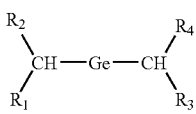

VII wherein:
R₁, R₂, R₃ and R₄ may be the same as or different from the others, and each is independently selected from among H, $C_1$-$C_6$ alkyl, $C_5$-$C_{10}$ cycloalkyl, $C_6$-$C_{10}$ aryl, and —Si(R₃)₃ wherein each $R_3$ is independently selected from $C_1$-$C_6$ alkyl;

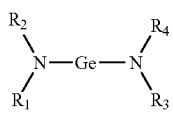

VIII wherein:
R₁, R₂, R₃, R₄, and R₅ may be the same as or different from one another, and each is independently selected from among H, $C_1$-$C_6$ alkyl, silyl, —Si(R')₃, $C_6$-$C_{10}$ cycloalkyl, $C_6$-$C_{10}$ aryl, —(CH₂)ₓNR'R", and —(CH₂)ₓOR'", wherein x=1, 2 or 3, and R', R" and R'" may be the same as or different from one another, and each is independently selected from $C_1$-$C_6$ alkyl;

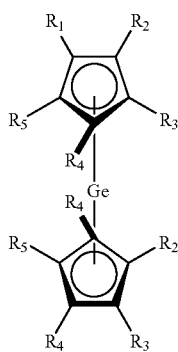

IX wherein:
R' and R" may be the same as or different from one another, and are independently selected from among H, $C_1$-$C_6$ alkyl, $C_5$-$C_{10}$ cycloalkyl, $C_6$-$C_{10}$ aryl, and —Si(R³)₃ wherein each R³ is independently selected from $C_1$-$C_6$ alkyl; and each X is independently selected from among $C_1$-$C_6$ alkyl, $C_1$-$C_6$ alkoxy, —NR¹R², and —C(R³)₃, wherein each of R¹, R² and R³ is independently selected from H, $C_1$-$C_6$ alkyl, $C_5$-$C_{10}$ cycloalkyl, $C_6$-$C_{10}$ aryl, and —Si(R⁴)₃ wherein each R⁴ is independently selected from $C_1$-$C_6$ alkyl;

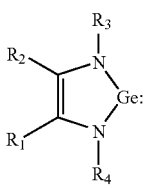

X wherein:
R₁, R₂, R₃ and R₄ may be same as or different from one another, and are independently selected from among H, $C_1$-$C_6$ alkyl, $C_5$-$C_{10}$ cycloalkyl, $C_6$-$C_{10}$ aryl, and —Si(R³)₃ wherein each R³ is independently selected from $C_1$-$C_6$ alkyl;

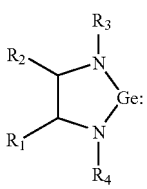

XI wherein:
R₁, R₂, R₃ and R₄ may be the same as or different from one another, and are independently selected from among H, $C_1$-$C_6$ alkyl, $C_5$-$C_{10}$ cycloalkyl, $C_6$-$C_{10}$ aryl, and —Si(R³)₃ wherein each R³ is independently selected from $C_1$-$C_6$ alkyl;

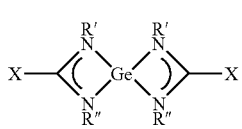

XII wherein:
R₁, R₂, R₃ and R₄ may be the same as or different from one another, and are independently selected from among H, $C_1$-$C_6$ alkyl, $C_5$-$C_{10}$ cycloalkyl, $C_6$-$C_{10}$ aryl, and —Si(R³)₃ wherein each R³ is independently selected from $C_1$-$C_6$ alkyl;

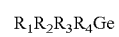

XVI wherein:
R₁, R₂, R₃, and R₄ may be the same as or different from one another, and are independently selected from among H, $C_1$-$C_6$ alkyl, $C_5$-$C_{10}$ cycloalkyl, $C_6$-$C_{10}$ aryl, and —Si(R³)₃ wherein each R³ is independently selected from $C_1$-$C_6$ alkyl,

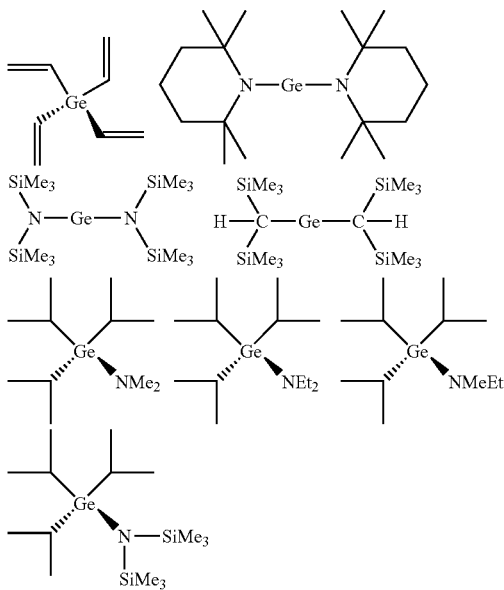

Ge(NMe$_2$)$_4$, Ge(NEtMe)$_4$, Ge(NEt$_2$)$_4$, iPr$_3$GeCl, iPr$_3$GeNMe$_2$, iPr$_3$GeNEtMe, iPr$_3$GeNEt$_2$, Ge butylamidinate, and [{nBuC(iPrN)$_2$}$_2$Ge].

Another aspect of the invention relates to a germanium precursor, selected from the group consisting of the above-specified germanium precursor species.

A still further aspect of the invention relates to a smooth amorphous germanium telluride or germanium antimony telluride film, as formed by the method described above, using a germanium precursor comprising Ge butylamidinate or [{nBuC(iPrN)$_2$}$_2$Ge].

Other aspects, features and embodiments of the invention will be more fully apparent from the ensuing disclosure and appended claims.

DETAILED DESCRIPTION

Figure 1:
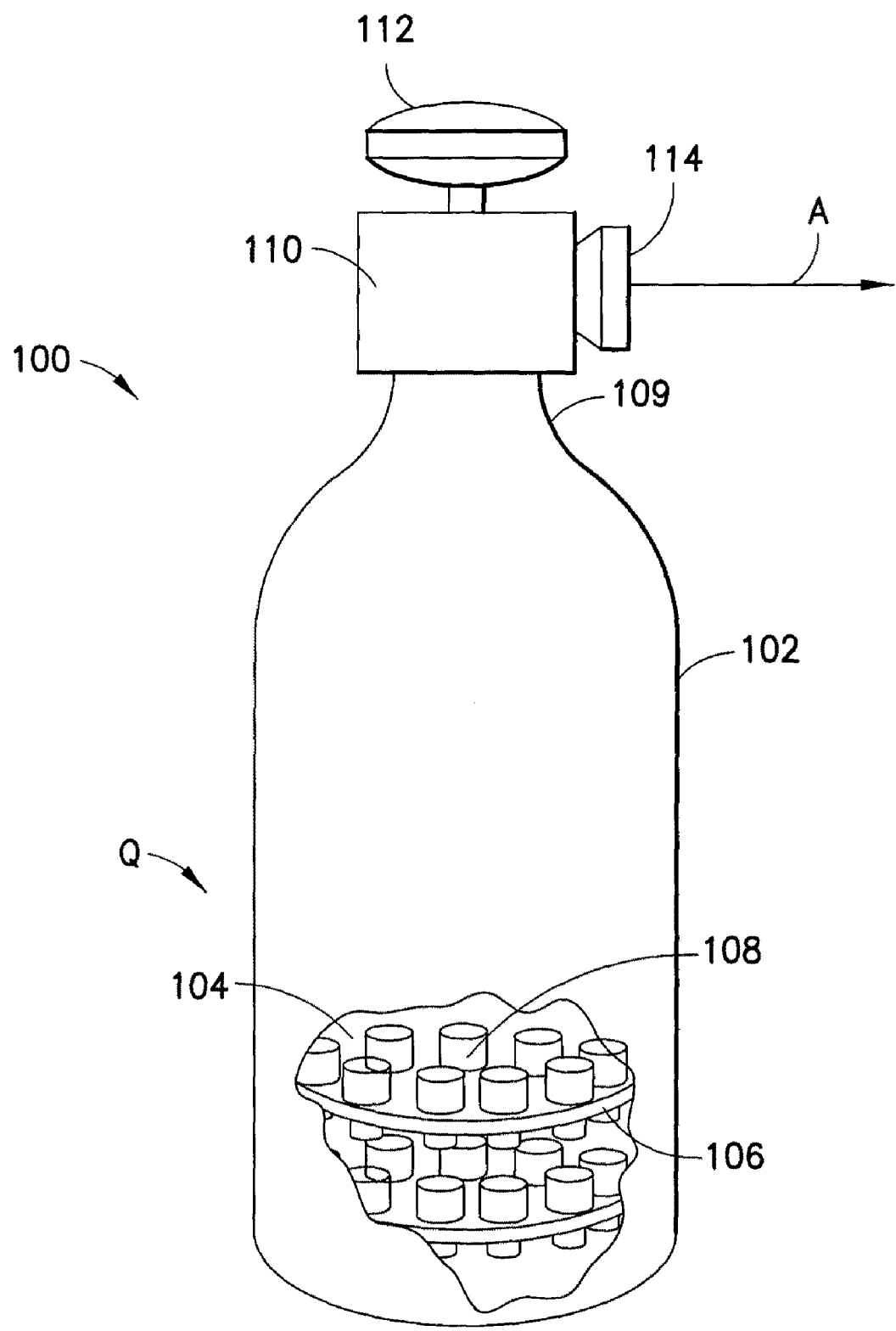
FIG. 1 is a schematic representation of a material storage and dispensing package containing a precursor of the present invention, in one embodiment thereof.

The present invention relates to the use of various germanium, tellurium, and antimony precursors, having utility for forming highly conformal germanium-containing films by low temperature (<300° C.) vapor deposition processes such as CVD and ALD, in methods for forming germanium-containing films. In other aspects, the invention relates to films formed using the methods, and microelectronic device products incorporating such films.

The precursors described herein are usefully employed in chemical vapor deposition and atomic layer deposition processes to form germanium-containing films, such as films of GeTe, GST, and the like. The GeTe films can be Ge$_x$Te 1-x systems, as such are defined in Scharnhorst and Riedl, "Photoconductivity in the amorphous Ge-rich Ge$_x$Te$_{1-x}$ system," Journal of Applied Physics, Vol. 45, p. 2971-2979 (1974), or Ge$_x$Sb$_y$Te$_z$ films, as such are described, for example, in Tsu, Journal of Vacuum Science & Technology A: Vacuum, Surfaces, and Films, Volume 17, Issue 4, Jul. 1999, pp. 1854-1860 (1999), the contents of both of which are hereby incorporated by reference. The films can advantageously be formed, using the processes described herein, to result in a substantially amorphous film layer.

The invention will be better understood with reference to the following definitions:

DEFINITIONS

As used herein, the term "film" refers to a layer of deposited material having a thickness below 1000 micrometers, e.g., from such value down to atomic monolayer thickness values. In various embodiments, film thicknesses of deposited material layers in the practice of the invention may for example be below 100, 10, or 1 micrometers, or in various thin film regimes below 200, 100, or 50 nanometers, depending on the specific application involved. As used herein, the term "thin film" means a layer of a material having a thickness below 1 micrometer.

As used herein, the singular forms "a", "and", and "the" include plural referents unless the context clearly dictates otherwise.

As used herein, the identification of a carbon number range, e.g., in $C_1$-$C_{12}$ alkyl, is intended to include each of the component carbon number moieties within such range, so that each intervening carbon number and any other stated or intervening carbon number value in that stated range, is encompassed, it being further understood that sub-ranges of carbon number within specified carbon number ranges may independently be included in smaller carbon number ranges, within the scope of the invention, and that ranges of carbon numbers specifically excluding a carbon number or numbers are included in the invention, and sub-ranges excluding either or both of carbon number limits of specified ranges are also included in the invention. Accordingly, $C_1$-$C_{12}$ alkyl is intended to include methyl, ethyl, propyl, butyl, pentyl, hexyl, heptyl, octyl, nonyl, decyl, undecyl and dodecyl, including straight chain as well as branched groups of such types. It therefore is to be appreciated that identification of a carbon number range, e.g., $C_1$-$C_{12}$, as broadly applicable to a substituent moiety, enables, in specific embodiments of the invention, the carbon number range to be further restricted, as a sub-group of moieties having a carbon number range within the broader specification of the substituent moiety. By way of example, the carbon number range e.g., $C_1$-$C_{12}$ alkyl, may be more restrictively specified, in particular embodiments of the invention, to encompass sub-ranges such as $C_1$-$C_4$ alkyl, $C_2$-$C_8$ alkyl, $C_2$-$C_4$ alkyl, $C_3$-$C_5$ alkyl, or any other sub-range within the broad carbon number range.

The precursors of the invention may be further specified in specific embodiments by provisos or limitations excluding specific substituents, groups, moieties or structures, in relation to various specifications and exemplifications thereof set forth herein. Thus, the invention contemplates restrictively defined compositions, e.g., a composition wherein $R^i$ is $C_1$-$C_{12}$ alkyl, with the proviso that $R^i \neq C_4$ alkyl when $R^j$ is silyl.

"Alkyls" as used herein include, but are not limited to, methyl, ethyl, propyl, isopropyl, butyl, s-butyl, t-butyl, pentyl and isopentyl and the like. "Aryls" as used herein includes hydrocarbons derived from benzene or a benzene derivative that are unsaturated aromatic carbocyclic groups of from 6 to 10 carbon atoms. The aryls may have a single or multiple rings. The term "aryl" as used herein also includes substituted aryls. Examples include, but are not limited to phenyl, naphthyl, xylene, phenylethane, substituted phenyl, substituted naphthyl, substituted xylene, substituted phenylethane and the like. "Cycloalkyls" as used herein include, but are not limited to cyclopropyl, cyclobutyl, cyclopentyl, cyclohexyl and the like. In all chemical formulae herein, a range of carbon numbers will be regarded as specifying a sequence of consecutive alternative carbon-containing moieties, including all moieties containing numbers of carbon atoms intermediate the endpoint values of carbon number in the specific range as well as moieties containing numbers of carbon atoms equal to an endpoint value of the specific range, e.g., $C_1$-$C_6$, is inclusive of $C_1$, $C_2$, $C_3$, $C_4$, $C_5$ and $C_6$, and each of such broader ranges may be further limitingly specified with reference to carbon numbers within such ranges, as sub-ranges thereof. Thus, for example, the range $C_1$-$C_6$ would be inclusive of and can be further limited by specification of sub-ranges such as $C_1$-$C_3$, $C_1$-$C_4$, $C_2$-$C_6$, $C_4$-$C_6$, etc. within the scope of the broader range.

The invention, as variously described herein in respect of features, aspects and embodiments thereof, may in particular implementations be constituted as comprising, consisting, or consisting essentially of, some or all of such features, aspects and embodiments, as well as elements and components thereof being aggregated to constitute various further implementations of the invention. The invention is described herein in various embodiments, and with reference to various features and aspects of the invention. The invention contemplates such features, aspects and embodiments in various permutations and combinations, as being within the scope of the invention. The invention may therefore be specified as comprising, consisting or consisting essentially of, any of such combinations and permutations of these specific features, aspects and embodiments, or a selected one or ones thereof.

I. Germanium Precursors

The precursors of the invention include various classes of germanium compositions. In one embodiment, the germanium precursor is $[\{nBuC(iPrN)_2\}_2Ge]$, also referred to herein as GeM.

The invention in another aspect relates to germanium precursors useful for CVD and ALD deposition of germanium films on substrates, of the following formulae I-XVI:

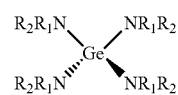

I wherein:
$R_1$ and $R_2$ may be the same as or different from one another, and are independently selected from H, $C_1$-$C_6$ alkyl, $C_2$-$C_5$ alkenyl, $C_5$-$C_{10}$ cycloalkyl, $C_6$-$C_{10}$ aryl, and —Si$(R_3)_3$ wherein each $R_3$ is independently selected from $C_1$-$C_6$ alkyl;

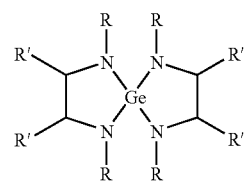

II wherein:
R and R' may be the same as or different from one another, and each R and R' is independently selected from H, $C_1$-$C_6$ alkyl, $C_2$-$C_5$ alkenyl, $C_5$-$C_{10}$ cycloalkyl, $C_6$-$C_{10}$ aryl, and —Si$(R_3)_3$ wherein each $R_3$ is independently selected from $C_1$-$C_6$ alkyl;

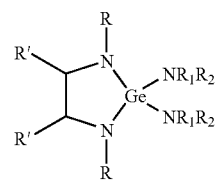

III wherein:
R, R', $R_1$ and $R_2$ may be the same as or different from one another, and each is independently selected from H, $C_1$-$C_6$ alkyl, $C_2$-$C_5$ alkenyl, $C_5$-$C_{10}$ cycloalkyl, $C_6$-$C_{10}$ aryl, and —Si$(R_3)_3$ wherein each $R_3$ is independently selected from $C_1$-$C_6$ alkyl;

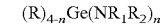

IV wherein:
R, $R_1$ and $R_2$ may be the same as or different from one another, and each is independently selected from H, $C_1$-$C_6$ alkyl, $C_2$-$C_5$ alkenyl, $C_5$-$C_{10}$ cycloalkyl, $C_6$-$C_{10}$ aryl, and —Si($R_3$)$_3$ wherein each $R_3$ is independently selected from $C_1$-$C_6$ alkyl; and n is an integer from 0 to 4 inclusive;

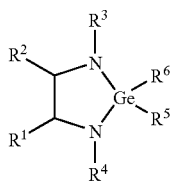

V wherein:
$R^1$, $R^2$, $R^3$, $R^4$, $R^5$ and $R^6$ may be the same as or different from one another, and each is independently selected from H, $C_1$-$C_6$ alkyl, $C_2$-$C_5$ alkenyl, $C_5$-$C_{10}$ cycloalkyl, $C_6$-$C_{10}$ aryl, and —Si($R_3$)$_3$ wherein each $R_3$ is independently selected from $C_1$-$C_6$ alkyl;

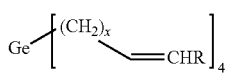

VI wherein:
R is selected from H, $C_1$-$C_6$ alkyl, and $C_6$-$C_{10}$ aryl; and
x is 0, 1 or 2;

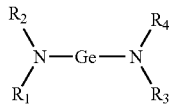

VII wherein:
$R_1$, $R_2$, $R_3$ and $R_4$ may be the same as or different from the others, and each is independently selected from among H, $C_1$-$C_6$ alkyl, $C_5$-$C_{10}$ cycloalkyl, $C_6$-$C_{10}$ aryl, and —Si($R_3$)$_3$ wherein each $R_3$ is independently selected from $C_1$-$C_6$ alkyl;

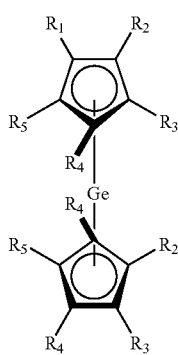

VIII wherein:
$R_1$, $R_2$, $R_3$, $R_4$, and $R_5$ may be the same as or different from one another, and each is independently selected from among H, $C_1$-$C_6$ alkyl, silyl, —Si(R')$_3$, $C_6$-$C_{10}$ cycloalkyl, $C_6$-$C_{10}$ aryl, —(CH$_2$)$_x$NR'R", and —(CH$_2$)$_x$OR'", wherein x=1, 2 or 3, and R', R" and R'" may be the same as or different from one another, and each is independently selected from $C_1$-$C_6$ alkyl;

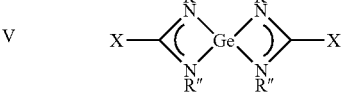

IX wherein:
R' and R" may be the same as or different from one another, and are independently selected from among H, $C_1$-$C_6$ alkyl, $C_5$-$C_{10}$ cycloalkyl, $C_6$-$C_{10}$ aryl, and —Si($R^3$)$_3$ wherein each $R^3$ is independently selected from $C_1$-$C_6$ alkyl; and
each X is independently selected from among $C_1$-$C_6$ alkyl, $C_1$-$C_6$ alkoxy, —NR$^1$R$^2$, and —C(R$^3$)$_3$, wherein each of R$^1$, R$^2$ and R$^3$ is independently selected from H, $C_1$-$C_6$ alkyl, $C_5$-$C_{10}$ cycloalkyl, $C_6$-$C_{10}$ aryl, and —Si(R$^4$)$_3$ wherein each R$^4$ is independently selected from $C_1$-$C_6$ alkyl;

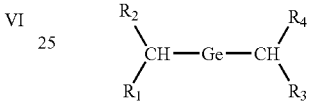

X wherein:
$R_1$, $R_2$, $R_3$ and $R_4$ may be same as or different from one another, and are independently selected from among H, $C_1$-$C_6$ alkyl, $C_5$-$C_{10}$ cycloalkyl, $C_6$-$C_{10}$ aryl, and —Si(R$^3$)$_3$ wherein each R$^3$ is independently selected from $C_1$-$C_6$ alkyl;

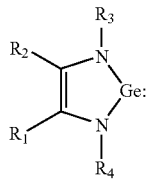

XI wherein:
$R_1$, $R_2$, $R_3$ and $R_4$ may be the same as or different from one another, and are independently selected from among H, $C_1$-$C_6$ alkyl, $C_5$-$C_{10}$ cycloalkyl, $C_6$-$C_{10}$ aryl, and —Si(R$^3$)$_3$ wherein each R$^3$ is independently selected from $C_1$-$C_6$ alkyl;

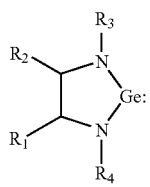

XII wherein:
$R_1$, $R_2$, $R_3$ and $R_4$ may be the same as or different from one another, and are independently selected from among H, $C_1$-$C_6$ alkyl, $C_5$-$C_{10}$ cycloalkyl, $C_6$-$C_{10}$ aryl, and —Si(R$^3$)$_3$ wherein each R$^3$ is independently selected from $C_1$-$C_6$ alkyl;

$R_1R_2R_3R_4Ge$        XVI wherein:

$R_1$, $R_2$, $R_3$, and $R_4$ may be the same as or different from one another, and are independently selected from among H, $C_1$-$C_6$ alkyl, $C_5$-$C_{10}$ cycloalkyl, $C_6$-$C_{10}$ aryl, and —Si$(R^3)_3$ wherein each $R^3$ is independently selected from $C_1$-$C_6$ alkyl.

The synthesis of the above-described germanium precursors can variously be carried out in a ready manner, utilizing synthetic preparations of the types variously shown below. In each instance RMgCl, RMgBr, RMgI, RLi, and RNa can be used as alternative reagents. Further, GeBr$_4$ can be used in place of GeCl$_4$; LiNR$_2$ can be replaced by NaNR$_2$ or KNR$_2$; and Na($C_5R_5$) can be used as an alternative to K($C_5R_5$). Moreover, a multi-step synthetic approach may be employed to generate mixed alkyl species through oxidative addition to a Ge(II) complex to generate Ge(IV) precursors, as shown below:

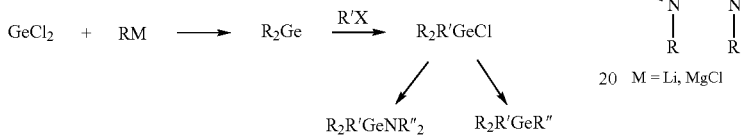

wherein:

R, R', and R" may be the same as or different from one another, and each is independently selected from H, $C_1$-$C_6$ alkyl, $C_2$-$C_6$ alkenyl, $C_5$-$C_{10}$ cycloalkyl, $C_6$-$C_{10}$ aryl, and —Si$(R_3)_3$ wherein each $R_3$ is independently selected from $C_1$-$C_6$ alkyl, and M is Li, Na, MgCl, MgBr, or MgI.

Germanium (IV) Precursors for GST Films

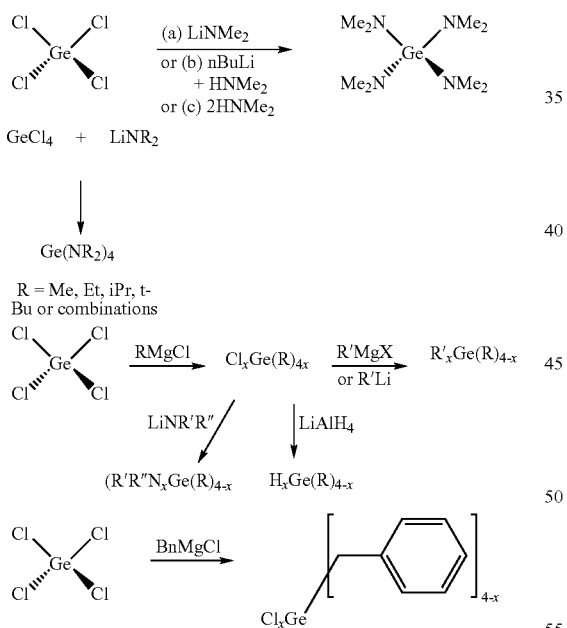

and correspondingly a tetraallylgermanium complex

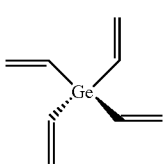

can be formed from such tetrachlorogermanium starting material using a corresponding allyl Grignard reagent R*MgCl, wherein R* is allyl Ge Precursors for GST Films

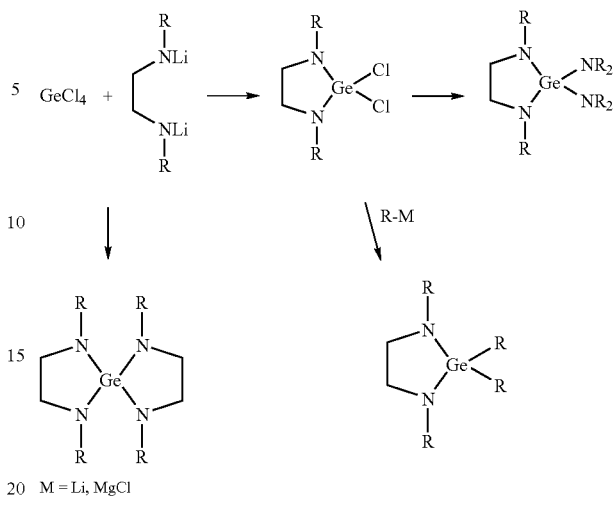

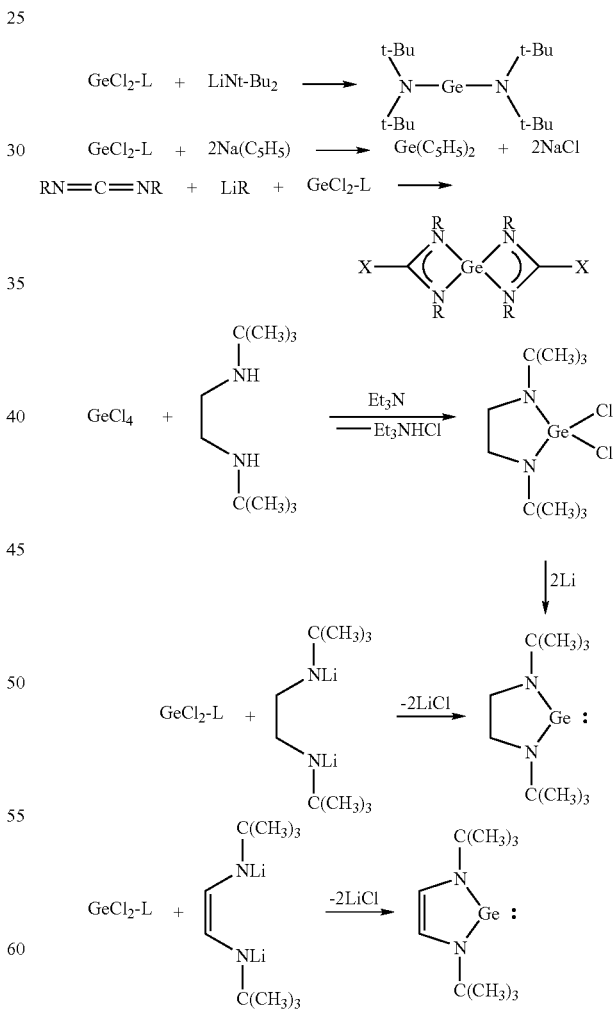

Illustrative Ge(II) compounds that may be usefully employed for CVD or ALD of germanium-containing films include the following:

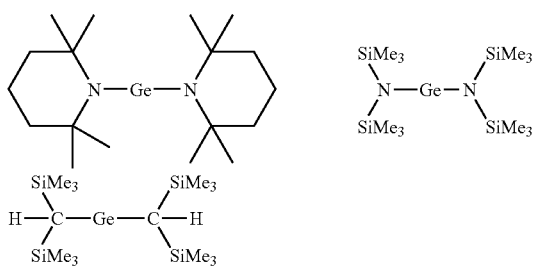

In various embodiments of the invention, dialkylaminoisopropylgermane precursors are used for CVD/ALD formation of GST thin films. Such precursors may be synthesized by a reaction scheme such as that shown below:

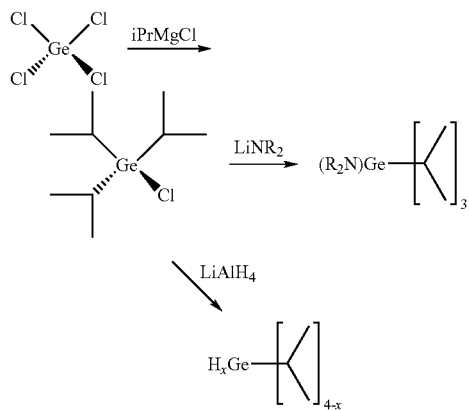

to form germanium complexes such as:

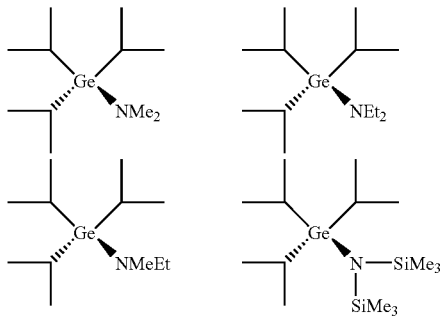

The above-described germanium precursors are useful for CVD and ALD applications, to deposit germanium-containing films on substrates. Tetrakisamidogermanes and triisopropylamines useful for such applications and amenable to transport with a heated bubbler include, for example, $Ge(NMe_2)_4$, $Ge(NEtMe)_4$, $Ge(NEt_2)_4$, $iPr_3GeCl$, $iPr_3GeNMe_2$, $iPr_3GeNEtMe$, and $iPr_3GeNEt_2$. The volatility of the germanium precursors of the invention can be readily measured by STA thermogravimetric technique (e.g., by determining material transport under atmospheric pressure in argon) and GC analysis.

In specific embodiments of germanium precursors of the present invention containing alkyl substituents, isopropyl substituents are in many cases preferred over methyl groups due to the ability of the isopropyl substituents to undergo beta-hydrogen elimination, thereby facilitating low temperature decomposition processing of the germanium precursor, without producing significant carbon residue.

Nitrogen containing germanium precursors of the invention have the intrinsic benefit in many applications of mediating some incorporation of nitrogen in final films. In this respect, Si- and N-doped GST materials have lower reset currents, thereby rendering phase-change memory based on such materials more stable and less susceptible to drift.

As an additional advantage, various germane precursors of the invention undergo hydrogermolysis coupling reactions to form Ge—Ge bonds, via the reaction $R_3GeNR'_2 + R_3GeH \rightarrow R_3Ge—GeR_3$, to yield digermane CVD precursors enabling highly efficient Ge-containing film deposition to be achieved, in relation to mono-germane precursors.

The germanium precursors of the invention can contain a wide variety of ligand species as moieties thereof. Such ligands may for example include, without limitation, allyl, benzyl, t-butyl, cylopentadienyl, hydride, phenyl, and alkyl. Bidentate amines (e.g. N,N-dialkylethylenediamine) can also be used.

The germanium precursors can be delivered in solution or suspension in a liquid delivery technique, using suitable solvent media, or may be delivered for vapor phase desposition of Ge-containing films by solid delivery techniques, e.g., as described hereinabove in respect of the antimony precursors of the invention.

In use as CVD/ALD precursors, the Ge precursor may be deposited separately or in combination with other precursors, e.g., with Sb and Te complexes such as $iPr_3Sb$, $Sb(NR_2)_3$, $iPr_2Te$ and $Te(NR_2)_2$ to form GST films.

One illustrative germanium precursor of the invention is Ge(triisopropyl)(methylethylamide), referred to sometimes hereinafter as GePNEM. This precursor can be employed to deposit germanium on a substrate at suitable deposition process conditions, e.g., deposition temperature in a range of from 300° C. to 450° C., and at pressure ranging from subatmospheric to superatmospheric (e.g., in a range of from about 0.5 torr to 15 atmospheres or more). Set out in Table I below is a listing of film deposition rate, in Angstroms/minute, at varying temperature and pressure conditions, for deposition of germanium on substrates from the GePNEM precursor, delivered to the substrate in a carrier gas flow of hydrogen gas at 200 standard cubic centimeters per minute.

TABLE I

Film Deposition Rate of Germanium Deposited at Varying Temperature and Pressure Conditions

| Temperature (° C.) | Temperature 1/T (K) | Pressure 0.8 torr | Pressure 8 torr |
|---|---|---|---|
| 300 | 0.001745201 | 0.14 Å/min | 0.35 Å/min |
| 320 | 0.001686341 | 0.45 Å/min | |
| 340 | 0.001631321 | 1.32 Å/min | 0.8 Å/min |
| 360 | 0.001579779 | 1.48 Å/min | 1.28 Å/min |
| 380 | 0.001531394 | 2.4 Å/min | 2.7 Å/min |
| 400 | 0.001485884 | 3.4 Å/min | 2.3 Å/min |
| 420 | 0.001443001 | 6.8 Å/min | 10.5 Å/min |
| 440 | 0.001403 | 6.5 Å/min | |

GePNEM deposition with 200 SCCM $H_2$

In another determination of film thicknesses of germanium achieved by deposition from the GePNEM precursor, deposition carried out for a period of 16 minutes gave the following results: (i) temperature=400° C., pressure=800 millitorr, reactant gas $H_2$, film thickness=57 Å; (ii) temperature=400°

C., pressure=800 millitorr, reactant gas $NH_3$, film thickness=94 Å; and (iii) temperature=400° C., pressure=8000 millitorr, reactant gas $H_2$, film thickness=36 Å. These results evidence the suitability of GePNEM for forming germanium or germanium-containing thin films on substrates by vapor deposition techniques.

In various specific embodiments, the invention contemplates a precursor mixture including germanium precursor, antimony precursor and tellurium precursor, wherein at least one of the germanium precursor and antimony precursor includes a precursor selected from among the metal complexes of formulae (A), (B), (C), (D) and (E)(I)-(XVI) described hereinabove.

II. Antimony Precursors

To form antimony-containing films, one can use antimony-containing precursors, for example, antimony precursors of the following formulae (A), (B) and (C):

$$Sb(NR^1R^2)(R^3N(CR^5R^6)_mNR^4) \quad (A)$$

wherein:
$R^1$, $R^2$, $R^3$, and $R^4$ may be the same as or different from one another, and are independently selected from $C_1$-$C_6$ alkyl, $C_3$-$C_6$ cycloalkyl, $C_2$-$C_6$ alkenyl (e.g., vinyl, allyl, etc.), $C_3$-$C_6$ alkylsilyl, $C_6$-$C_{10}$ aryl,
each of $R^5$ and $R^6$ may be the same as or different from one another and are independently selected from hydrogen, $C_1$-$C_6$ alkyl, $C_3$-$C_6$ cycloalkyl, $C_2$-$C_6$ alkenyl (e.g., vinyl, allyl, etc.), $C_3$-$C_6$ alkylsilyl, and $C_6$-$C_{10}$ aryl; and
m is an integer from 1 to 4 inclusive;

$$Sb(R^1)(R^2N(CR^4R^5)_mNR^3) \quad (B)$$

wherein:
$R^1$, $R^2$, and $R^3$ may be the same as or different from one another, and are independently selected from $C_1$-$C_6$ alkyl, $C_3$-$C_6$ cycloalkyl, $C_2$-$C_6$ alkenyl (e.g., vinyl, allyl, etc.), $C_3$-$C_6$ alkylsilyl, and $C_6$-$C_{10}$ aryl;
each of $R^4$ and $R^5$ may be the same as or different from one another and is independently selected from hydrogen, $C_1$-$C_6$ alkyl, $C_3$-$C_6$ cycloalkyl, $C_2$-$C_6$ alkenyl (e.g., vinyl, allyl, etc.), $C_3$-$C_6$ alkylsilyl, and $C_6$-$C_{10}$ aryl; and
m is an integer from 1 to 4 inclusive;

$$Sb(R^1)_{3-n}(NR^2R^3)_n \quad (C)$$

wherein:
$R^1$, $R^2$ and $R^3$ may be the same as or different from one another and are independently selected from hydrogen, $C_1$-$C_6$ alkyl, $C_3$-$C_6$ cycloalkyl, $C_2$-$C_6$ alkenyl (e.g., vinyl, allyl, etc.), silyl, $C_3$-$C_6$ alkylsilyl, $C_6$-$C_{10}$ aryl and —$NR^4R^5$, wherein each of $R^4$ and $R^5$ is selected from among H and $C_1$-$C_4$; and
n is an integer from 0 to 3 inclusive.

The invention in another aspect relates to germanyl and silyl antimony precursors of formula (D):

$$(R^4)_nSb(E(R^1R^2R^3))_{3-n} \quad (D)$$

wherein:
$R^1$, $R^2$, $R^3$, and $R^4$ may be the same as or different from one another, and are independently selected from $C_1$-$C_6$ alkyl, $C_3$-$C_6$ cycloalkyl, $C_3$-$C_6$ alylsilyl, $C_6$-$C_{10}$ aryl, and alkylamino of the formula —$NR^5R^6$ wherein each of $R^5$ and $R^6$ is independently selected from H and $C_1$-$C_4$ alkyl;
E is silicon (Si) or germanium (Ge); and
n is an integer from 0 to 3 inclusive.

The foregoing precursors may be usefully employed for CVD and ALD of Sb, Sb/Ge, Sb/Te and GST films.

Such precursors may also be used in low temperature deposition applications with reducing co-reactants such as hydrogen, hydrogen plasma, amines, imines, hydrazines, silanes, silyl chalcogenides (e.g., $(Me_3Si)_2Te$), germanes (e.g., $GeH_4$), ammonia, alkanes, alkenes and alkynes.

When specific precursors are in a liquid state, they may be used for liquid delivery in neat liquid form.

Alternatively, when such precursors are in a liquid or solid state, they may be employed in suitable solvents, as a solution or suspension of the precursor. In specific applications, suitable solvents for such purpose include alkanes (e.g., hexane, heptane, octane and pentane), aryl solvents (e.g., benzene, toluene), amines (e.g., triethylamine, tert-butylamine), imines, hydrazines and ethers.

The choice of a specific solvent composition for a particular antimony precursor or for a specific antimony precursor in combination with other germanium and tellurium precursors, may be readily determined, within the skill of the art based on the disclosure herein, to select an appropriate single component or multiple component solvent medium for liquid delivery vaporization and transport of the specific precursor component(s) involved.

In various embodiments, where the antimony precursor is in a solid state, a solid delivery system may be utilized for delivery of the antimony precursor, such as for example the ProE-Vap® solid delivery and vaporizer system commercially available from ATMI, Inc., Danbury, Conn., USA.

The antimony precursors of the invention can be "fine-tuned" by choice of appropriate substituents, within the broad formulae set out hereinabove, to provide desired characteristics of thermal stability, volatility and compatibility with other co-reagents or components in a multi-component precursor system.

The antimony precursors of the invention are readily synthesized, by synthetic routes including those described below.

The antimony precursor of the general formula (A):

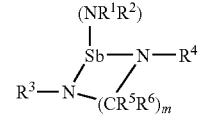

can for example be synthesized according to the following reaction scheme (A):

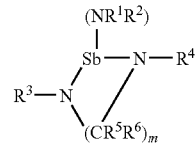

and the antimony precursor of the general formula (B):

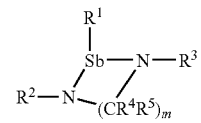

can be synthesized according to the following reaction scheme (B):

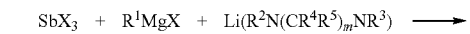

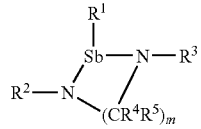

or by the following reaction scheme (C):

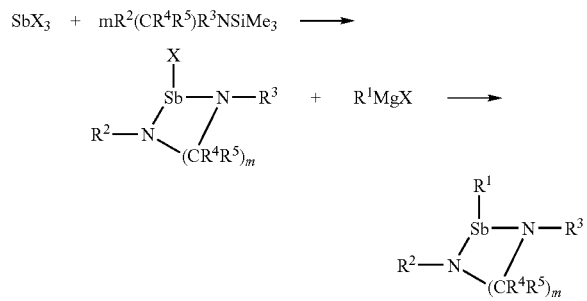

The antimony precursor of the general formula (C) can be formed by synthesis in a corresponding manner.

The antimony precursor of the general formula (D), having the following structure:

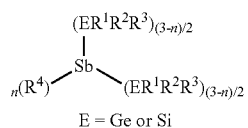

E = Ge or Si can for example be synthesized according to the following reaction schemes (D), when n is zero, or (E), when n is 2:

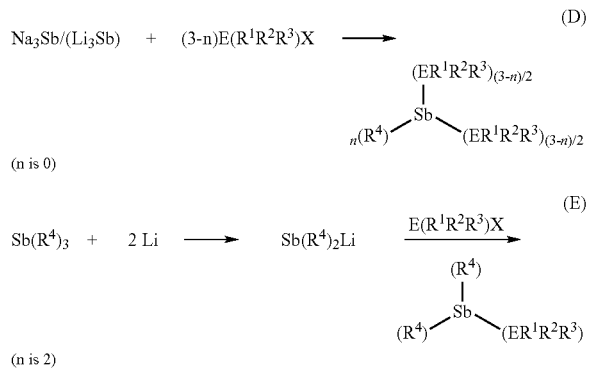

(n is 2)
E = Ge or Si wherein X is halo (fluorine, bromine, chlorine, iodine).

In the foregoing synthetic examples, RMgX and RLi can be used as alternative synthesis reagents.

As specific examples illustrative of precursors of the invention, the precursors $Sb(NMeEt)_3$, $Sb(CH=CMe_2)_3$, $Sb(CH_2CH=CH_2)_3$ and $Sb(NMe_2)_3$ were synthesized and characterized. The precursors $Sb(NMe_2)_3$ and $Sb(NMeEt)_3$ were determined to exhibit photo-sensitivity and therefore to require storage in a container protected from light exposure or in other photo-resistant packaging, to avoid light-induced decomposition thereof. Similar considerations are applicable to $Sb(CH=CMe_2)_3$ and $Sb(CH_2CH=CH_2)_3$.

Figure 2:
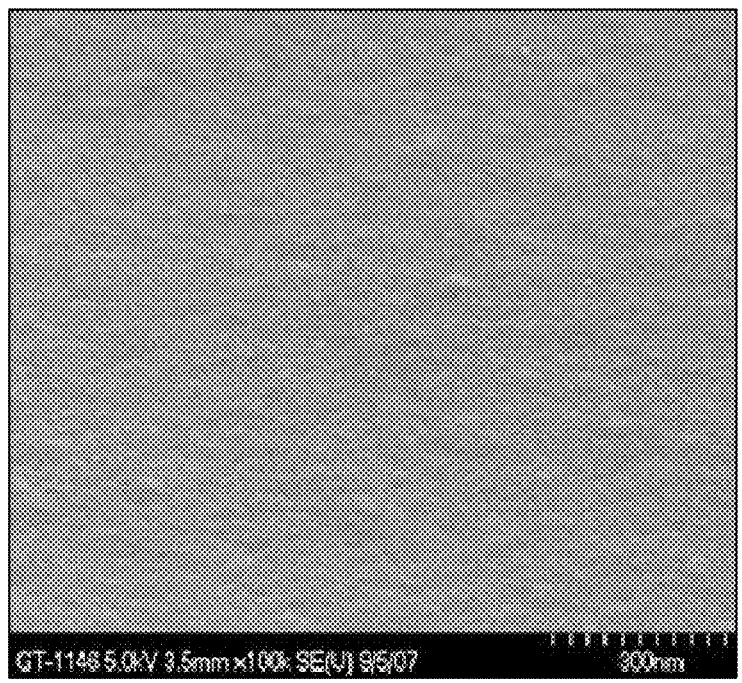
FIG. 2 is a scanning electron micrograph of a germanium telluride film after annealing at one hour in nitrogen atmosphere, at 400° C.

FIG. 1 shows the nuclear magnetic resonance spectrum of $Sb(NMeEt)_3$ and FIG. 2 shows the nuclear magnetic resonance spectrum of $Sb(NMe_2)_3$.

Figure 3:
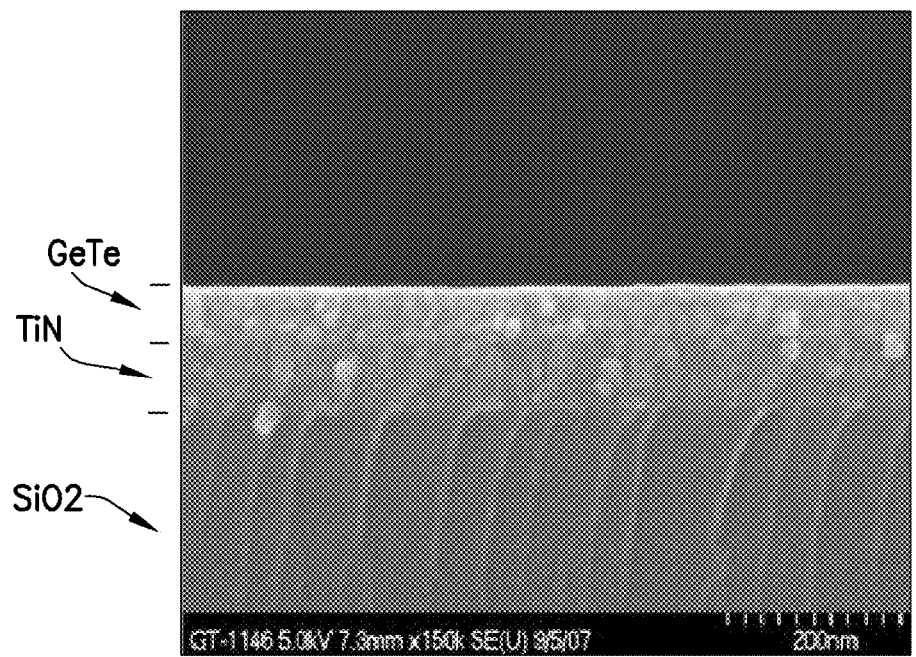
FIG. 3 is a cross-sectional elevation SEM view of the germanium telluride film of FIG. 2, showing the smooth character of the germanium telluride film deposited on the titanium nitride layer formed on the silicon dioxide substrate.

FIG. 3 is a simultaneous thermal analysis (STA) graph for these two precursors, $Sb(NMeEt)_3$ and $Sb(NMe_2)_3$, in which percentage thermogravimetry (TG) is plotted as a function of temperature, in degrees Centigrade.

Additional classes of antimony precursors can also be used. Such antimony precursors are suitable for use in forming GST films, in conjunction with the use of suitable germanium and tellurium precursors.

Such additional classes of antimony precursors include those of formulae (F), (G), (H), (I), (J), (K), (L) and (M), as defined below:

(F) amimidates, guanidates and isoureates of the formula:

wherein:
where each $R^1$ and $R^2$ is independently selected from among H, $C_1$-$C_6$ alkyl, $C_5$-$C_{10}$ cycloalkyl, $C_6$-$C_{10}$ aryl, and —Si$(R^3)_3$ wherein each $R^3$ is independently selected from $C_1$-$C_6$ alkyl;
each X is independently selected from among $C_1$-$C_6$ alkoxy, —NR$^4$R$^5$, and —C$(R^6)_3$, wherein each of $R^4$, $R^5$ and $R^6$ is independently selected from H, $C_1$-$C_6$ alkyl, $C_5$-$C_{10}$ cycloalkyl, $C_6$-$C_{10}$ aryl, and —Si$(R^3)_3$ wherein each $R^3$ is independently selected from $C_1$-$C_6$ alkyl;
each $R^7$ is independently selected from among $C_1$-$C_6$ alkoxy, —NR$^8$R$^9$, and —C$(R^{10})_3$, wherein each of $R^8$, $R^9$ and $R^{10}$ is independently selected from H, $C_1$-$C_6$ alkyl, $C_5$-$C_{10}$ cycloalkyl, $C_6$-$C_{10}$ aryl, —Si$(R^3)_3$, and —Ge$(R^3)_3$ wherein each $R^3$ is independently selected from $C_1$-$C_6$ alkyl; and
n is an integer from 0 to 3;

(G) tetra-alkyl guanidates of the formula:

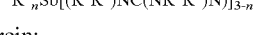

wherein:
each of $R^1$ and $R^2$ is independently selected from among H, $C_1$-$C_6$ alkyl, $C_5$-$C_{10}$ cycloalkyl, $C_6$-$C_{10}$ aryl, and —Si$(R^9)_3$ wherein each $R^9$ is independently selected from $C_1$-$C_6$ alkyl;
each of $R^3$ and $R^4$ is independently selected from H, $C_1$-$C_6$ alkyl, $C_5$-$C_{10}$ cycloalkyl, $C_6$-$C_{10}$ aryl, and —Si$(R^9)_3$ wherein each $R^9$ is independently selected from $C_1$-$C_6$ alkyl;
each $R^5$ is independently selected from among $C_1$-$C_6$ alkoxy, —NR$^6$R$^7$, and —C$(R^8)_3$, wherein each of $R^6$, $R^7$ and $R^8$ is independently selected from H, $C_1$-$C_6$ alkyl, $C_5$-$C_{10}$ cycloalkyl, $C_6$-$C_{10}$ aryl, —Si$(R^9)_3$, and —Ge$(R^9)_3$ wherein each $R^9$ is independently selected from $C_1$-$C_6$ alkyl; and
n is an integer from 0 to 3.

(H) carbamates and thiocarbamates of the formula:

wherein:
each X is independently selected from among $C_1$-$C_6$ alkoxy, —NR$^1$R$^2$, and —C$(R^3)_3$, wherein each of $R^1$, $R^2$ and $R^3$ is independently selected from H, $C_1$-$C_6$ alkyl, $C_5$-$C_{10}$ cycloalkyl, $C_6$-$C_{10}$ aryl, and —Si$(R^5)_3$ wherein each $R^5$ is independently selected from $C_1$-$C_6$ alkyl;
each $R^4$ is independently selected from among $C_1$-$C_6$ alkoxy, —NR$^1$R$^2$, and —C$(R^3)_3$, wherein each of $R^1$, $R^2$ and $R^3$ is independently selected from H, $C_1$-$C_6$ alkyl, $C_5$-$C_{10}$ cycloalkyl, $C_6$-$C_{10}$ aryl, and —Si$(R^5)_3$, —Ge$(R^5)_3$ wherein each $R^5$ is independently selected from $C_1$-$C_6$ alkyl;
E is either O or S; and
n is an integer from 0 to 3;

(I) beta-diketonates, diketoiminates, and diketiiminates, of the formulae:

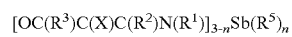

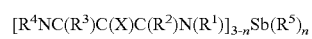

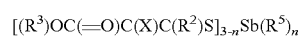

where each of $R^1$, $R^2$, $R^3$ and $R^4$ is independently selected from among H, $C_1$-$C_6$ alkyl, $C_5$-$C_{10}$ cycloalkyl, $C_6$-$C_{10}$ aryl, and —Si($R^6$)$_3$ wherein each $R^6$ is independently selected from $C_1$-$C_6$ alkyl;

each X is independently selected from among $C_1$-$C_6$ alkoxy, —NR$^6$R$^7$, and —C($R^8$)$_3$, wherein each of $R^6$, $R^7$ and $R^8$ is independently selected from H, $C_1$-$C_6$ alkyl, $C_5$-$C_{10}$ cycloalkyl, $C_6$-$C_{10}$ aryl, and —Si($R^6$)$_3$ wherein each $R^6$ is independently selected from $C_1$-$C_6$ alkyl;

each $R^5$ is independently selected from among guanidinate, amimidate, isoureate, allyl, $C_1$-$C_6$ alkoxy, —NR$^9$R$^{10}$, and —C($R^{11}$)$_3$, wherein each of $R^9$, $R^{10}$ and $R^{11}$ is independently selected from H, $C_1$-$C_6$ alkyl, $C_5$-$C_{10}$ cycloalkyl, $C_6$-$C_{10}$ aryl, —Si($R^6$)$_3$, and —Ge($R^6$)$_3$ wherein each $R^6$ is independently selected from $C_1$-$C_6$ alkyl; and n is an integer from 0 to 3.

(J) allyls of the formulae:

$$R^4{}_n Sb[R^1NC(X)C(R^2R^3)]_{3-n} \quad (i)$$

$$R^4{}_n Sb[(R^1O)NC(X)C(R^2R^3))]_{3-n} \quad (ii)$$

$$R^4{}_n Sb[(R^1R^5)NC(X)C(R^2R^3))]_{3-n} \quad (iii)$$

$$R^4 Sb[(ONC(X)C(R^2R^3))] \quad (iv)$$

where each $R^1$, $R^2$, $R^3$ and $R^5$ is independently selected from among H, $C_1$-$C_6$ alkyl, $C_5$-$C_{10}$ cycloalkyl, $C_6$-$C_{10}$ aryl, and —Si($R^6$)$_3$ wherein each $R^6$ is independently selected from $C_1$-$C_6$ alkyl;

each X is independently selected from among $C_1$-$C_6$ alkoxy, —NR$^1$R$^2$, and —C($R^3$)$_3$, wherein each of $R^1$, $R^2$ and $R^3$ is independently selected from H, $C_1$-$C_6$ alkyl, $C_5$-$C_{10}$ cycloalkyl, $C_6$-$C_{10}$ aryl, and —Si($R^6$)$_3$ wherein each $R^6$ is independently selected from $C_1$-$C_6$ alkyl;

each $R^4$ is independently selected from among guanidinates, amimidates, isoureates, beta-diketonates, diketoiminates, diketiiminates, $C_1$-$C_6$ alkoxy, —NR$^7$R$^8$, and —C($R^9$)$_3$, wherein each of $R^7$, $R^8$ and $R^9$ is independently selected from H, $C_1$-$C_6$ alkyl, $C_5$-$C_{10}$ cycloalkyl, $C_6$-$C_{10}$ aryl, —Si($R^6$)$_3$, and —Ge($R^6$)$_3$ wherein each $R^6$ is independently selected from $C_1$-$C_6$ alkyl; and n is an integer from 0 to 3.

(L) cyclopentadienyl (Cp) antimony compounds wherein the Cp moiety is of the formulae:

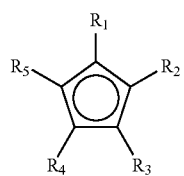

wherein each of $R_1$, $R_2$, $R_3$, $R_4$ and $R_5$ can be the same as or different from the others, and each is independently selected from among hydrogen, $C_1$-$C_{12}$ alkyl, $C_1$-$C_{12}$ alkylamino, $C_6$-$C_{10}$ aryl, $C_1$-$C_{12}$ alkoxy, $C_3$-$C_6$ alkylsilyl, $C_2$-$C_{12}$ alkenyl, $R^1R^2NNR^3$, wherein $R^1$, $R^2$ and $R^3$ may be the same as or different from one another and each is independently selected from $C_1$-$C_6$ alkyl, and pendant ligands including functional group(s) providing further coordination to the antimony central atom, and selected from among aminoalkyl, alkoxyalkyl, aryloxyalkyl, imidoalkyl, and acetylalkyl, having the following formulae:

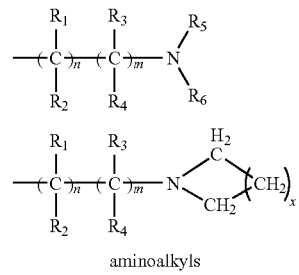

aminoalkyls wherein: the methylene (—CH$_2$—) moiety could alternatively be another divalent hydrocarbyl moiety; each of $R_1$-$R_4$ is the same as or different from one another, with each being independently selected from among hydrogen, $C_1$-$C_6$ alkyl and $C_6$-$C_{10}$ aryl; each of $R_5$ and $R_6$ is the same as or different from the other, with each being independently selected from among $C_1$-$C_6$alkyl; n and m are each selected independently as having a value of from 0 to 4, with the proviso that m and n cannot be 0 at the same time, and x is selected from 1 to 5;

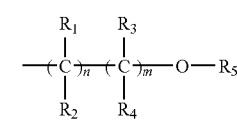

alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently as having a value of from 0 to 4, with the proviso that m and n cannot be 0 at the same time;

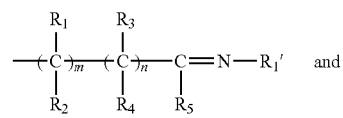

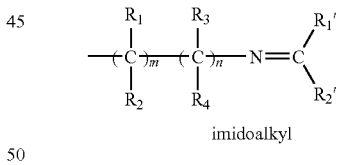

imidoalkyl wherein each of $R_1$, $R_2$, $R_3$, $R_4$, $R_5$ is the same as or different from one another, with each being independently selected from among hydrogen, $C_1$-$C_6$ alkyl, and $C_6$-$C_{10}$ aryl; each of $R_1'$, $R_2'$ is the same as or different from one another, with each being independently selected from $C_1$-$C_6$ alkyl, and $C_6$-$C_{10}$ aryl; and n and m are selected independently from 0 to 4, with the proviso that m and n cannot be 0 at the same time;

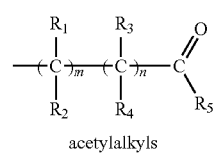

acetylalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, $C_6$-$C_{10}$ aryl, and $C_1$-$C_5$ alkoxy; and n and m are selected independently from 0 to 4, with the proviso that m and n cannot be 0 at the same time;

wherein non-Cp ligand(s) of the antimony Cp compound can optionally include ligands selected from the group consisting of guanidinates, aminidates, isoureates, allyls, beta-diketonates, diketoiminates, and diketiiminates; and (M) alkyls, alkoxides and silyls with pendent ligands, of the formulae:

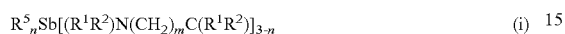  (i)

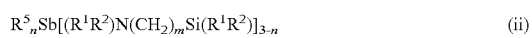  (ii)

  (iii)

where each of $R^1$ and $R^2$ is independently selected from among H, $C_1$-$C_6$ alkyl, $C_5$-$C_{10}$ cycloalkyl, $C_6$-$C_{10}$ aryl, and —Si($R^3$)$_3$ wherein each $R^3$ is independently selected from $C_1$-$C_6$ alkyl;

each $R^5$ is independently selected from among guanidinates, amimidates, isoureates, beta-diketonates, diketoiminates, diketiiminates, $C_1$-$C_6$ alkoxy, —NR$^6$R$^7$, and —C($R^8$)$_3$, wherein each of $R^6$, $R^7$ and $R^8$ is independently selected from H, $C_1$-$C_6$ alkyl, $C_5$-$C_{10}$ cycloalkyl, $C_6$-$C_{10}$ aryl, —Si($R^3$)$_3$, and —Ge($R^3$)$_3$ wherein each $R^3$ is independently selected from $C_1$-$C_6$ alkyl;

n is an integer from 0 to 3;

m is integer from 0 to 4.

Antimony precursors of a general type within the foregoing classes (F)-(M) include precursors having the following structures, wherein the various "R" groups in these structures are not necessarily numbered in exact correspondence with the substituent numberings in the above formulae, but nonetheless reflect the substituted positions in general fashion, which will be understood in reference to the above definitions of the substituents at the various positions of the associated molecules.

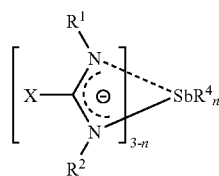

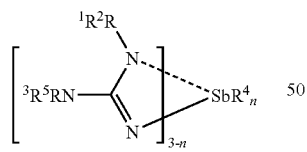

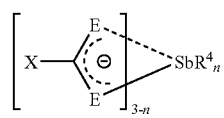

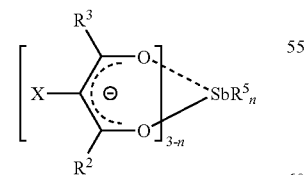

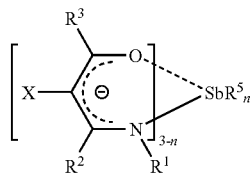

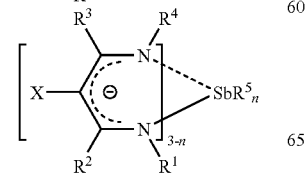

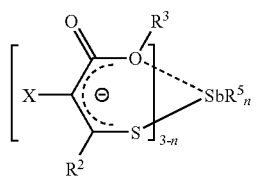

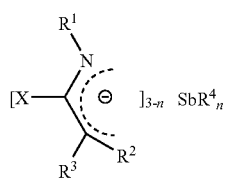 A

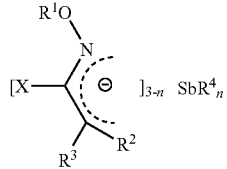 B

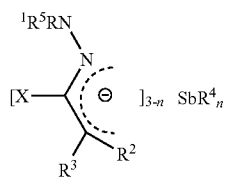 C

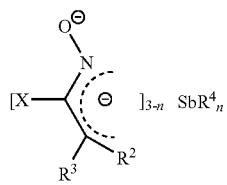 D

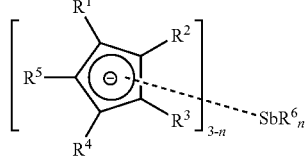

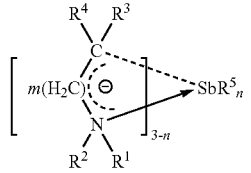 A

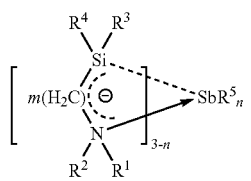 B

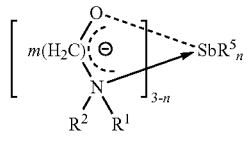 C including the following illustrative complexes:

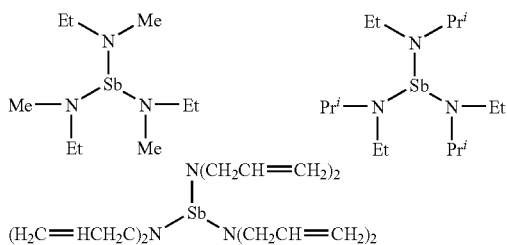

antimony amides of the formulae

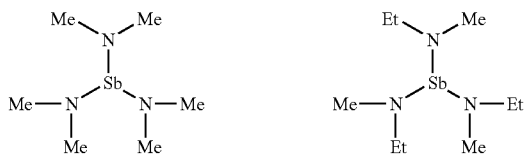

antimony (III) alkyl/amino precursors of the formulae:

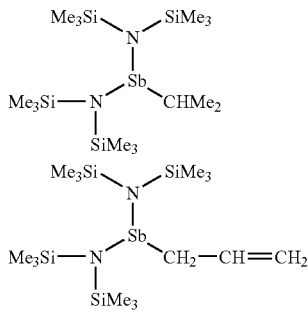

and stibenes with germanium anions, of the formulae:

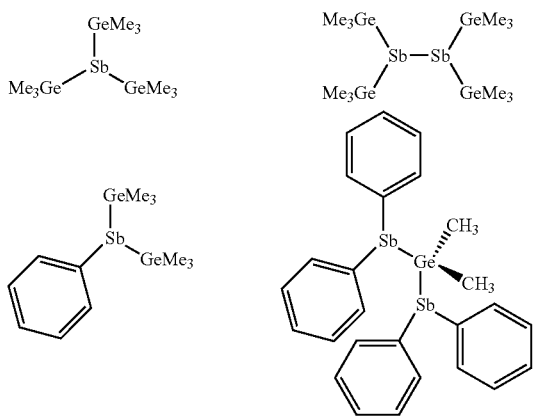

The antimony precursors of classes (F)-(M) are usefully employed for deposition of antimony at low temperature with reducing co-reactants, e.g., reactants such as hydrogen, $H_2$/plasma, amines, imines, hydrazines, silanes, silyl chalcogenides such as $(Me_3Si)_2Te$, germanes such as $GeH_4$, ammonia, alkanes, alkenes, and alkynes.

The antimony precursors may be delivered for such deposition via liquid delivery techniques, in which precursors that are liquids may be used in neat liquid form, and precursors that are solids or liquids may be delivered in solutions or suspensions, in combination with suitable solvents, such as alkane solvents (e.g., hexane, heptane, octane, and pentane), aryl solvents (e.g., benzene or toluene), amines (e.g., triethylamine, tert-butylamine), imines and hydrazines. The utility of specific solvent compositions for particular antimony precursors can be readily empirically determined, to select an appropriate single component or multicomponent solvent medium for liquid delivery vaporization and transport of the specific antimony precursor that is employed.

In another aspect of the invention, solid delivery techniques may be employed, in which the solid precursor is volatilized, to form a precursor vapor that is delivered to the deposition chamber for forming an antimony or antimony-containing film on the substrate. The solid precursor may be packaged for such use in a storage and dispensing package of suitable character, such as the ProE-Vap solid delivery and vaporizer unit commercially available from ATMI, Inc. (Danbury, Conn., USA).

The foregoing precursors may be usefully employed for CVD and ALD of Sb, Sb/Ge, Sb/Te and GST films.

When specific precursors are in a liquid state, they may be used for liquid delivery in neat liquid form.

Alternatively, when such precursors are in a liquid or solid state, they may be employed in suitable solvents, as a solution or suspension of the precursor. In specific applications, suitable solvents for such purpose include alkanes (e.g., hexane, heptane, octane and pentane), aryl solvents (e.g., benzene, toluene), amines (e.g., triethylamine, tert-butylamine), imines, hydrazines and ethers.

The choice of a specific solvent composition for a particular antimony precursor or for a specific antimony precursor in combination with other germanium and tellurium precursors, may be readily determined, within the skill of the art based on the disclosure herein, to select an appropriate single component or multiple component solvent medium for liquid delivery vaporization and transport of the specific precursor component(s) involved.

The antimony precursors of the invention can be "fine-tuned" by choice of appropriate substituents, within the broad formulae set out hereinabove, to provide desired characteristics of thermal stability, volatility and compatibility with other co-reagents or components in a multi-component precursor system.

The antimony precursors of the invention are readily synthesized, by synthetic routes including those described below.

The antimony precursor of the general formula (A):

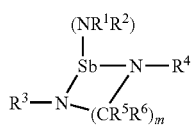

can for example be synthesized according to the following reaction scheme (A):

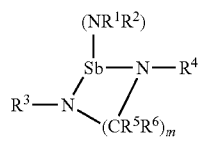

and the antimony precursor of the general formula (B):

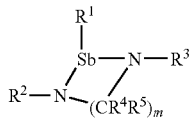

can be synthesized according to the following reaction scheme (B):

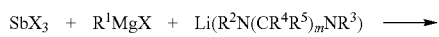

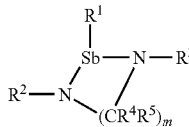

or by the following reaction scheme (C):

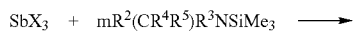

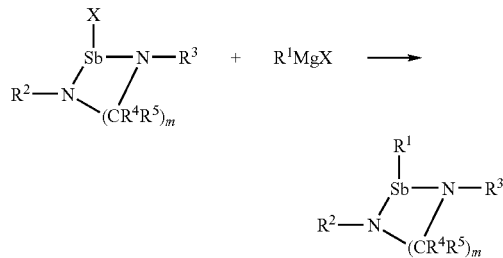

The antimony precursor of the general formula (C) can be formed by synthesis in a corresponding manner.

The antimony precursor of the general formula (D), having the following structure:

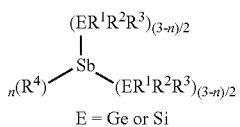

can for example be synthesized according to the following reaction schemes (D), when n is zero, or (E), when n is 2:

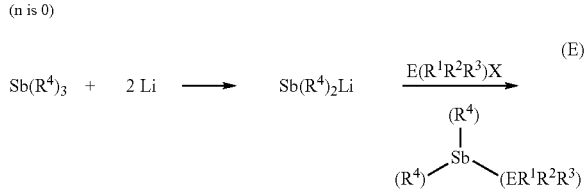

wherein X is halo (fluorine, bromine, chlorine, iodine).

In the foregoing synthetic examples, RMgX and RLi can be used as alternative synthesis reagents.

As specific examples illustrative of precursors of the invention, the precursors $Sb(NMeEt)_3$, $Sb(CH=CMe_2)_3$, $Sb(CH_2CH=CH_2)_3$ and $Sb(NMe_2)_3$ were synthesized and characterized. The precursors $Sb(NMe_2)_3$ and $Sb(NMeEt)_3$ were determined to exhibit photo-sensitivity and therefore to require storage in a container protected from light exposure or in other photo-resistant packaging, to avoid light-induced decomposition thereof. Similar considerations are applicable to $Sb(CH=CMe_2)_3$ and $Sb(CH_2CH=CH_2)_3$.

FIG. 1 shows the nuclear magnetic resonance spectrum of $Sb(NMeEt)_3$ and FIG. 2 shows the nuclear magnetic resonance spectrum of $Sb(NMe_2)_3$.

FIG. 3 is a simultaneous thermal analysis (STA) graph for these two precursors, $Sb(NMeEt)_3$ and $Sb(NMe_2)_3$, in which percentage thermogravimetry (TG) is plotted as a function of temperature, in degrees Centigrade.

III. Tellurium Precursors

The following are representative tellurium precursors that can be used in the methods described herein:

wherein:
$R_1$ and $R_2$ may be the same as or different from one another, and are independently selected from among H, $C_1$-$C_6$ alkyl, $C_5$-$C_{10}$ cycloalkyl, $C_6$-$C_{10}$ aryl, and —$Si(R^3)_3$ wherein each $R^3$ is independently selected from $C_1$-$C_6$ alkyl;

wherein:
$R_1$, $R_2$ and $R_3$ may be the same as or different from one another, and are independently selected from among H, $C_1$-$C_6$ alkyl, $C_5$-$C_{10}$ cycloalkyl, $C_6$-$C_{10}$ aryl, and —Si$(R_3)_3$ wherein each $R_3$ is independently selected from $C_1$-$C_6$ alkyl;

wherein:
$R_1$ and $R_2$ may be the same as or different from one another, and are independently selected from among H, $C_1$-$C_6$ alkyl, $C_5$-$C_{10}$ cycloalkyl, $C_6$-$C_{10}$ aryl, and —Si$(R^3)_3$ wherein each $R^3$ is independently selected from $C_1$-$C_6$ alkyl;

Other tellurium complexes include those with beta-diketiminate ligands, which overcome the problems that many tellurium precursors used in deposition applications are very oxygen-sensitive and light-sensitive, and have an unpleasant odor. By base stabilization with beta-diketiminate ligands, a tellurium precursor is obtained of a highly stable character with improved handling and shelf life characteristics, reduced odor, and sufficient volatility for deposition applications.

The tellurium diketiminate complexes described herein can be used for CVD/ALD to form Te or Te-containing films. These compounds can be used in combination with Ge- and/or Sb-compounds to produce Te—Ge—, Te—Sb— or Ge—Sb—Te films in varied compositions. A general procedure to synthesize diketiminate ligands has been described in the literature, but such procedure is disadvantageous, since very bulky aryl substituents on the coordinating nitrogen atoms are required.

In contrast, we have discovered that smaller alkyl ligands as iso-propyl, n-butyl, tert-butyl or amine-substituted alkyl groups, as for example ethylene-dimethylamine, can be advantageously used to produce superior tellurium diketiminate precursors for CVD/ALD applications. Smaller substituents on the nitrogen donor atoms provide sufficient volatility to form good films at low temperature.

The ligands L can be used as the lithium salt or in a free imine form to synthesize the desired Te complexes. The lithium salt of the ligand can be reacted with TeX$_4$ (wherein X=Cl, Br, I) to generate LTeX$_3$ by salt elimination, which can then be reacted with either a lithium or a Grignard reagent to produce LTeR$_3$ (wherein R=alkyl, aryl, amide, silyl).

Alternatively the free imine form of the ligand L can be reacted with a tellurium organic compound such as TeMe$_4$ to produce the desired Te species LTeMe$_3$ by methane elimination. The diketiminate ligands provide very effective base stabilization of the reactive metal center tellurium. The invention therefore provides a new class of Te complexes that provide greater stability and shelf life, while retaining sufficient volatility to form superior Te films via CVD/ALD at low temperatures.

Additional tellurium complexes which can be used have the formulae (I) and (II):

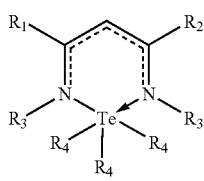

(I)

wherein R$_1$, R$_2$ and R$_3$ they be the same as or different from one another, and each is independently selected from C$_1$-C$_6$ alkyl, C$_6$-C$_{10}$ aryl, silyl and C$_1$-C$_{12}$ alkylamine (which includes both monoalkylamine as well as dialkylamine); and

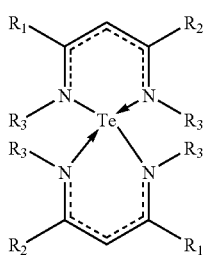

(II)

wherein R$_1$, R$_2$ and R$_3$ they be the same as or different from one another, and each is independently selected from C$_1$-C$_6$ alkyl, C$_6$-C$_{10}$ aryl, silyl and C$_1$-C$_{12}$ alkylamine (which includes both monoalkylamine as well as dialkylamine).

The beta-diketiminate ligands may for example be synthesized by the following procedure:

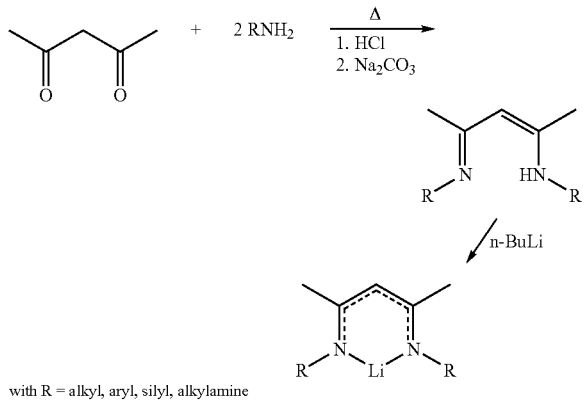

with R = alkyl, aryl, silyl, alkylamine

The tellurium complexes then can be synthesized by the following reaction:

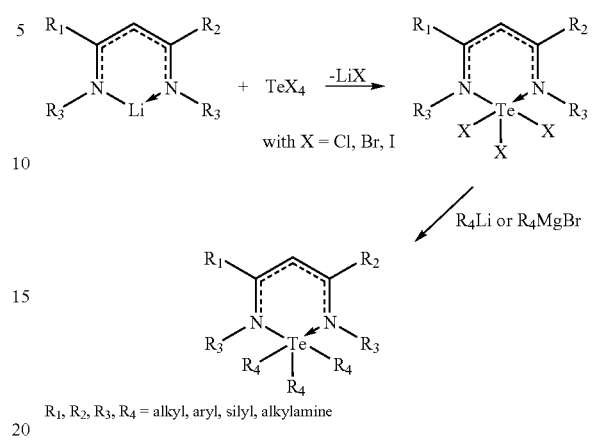

R$_1$, R$_2$, R$_3$, R$_4$ = alkyl, aryl, silyl, alkylamine or alternatively by the following synthesis reaction:

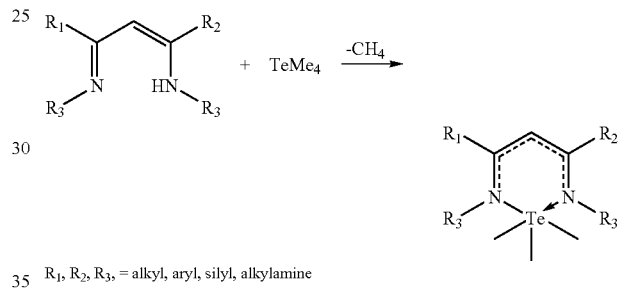

R$_1$, R$_2$, R$_3$, = alkyl, aryl, silyl, alkylamine or by the following synthesis reaction:

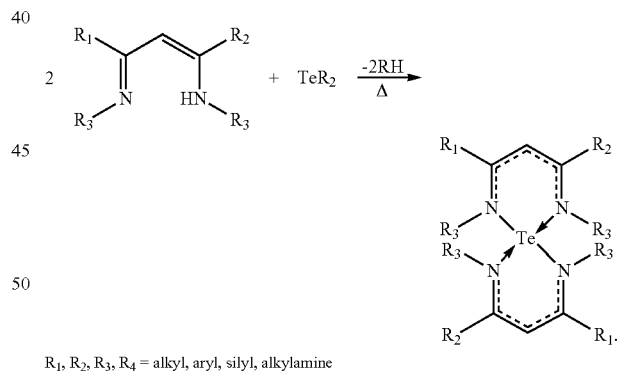

R$_1$, R$_2$, R$_3$, R$_4$ = alkyl, aryl, silyl, alkylamine

The tellurium complexes described herein can be employed as CVD/ALD precursors for deposition of tellurium-containing thin films, e.g., by liquid injection of neat precursor material, or in organic solvent or by direct evaporation.

IV. Film Formation

The precursors described herein can be used to form amorphous germanium-containing films, as well as crystalline germanium-containing films, depending on the process conditions, deposition chamber configuration, substrate composition, etc. The determination of these process variables can readily be made by those of ordinary skill in the art, without undue experimentation, based on the disclosure herein and appropriate empirical effort involving varying process conditions and characterizing the resulting films, to establish a process condition envelope appropriate to a specific film-forming application.

The germanium compounds described herein may be used with appropriate co-reactants in a continuous deposition mode (CVD) or pulsed/atomic layer deposition mode (ALD) to deposit films of superior character. For oxides, preferred co-reactants include $O_2$ and $N_2O$ for CVD, and more aggressive oxidizers for pulsed deposition, e.g., $H_2O$, ozone, and $O_2$ plasma. For metal-like films, reducing atmospheres are advantageously used.

For CVD modes of film formation, reducing agents such as $H_2$, and $NH_3$ are preferred, and plasmas of these co-reactants may be used in digital or ALD mode, wherein the co-reactants are separated from the precursor in a pulse train, utilizing general CVD and ALD techniques within the skill of the art, based on the disclosure herein. More aggressive reducing agents can also be used in a digital or ALD mode since co-reactants can be separated, preventing gas phase reactions. For ALD and conformal coverage in high aspect ratio structures, the precursor preferably exhibits self-limiting behavior in one type of atmosphere (e.g., inert or weakly reducing/oxidizing gas environments) and exhibits rapid decomposition to form a desired film in another type of atmosphere (e.g., plasma, strongly reducing/oxidizing environments).

Analogous metal cation precursors can be advantageously employed for CVD; while dissimilar species (i.e., different ligand species) can be employed in pulsed deposition.

The precursors described herein can be utilized as low temperature deposition precursors with reducing co-reactants such as hydrogen, $H_2$/plasma, amines, imines, hydrazines, silanes, silyl chalcogenides such as $(Me_3Si)_2Te$, germanes such as $GeH_4$, ammonia, alkanes, alkenes and alkynes. Liquid delivery formulations can be employed in which precursors that are liquids may be used in neat liquid form, or liquid or solid precursors may be employed in suitable solvents, including for example alkane solvents (e.g., hexane, heptane, octane, and pentane), aryl solvents (e.g., benzene or toluene), amines (e.g., triethylamine, tert-butylamine), imines and hydrazines. The utility of specific solvent compositions for particular Ge precursors may be readily empirically determined, to select an appropriate single component or multiple component solvent medium for the liquid delivery vaporization and transport of the specific germanium precursor that is employed. In the case of solid precursors of the invention, a solid delivery system may be utilized, for example, using the ProE-Vap solid delivery and vaporizer unit (commercially available from ATMI, Inc., Danbury, Conn., USA).

In general, the thicknesses of metal-containing layers in the practice of the present invention can be of any suitable value. In a specific embodiment of the invention, the thickness of the metal-containing layer can be in a range of from 5 nm to 500 nm or more.

FIG. 1 is a schematic representation of a material storage and dispensing package 100 containing a germanium precursor, according to one embodiment of the present invention.

The material storage and dispensing package 100 includes a vessel 102 that may for example be of generally cylindrical shape as illustrated, defining an interior volume 104 therein. In this specific embodiment, the precursor is a solid at ambient temperature conditions, and such precursor may be supported on surfaces of the trays 106 disposed in the interior volume 104 of the vessel, with the trays having flow passage conduits 108 associated therewith, for flow of vapor upwardly in the vessel to the valve head assembly, for dispensing in use of the vessel.

The solid precursor can be coated on interior surfaces in the interior volume of the vessel, e.g., on the surfaces of the trays 106 and conduits 108. Such coating may be affected by introduction of the precursor into the vessel in a vapor form from which the solid precursor is condensed in a film on the surfaces in the vessel. Alternatively, the precursor solid may be dissolved or suspended in a solvent medium and deposited on surfaces in the interior volume of the vessel by solvent evaporation. In yet another method the precursor may be melted and poured onto the surfaces in the interior volume of the vessel. For such purpose, the vessel may contain substrate articles or elements that provide additional surface area in the vessel for support of the precursor film thereon.

As a still further alternative, the solid precursor may be provided in granular or finely divided form, which is poured into the vessel to be retained on the top supporting surfaces of the respective trays 106 therein.

The vessel 102 has a neck portion 109 to which is joined the valve head assembly 110. The valve head assembly is equipped with a hand wheel 112 in the embodiment shown. The valve head assembly 110 includes a dispensing port 114, which may be configured for coupling to a fitting or connection element to join flow circuitry to the vessel. Such flow circuitry is schematically represented by arrow A in FIG. 1, and the flow circuitry may be coupled to a downstream ALD or chemical vapor deposition chamber (not shown in FIG. 1).

In use, the vessel 102 is heated, such input of heat being schematically shown by the reference arrow Q, so that solid precursor in the vessel is at least partially volatilized to provide precursor vapor. The precursor vapor is discharged from the vessel through the valve passages in the valve head assembly 110 when the hand wheel 112 is translated to an open valve position, whereupon vapor deriving from the precursor is dispensed into the flow circuitry schematically indicated by arrow A.

In lieu of solid delivery of the precursor, the precursor may be provided in a solvent medium, forming a solution or suspension. Such precursor-containing solvent composition then may be delivered by liquid delivery and flash vaporized to produce a precursor vapor. The precursor vapor is contacted with a substrate under deposition conditions, to deposit the metal on the substrate as a film thereon.

In one embodiment, the precursor is dissolved in an ionic liquid medium, from which precursor vapor is withdrawn from the ionic liquid solution under dispensing conditions.

As a still further alternative, the precursor may be stored in an adsorbed state on a suitable solid-phase physical adsorbent storage medium in the interior volume of the vessel. In use, the precursor vapor is dispensed from the vessel under dispensing conditions involving desorption of the adsorbed precursor from the solid-phase physical adsorbent storage medium.

Supply vessels for precursor delivery may be of widely varying type, and may employ vessels such as those commercially available from ATMI, Inc. (Danbury, Conn.) under the trademarks SDS, SAGE, VAC, VACSorb, and ProE-Vap, as may be appropriate in a given storage and dispensing application for a particular precursor of the invention.

The precursors of the invention thus may be employed to form precursor vapor for contacting with a substrate to deposit a germanium-containing thin film thereon.

In a preferred aspect, the invention utilizes the precursors to conduct atomic layer deposition, yielding ALD films of superior conformality that are uniformly coated on the substrate with high step coverage and conformality even on high aspect ratio structures.

Accordingly, the precursors and processes described herein enable a wide variety of microelectronic devices, e.g., semiconductor products, flat panel displays, etc., to be fabricated with germanium-containing films of superior quality.

The precursor compounds and processes described herein can be used to form GST films in combination with any suitable germanium and antimony precursors, e.g., by CVD and ALD techniques, for applications such as PCRAM device manufacture. The process conditions useful for carrying out deposition of Sb-containing films can be readily determined within the skill of the art by the simple expedient of selectively varying the delivery and deposition process conditions and characterizing the resulting films, to determine the process conditions envelope most appropriate for a given deposition application.

In some embodiments, antimony-containing films are formed on substrates, and can be, for example, GST films, amorphous SbTe films, or crystalline SbTe films, and can be applied, for example, using atomic layer deposition (ALD) or chemical vapor deposition (CVD) techniques. Such SbTe (e.g. $Sb_2Te_3$) films may also be employed in thermoelectric devices.

In a further aspect of the invention, germanium butyl amidinate is employed, together with a tellurium precursor, e.g., a dialkyl tellurium precursor such as di-t-butyl tellurium, to yield amorphous GeTe by chemical vapor deposition or other suitable process. Amorphous films may be formed at any suitable process conditions. It will be recognized that the specific process conditions will be variable with respect to particular applications, and that varied types of deposition chambers may be employed in the formation of the amorphous GeTe film using the germanium butyl amidinate precursor of the invention. For example, vapor deposition of germanium from the germanium alkyl amidinate may be conducted at temperature in a range of from about 200° C. to about 400° C., and at pressure in a range of from about 0.1 to about 20 torr. In one illustrative embodiment, the amorphous GeTe is formed using germanium butyl amidinate and t-butyl tellurium at a temperature of 320° C. and 8 torr pressure, to form a GeTe film. In another illustrative embodiment, Ge butyl amidinate and t-butyl tellurium precursors are utilized at a temperature of 350° C. and 0.8 torr pressure, with an ammonia co-reactant, to form a GeTe film.

Deposition of Ge from Ge butyl amidinate is rapid at low temperature, with a deposition rate exceeding 50 Angstroms/minute. The GeTe deposition rate, when the Te precursor is delivered by bubbler technique, depends strongly on the Te bubbler carrier flow, with higher carrier flows yielding thicker GeTe films of higher Te content. Nonetheless, incorporation of Te requires a relatively high deposition temperature and pressure, which tends to result in the formation of crystalline GeTe. By appropriately controlling temperature and pressure, stoichiometric amorphous GeTe films can be attained, which remain relatively smooth after crystallization.

In various embodiments of the invention, smooth amorphous GeTe films can be formed using other dialkyl Te precursors, such as diisopropyl Te.

In general, increasing the deposition temperature improves Te deposition and reduction of deposition pressure avoids development of crystallinity, in the deposition of Ge from germanium butyl amidinate (GeBAMDN). In one preferred embodiment, GeTe films are formed by CVD from such Ge precursor, with ammonia used as a co-reactant and $Te(tBu)_2$ employed as the Te precursor. GeBAMDN permits increased deposition temperatures and reduced deposition pressures to be used to overcome the problem of producing crystalline GeTe, when such Ge precursor is used with a suitable Te precursor for co-deposition of tellurium, e.g., a dialkyl Te precursor such as $Te(tBu)_2$.

The effects of pressure and tellurium delivery on GeTe deposition using ammonia as a co-reactant, are shown by the data in Table 1 below. These data were generated in an experimental reactor system including an oil bath maintained at a temperature of 100° C., and a $Te(tBu)_2$ bubbler maintained at room temperature (~21° C.). The delivery rate of the germanium precursor, GeBAMDN, was 20 micromoles/minute, and the ammonia co-reactant flow was maintained at 200 standard cubic centimeters per minute. Pressure in the system was 800 millitorr (mtorr). Deposition times were fixed at 8 minutes, and the substrate was a 50 nanometers thick titanium nitride (TiN) coated silicon substrate.

TABLE 1

| Run # | Temp (° C.) | Bubbler carrier flow (sccm) | At % Ge | At % Te | Dep Rate (A/min) |
|---|---|---|---|---|---|
| 1170 | 350 | 25 | 81.4 | 18.3 | 34.4 |
| 1171 | 350 | 20 | 86.9 | 13.1 | 37.1 |
| 1173 | 350 | 15 | 88.1 | 11.6 | 29.4 |
| 1174 | 350 | 10 | 91.1 | 8.9 | 36.1 |
| 1167 | 320 | 35 | 86.5 | 13.4 | 25.8 |
| 1166 | 320 | 25 | 86.8 | 13.2 | 27.2 |
| 1168 | 280 | 35 | 90.8 | 9.0 | 30.5 |

The data in Table 1 show that high temperature improved tellurium incorporation in the resulting films, which were amorphous.

Table 2 below shows data for annealed GeTe films that were deposited at 8 Torr pressure after one hour annealing under nitrogen atmosphere at 400° C., as compared to the as-deposited film.

TABLE 2

|  | Film Thickness (A) | AT % GE | AT % TE |
|---|---|---|---|
| AS-DEPOSITED | 543.5 | 55.1 | 44.9 |
| 400° C., 1 HR ANNEAL UNDER $N_2$ | 501.6 | 55.8 | 44.2 |

The data in Table 2 show that the film thickness and compositional characteristics of the annealed and as-deposited GeTe material were consistent with one-another.

FIG. 2 is a scanning electron micrograph (SEM) of the annealed GeTe film, after annealing one hour under nitrogen atmosphere at 400° C., and FIG. 3 is a micrograph of the cross-section, in elevation, of the film, showing the $SiO_2$ substrate, TiN and GeTe layers. FIG. 3 shows that the film remained smooth after heat treatment.

Figure 4:
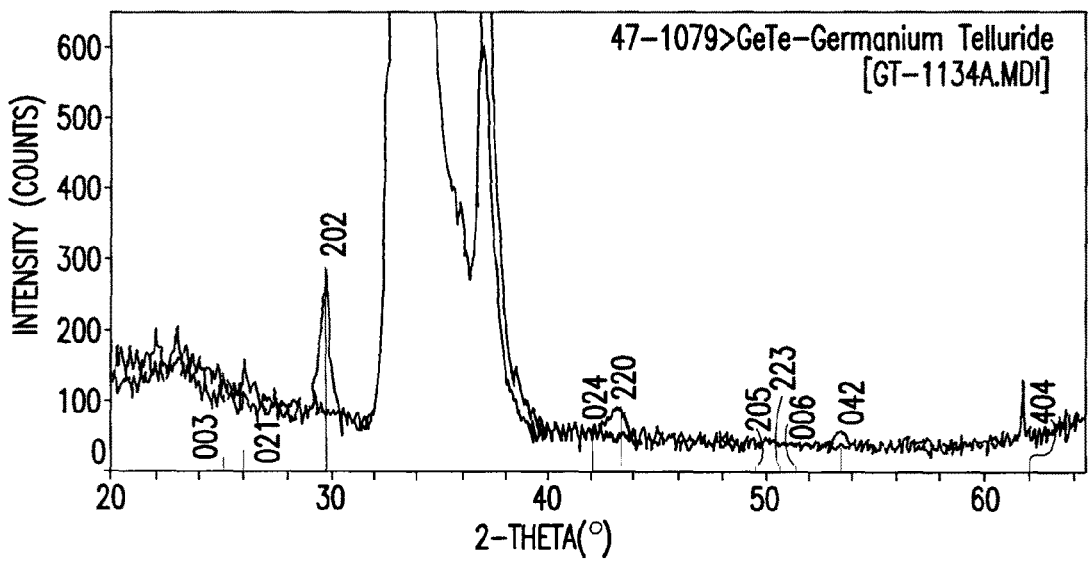
FIG. 4 is an x-ray dispersion (XRD) plot of a germanium telluride film, showing its crystalline character after annealing at 400° F.

FIG. 4 is an x-ray dispersion plot for the annealed GeTe film of Table 2, of crystalline character after 400° C. annealing.

The foregoing show that germanium butyl amidinate, GeBAMDN, yielded smooth amorphous GeTe at temperature less than 320° C., e.g., with an ammonia co-reactant, at 8 torr pressure.

These experiments also showed that GeTe deposition rate depended strongly on the Te bubbler carrier flow, with higher carrier flow yielding thicker GeTe films with nitrogen co-reactant, but thinner GeTe films and less tellurium incorporation with ammonia co-reactant.

Annealing at 400° C. in nitrogen crystallized the amorphous GeTe.

Next, deposition was carried out to determine the effects of temperature, pressure and tellurium delivery rate on GeTe deposition using nitrogen as a co-reactant.

The experimental system included an oil bath maintained at a temperature of 100° C. A tellurium (tBu)$_2$ bubbler maintained at room temperature (~21.5° C.) was employed and the Ge BAMDN precursor delivery rate was 20 micromoles/minute. Nitrogen co-reactant flow was 100 standard cubic centimeters per minute and pressure was fixed at 8,000 millitorr. Deposition times were 8 and 16 minutes. 50 nanometer thick TiN coated silicon substrates were used for the deposition. The data are set out in Table 3 below.

TABLE 3

| Run # | Temp (° C.) | Bubbler carrier flow (sccm) | Ge dep rate (A/min) | Te dep rate (A/min) | Crystallinity |
|---|---|---|---|---|---|
| 1127 | 320 | 10 | 11.8 | 12.0 | |
| 1128 | 320 | 25 | 54.4 | 57.8 | (003) |
| 1131 | 320 | 40 | 53.3 | 57.5 | |
| 1129 | 280 | 25 | 0 | 0 | |
| 1130 | 280 | 40 | 2.7 | 2.5 | |

Figure 5:
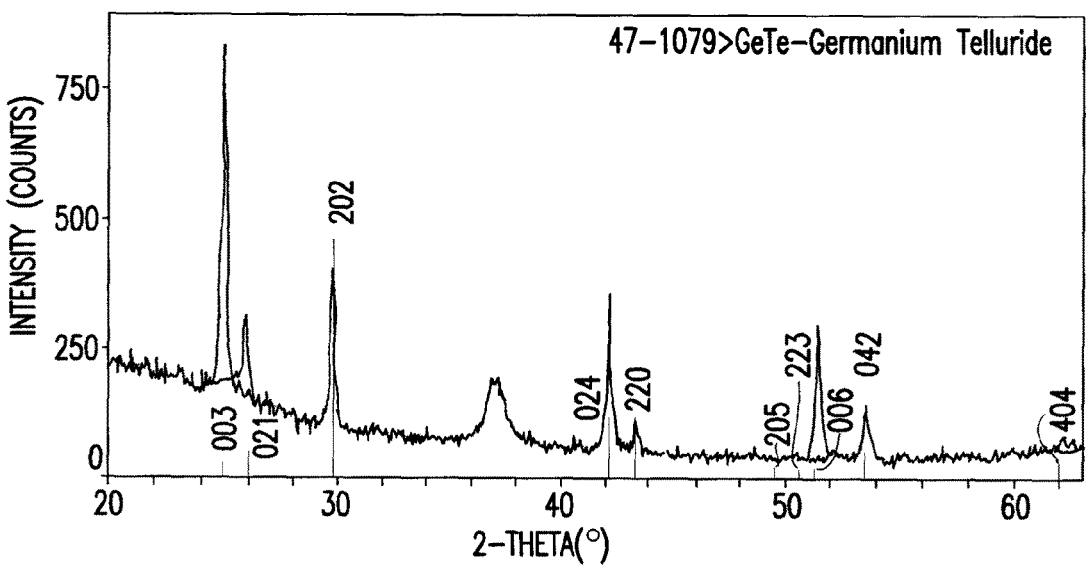
FIG. 5 is an XRD plot of a germanium telluride film deposited in a CVD process with a nitrogen co-reactant.

The data of Table 3 showed that high tellurium delivery rate improved GeTe deposition rate. No deposition occurred at 240° C. Deposition at 320° C. yielded GeTe with a main diffraction peak at (003), as shown in the x-ray dispersion plot of FIG. 5.

The effects of co-reactant on GeTe crystallinity are shown in Table 4 below, wherein deposition was carried out at a temperature of 320° C. and pressure of 8 torr, with Ge BAMDN delivery at a rate of 20 micromoles/minute and the tellurium bubbler carrier flow rate at 25 standard cubic centimeters per minute.

As shown in Table 4, only ammonia as a co-reactant yielded a smooth film, while the depositions using nitrogen and hydrogen as co-reactant species produced crystalline films.

TABLE 4

| Run # | Co-reactant | AT % Ge | AT % Te | Crystallinity |
|---|---|---|---|---|
| 1128 | N$_2$ | 48.3 | 51.3 | Crystalline |
| 1133 | H$_2$ | 48.4 | 51.2 | Crystalline |
| 1132 | NH$_3$ | 61.6 | 38.4 | Amorphous |

Figure 6:
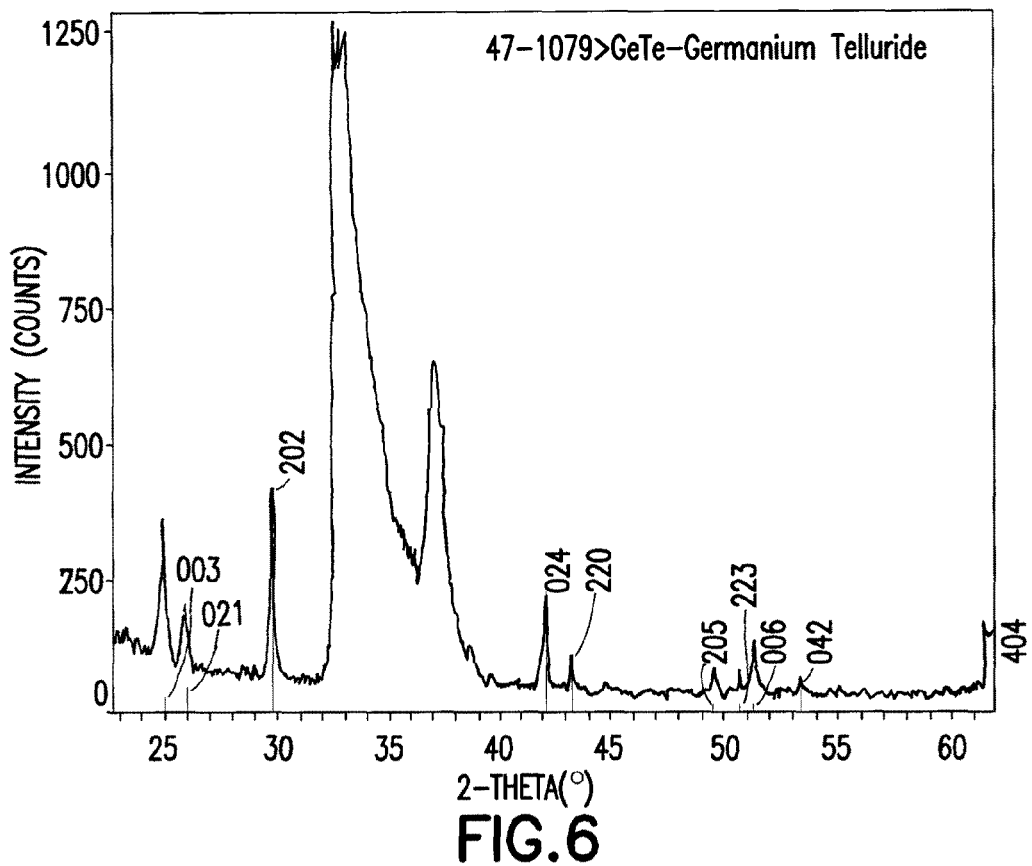
FIG. 6 is an XRD plot of a germanium telluride film deposited in a CVD process using a nitrogen co-reactant.
Figure 7:
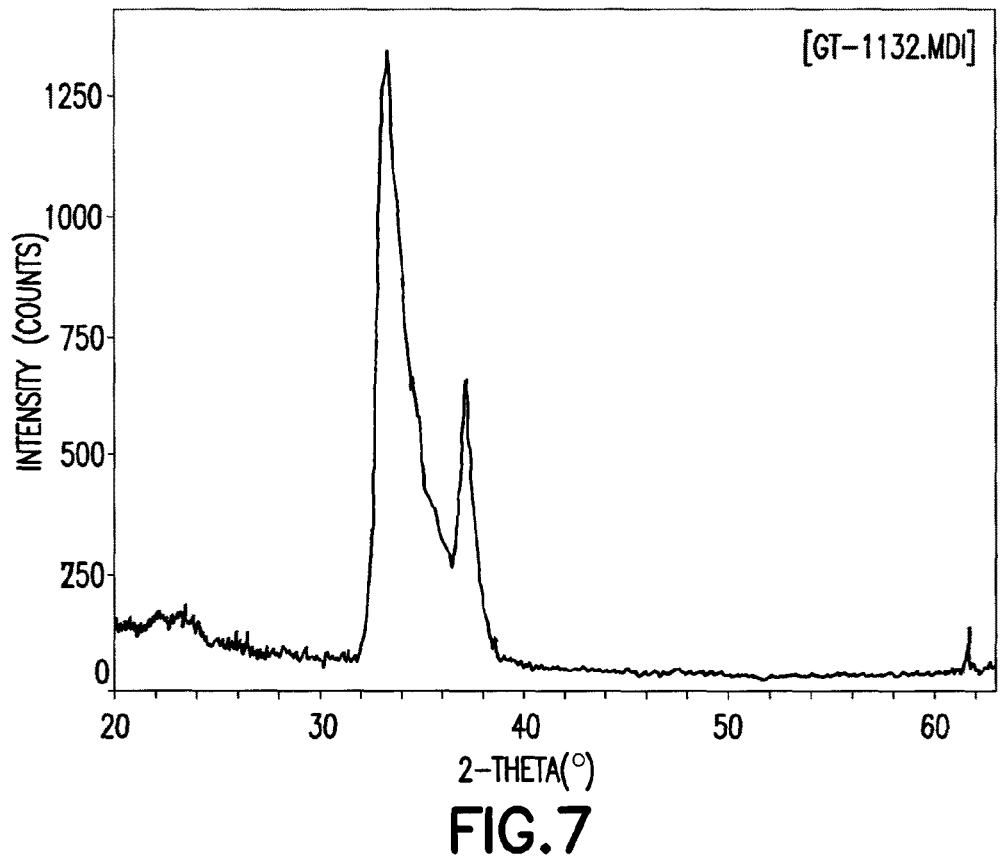
FIG. 7 an XRD plot of a germanium telluride film deposited in a CVD process using an ammonia co-reactant.

FIGS. 6 and 7 are x-ray dispersion plots for films produced in these depositions. The film whose plot is shown in FIG. 6 utilized nitrogen as the co-reactant and FIG. 7 is the plot for deposition using an ammonia co-reactant.

Figure 8:
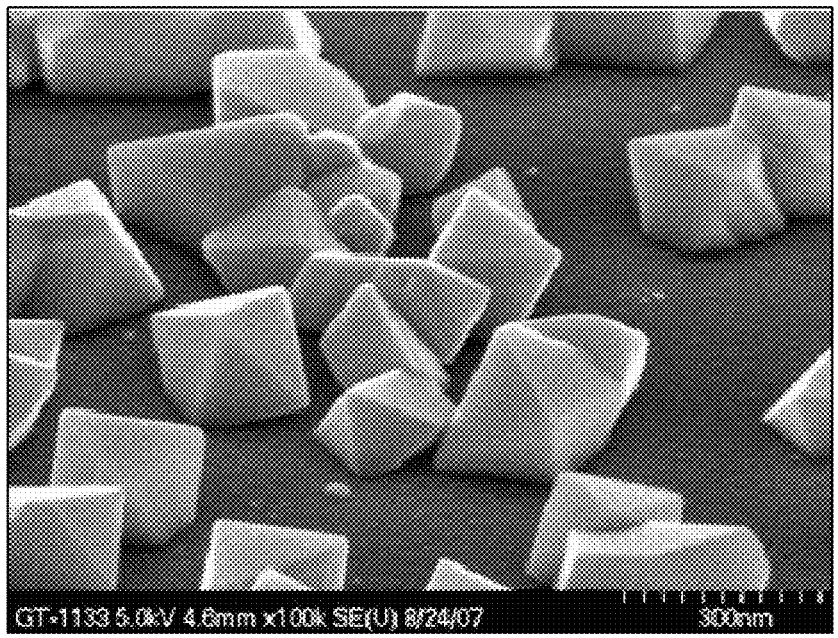
FIG. 8 is a scanning electron micrograph of a crystalline germanium telluride film formed deposited in a CVD process using hydrogen as a co-reactant.

FIG. 8 is a scanning electron micrograph of crystalline GeTe, formed using hydrogen as a co-reactant.

Figure 9:
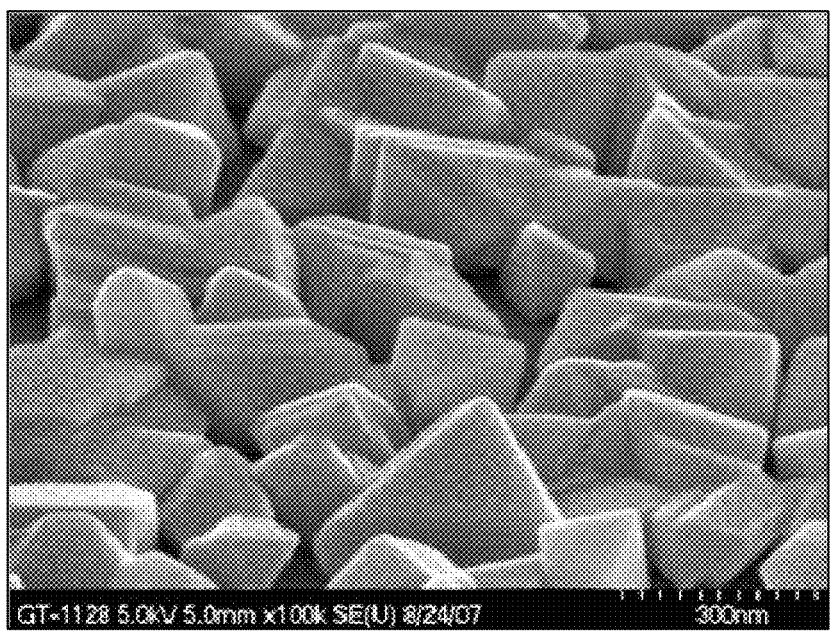
FIG. 9 is a scanning electron micrograph of a crystalline germanium telluride film formed in a CVD process using nitrogen as a co-reactant.

FIG. 9 is a scanning electron micrograph of the film produced using nitrogen as a co-reactant.

Figure 10:
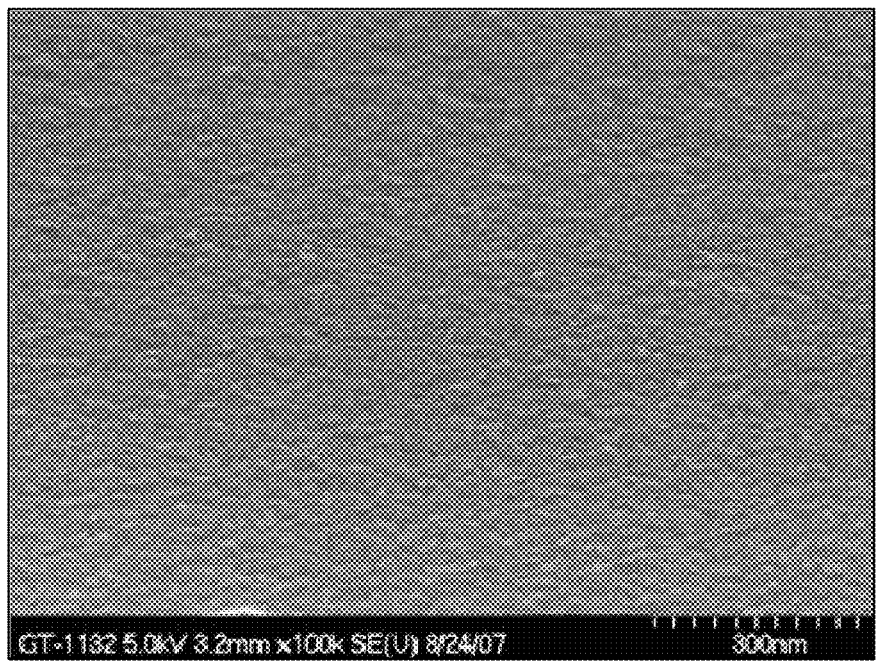
FIG. 10 is a scanning electron micrograph of an amorphous germanium telluride film formed on a 50 nanometer thickness of titanium nitride.

FIG. 10 is a scanning electron micrograph of amorphous GeTe produced at a film thickness of 25 nanometers on the top surface of a 50 nanometer thick layer of titanium nitride.

Figure 11:
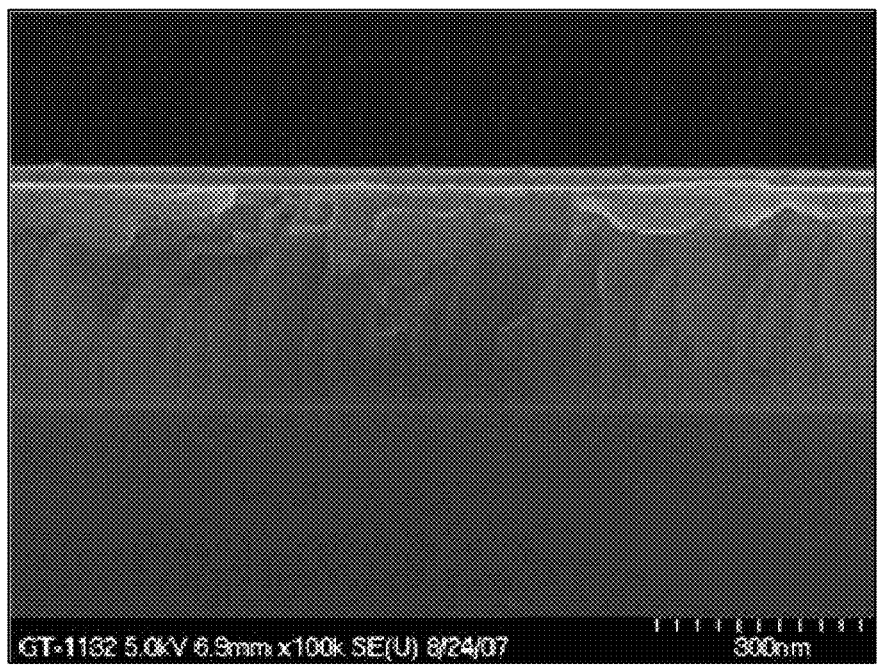
FIG. 11 is a cross-sectional elevation view of the germanium telluride film of FIG. 10.

FIG. 11 shows an elevation section of the smooth amorphous GeTe film of FIG. 10.

Figure 12:
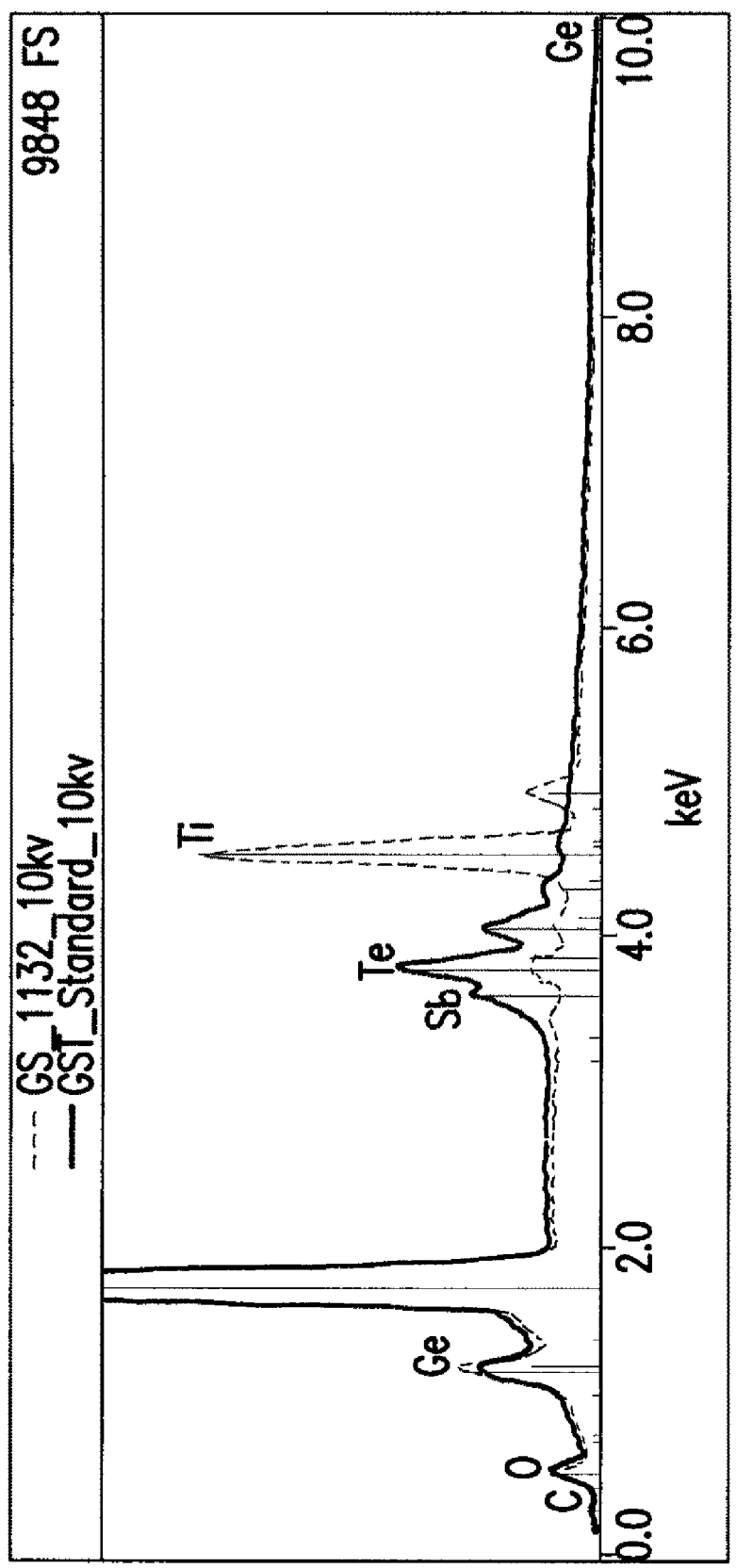
FIG. 12 is an EDS spectra plot of germanium telluride and a standard GST film.

FIG. 12 is an energy dispersive spectrometry (EDS) spectrum of the GeTe film shown in FIGS. 10 and 11, against a 50 nanometer thick GST film as a standard.

Set out in Table 5 below is a quantitative EDS analysis using the GST sample, Ge$_2$Sb$_2$Te$_5$, as a standard.

TABLE 5

| | Ge | | Sb | | Te | |
|---|---|---|---|---|---|---|
| Sample | % Wt | Atomic % | % Wt | Atomic % | % Wt | Atomic % |
| GST_standard | 13.99 | 22.00 | 23.45 | 22.00 | 62.57 | 56.00 |
| GT_1132 | 17.71 | 61.64 | 0 | 0 | 19.38 | 38.37 |

For creation of the Ge$_2$Sb$_2$Te$_5$ standard file, it was assumed that germanium (Ge), antimony (Sb), and tellurium (Te) were the only elements present, and that their respect weight percentages were 13.99, 23.45 and 62.57. In actuality, silicon, carbon and oxygen were also present, but their peaks did not overlap with the elements of interest, and thus were considered non-interfering in the determination of germanium, antimony and tellurium in the GST sample.

Figure 13:
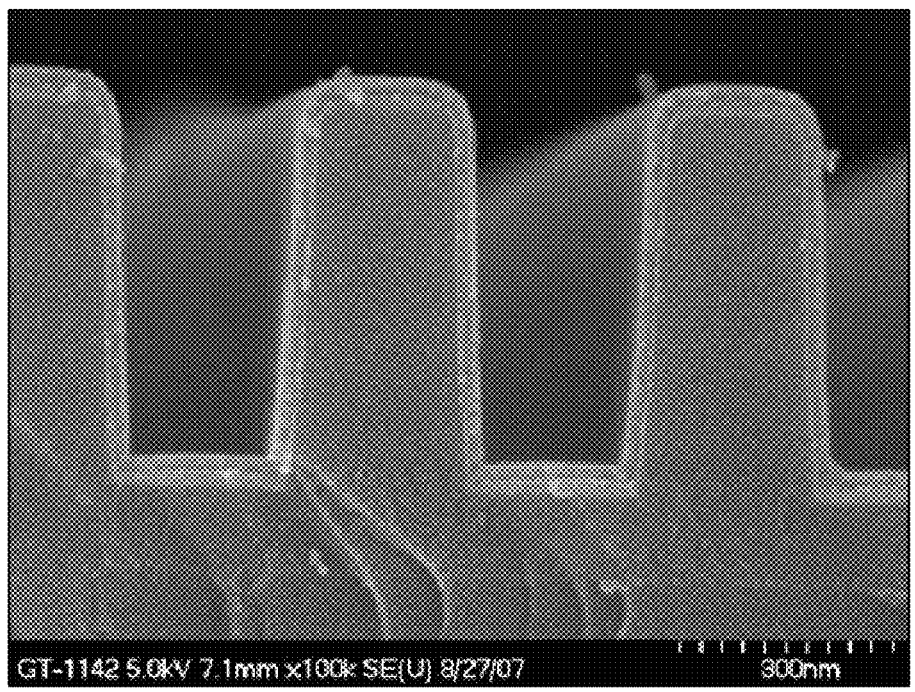
FIG. 13 is a scanning electron micrograph of a film of germanium telluride deposited on a microelectronic device structure.

FIG. 13 is a scanning electron micrograph of GeTe on a microelectronic device structure, at an estimated thickness of about 300 Angstroms, and a composition of 68.4% germanium and 31.4% tellurium as determined analytically.

Table 6 shows data on the effects of temperature on tellurium incorporation for GeTe deposition with ammonia co-reactant. The data included temperature, deposition rate, percent germanium, percent tellurium and crystallinity of the product film.

TABLE 6

| Run # | Temperature (C.) | Dep rate (A/min) | AT % Ge | AT % Te | Crystallinity |
|---|---|---|---|---|---|
| 1137 | 340 | 61.2 | 44.7 | 54.9 | crystalline |
| 1136 | 320 | 29.2 | 60.3 | 39.5 | amorphous |
| 1143 | 300 | 26.4 | 75.6 | 24.4 | amorphous |
| 1138 | 280 | 24.5 | 83.3 | 26.6 | amorphous |
| 1139 | 260 | 23.0 | 87.20 | 12.6 | amorphous |

These data in Table 6 show that the efficiency of tellurium incorporation decreases at low temperatures, falling to 16.6% tellurium in films produced at 280° C. and to only 12.6% tellurium in films produced at 260° C. Amorphous GeTe was produced at temperatures less than 340° C.

Figure 14:
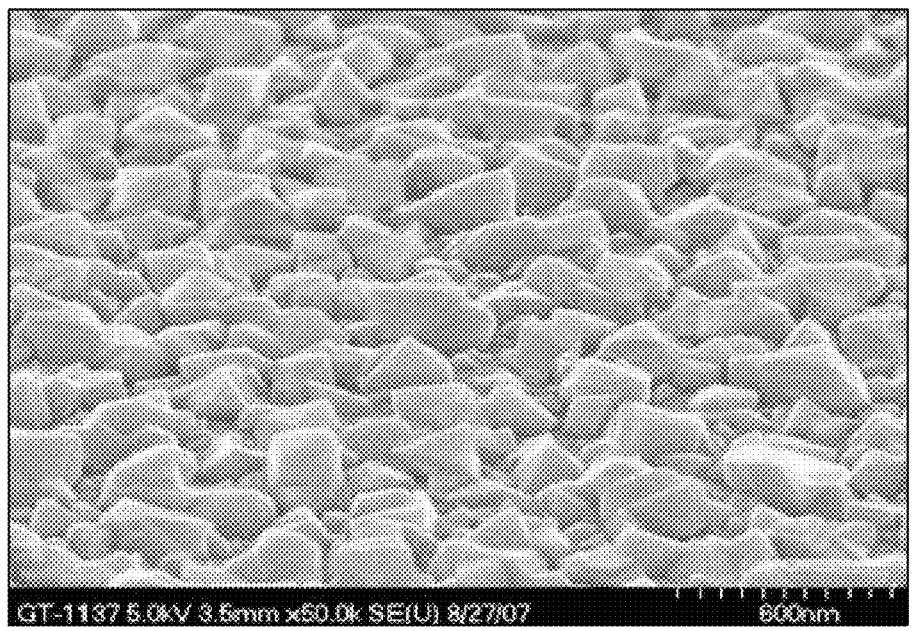
FIG. 14 is a scanning electron micrograph of a crystalline germanium telluride film, deposited at 340° C.
Figure 15:
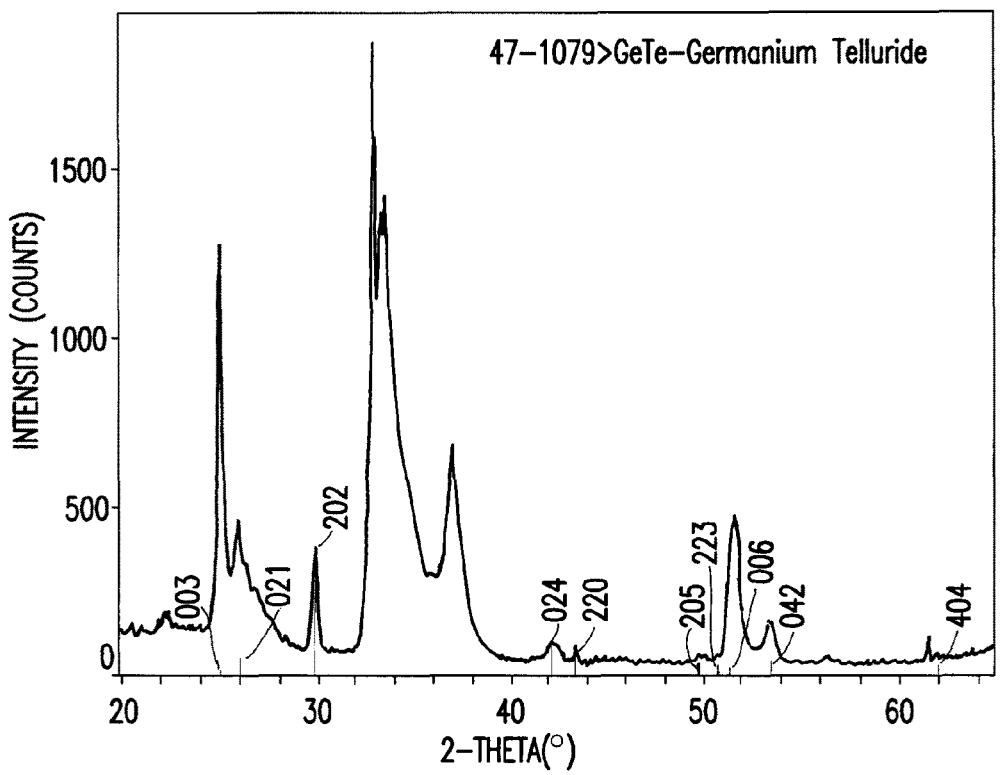
FIG. 15 is an XRD plot for the germanium telluride film of FIG. 14.

FIG. 14 is a scanning electron micrograph of a GeTe film deposited at 340° C., showing the crystalline character thereof, which is also reflected in the XRD plot of FIG. 15 for such film.

Table 7 shows data for annealing of amorphous germanium telluride films, as formed at 320° C. and pressure of 8 torr, during a 16 minute deposition. Annealing was carried out in a tube furnace under a nitrogen atmosphere for a time of 10 minutes, at a temperature of 350° C. which then was increased to 400° C. Annealing reduced the atomic percent of tellurium in the film and the film thickness.

TABLE 7

| | Thickness (A) | At % Ge | At % Te | Crystallinity |
|---|---|---|---|---|
| As-deposited | | | | amorphous |
| 350° C., 10 min | | | | |
| 400 ° C., 10 min | 436.3 | 53.1 | 46.4 | Crystalline |

The data in Table 7 show that the as-deposited film was amorphous and that annealing for 10 minutes at 400° C. induced crystallization of the film.

Figure 16:
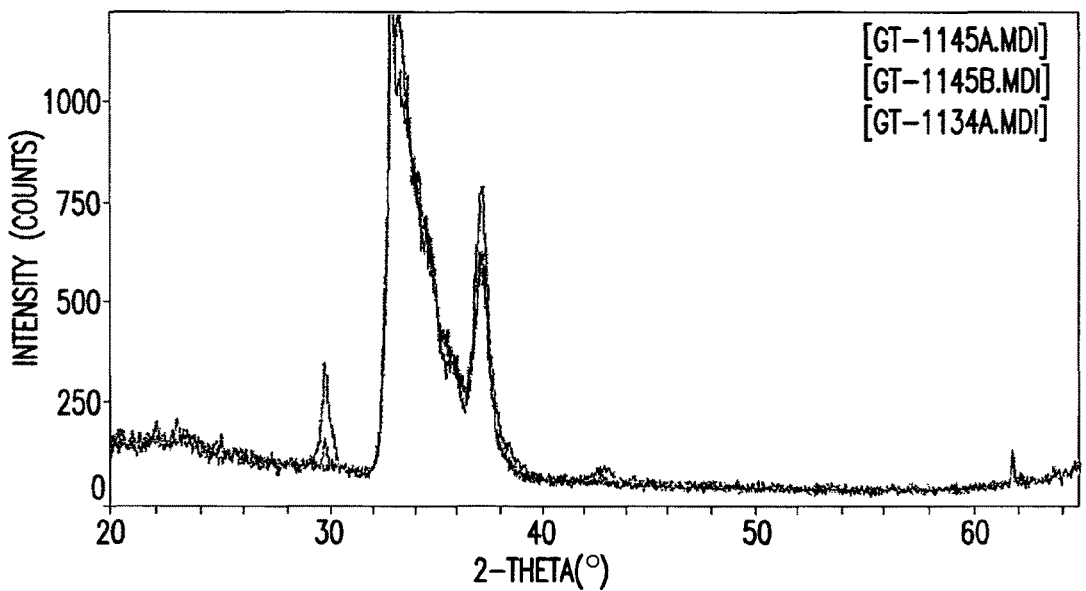
FIG. 16 is an XRD plot for various germanium telluride films, including an amorphous film, a film annealed at 350° C. for 10 minutes, and a germanium telluride film annealed at 350° C. followed by 400° C. exposure, for 10 minutes.

FIG. 16 is an x-ray dispersion plot of the 3 films for which data are shown in Table 7. The curve for the amorphous film is identified as that of sample GT-1134A. The sample subjected to 350° C. annealing for 10 minutes was sample GT-1145A. The sample subjected to 350° C. followed by 400° C. annealing, with an annealing duration of 10 minutes, was identified as sample G-1145B. The data show that the (202) peak at 2θ=30° increased after annealing.

Figure 17:
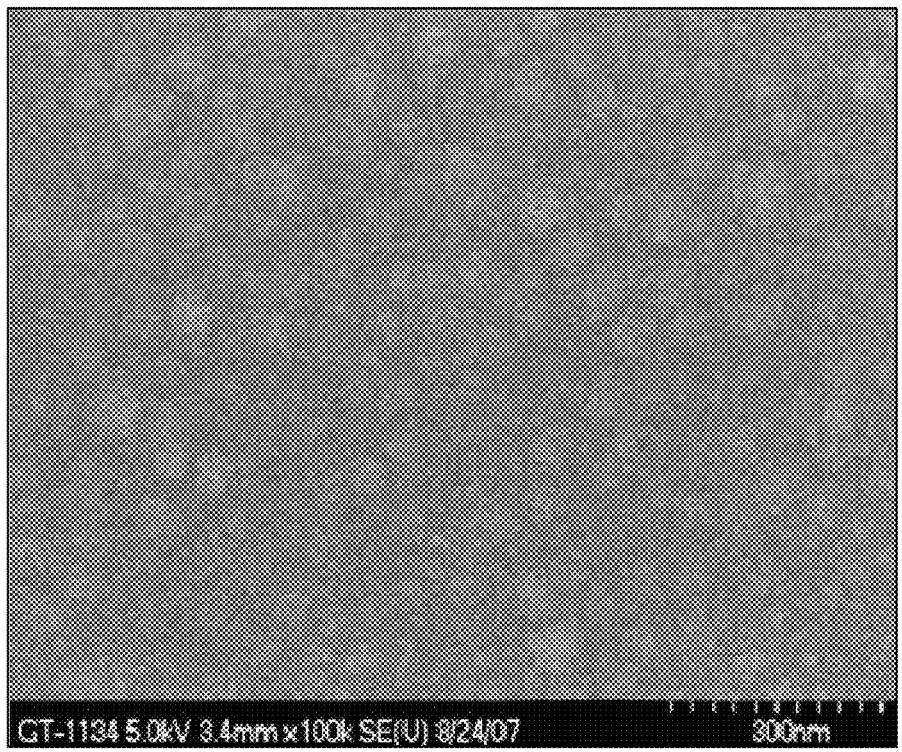
FIG. 17 is a scanning electron micrograph of an amorphous germanium telluride film.
Figure 18:
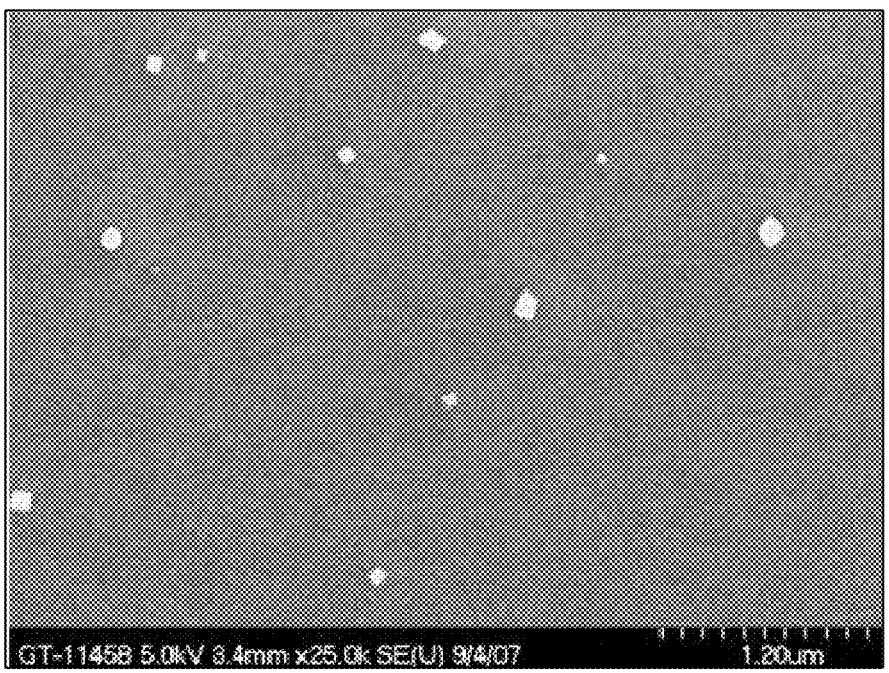
FIG. 18 is a scanning electron micrograph of a germanium telluride film, after 400° C. annealing.

FIG. 17 is a scanning electron micrograph of sample GT-1134, the amorphous GeTe film, and FIG. 18 is the scanning electron micrograph of the film annealed at 350° C. followed by 400° C. annealing, sample GT-1145B, showing tiny crystalline particles about 100 nanometers in size on top of the smooth film.

The effects of tellurium delivery rate on GeTe deposition at 300° C. are shown in Table 8 below, for a run carried out with tellurium carrier flow at 25 standard cubic centimeters per minute and a deposition rate of 26.4 Angstroms per minute (run #1143) and a run conducted at a tellurium carrier flow rate of 40 standard cubic centimeters per minute and deposition rate of 23.0 Angstroms per minute (run #1144). The data show that increasing the tellurium bubbler carrier flow reduces the germanium telluride deposition rate and tellurium incorporation.

TABLE 8

| Run # | Te carrier flow (sccm) | Deposition rate (A/min) | AT % Ge | AT % Te |
|---|---|---|---|---|
| 1143 | 25 | 26.4 | 75.6 | 24.4 |
| 1144 | 40 | 23.0 | 68.7 | 31.2 |

Table 9 below shows data reflecting the effects of tellurium delivery rate on germanium telluride deposition at 280° C. in 3 respective runs conducted at 280° C., a pressure of 8 torr and with ammonium as a co-reactant. The tellurium carrier flow was 25 sccm in the first run, 40 sccm in the second run and 50 sccm in the third run, which produced deposition rates of 24.5, 28.5 and 24.2 Angstroms per minute, respectively. The data show that increasing the tellurium bubbler carrier flow from 40 to 50 sccm reduces the tellurium incorporation and the GeTe deposition rate.

TABLE 9

| Run # | Te carrier flow (sccm) | Deposition rate (A/min) | AT % Ge | AT % Te |
|---|---|---|---|---|
| 1138 | 25 | 24.5 | 83.3 | 16.6 |
| 1140 | 40 | 28.5 | 72.9 | 26.9 |
| 1141 | 50 | 24.2 | 78.3 | 21.5 |

Thus, the present invention enables the production of highly conformal GST films by the formation of smooth amorphous GeTe at suitable temperature and pressure process conditions. By controlling temperature and pressure, amorphous germanium telluride films are produced, which remain relatively smooth after crystallization. While demonstrated for germanium butyl amidinate, Ge BAMDN and t-butyl tellurium, $Te(tBu)_2$, the germanium precursor can also be used with other dialkyl tellurium precursors, e.g., $TeR_2$ wherein R is $C_3$-$C_8$. Diisopropyl tellurium is a suitable alternative dialkyl tellurium precursor to di-tert-butyl tellurium as a Te source reagent. The germanium precursor can advantageously be [{nBuC(iPrN)$_2$}$_2$Ge].

The invention therefore contemplates the use of [{nBuC(iPrN)$_2$}$_2$Ge] as a precursor for deposition of amorphous smooth germanium telluride films, with ammonia being useful as a co-reactant in the deposition process at higher temperatures and lower pressures.

Figure 19:
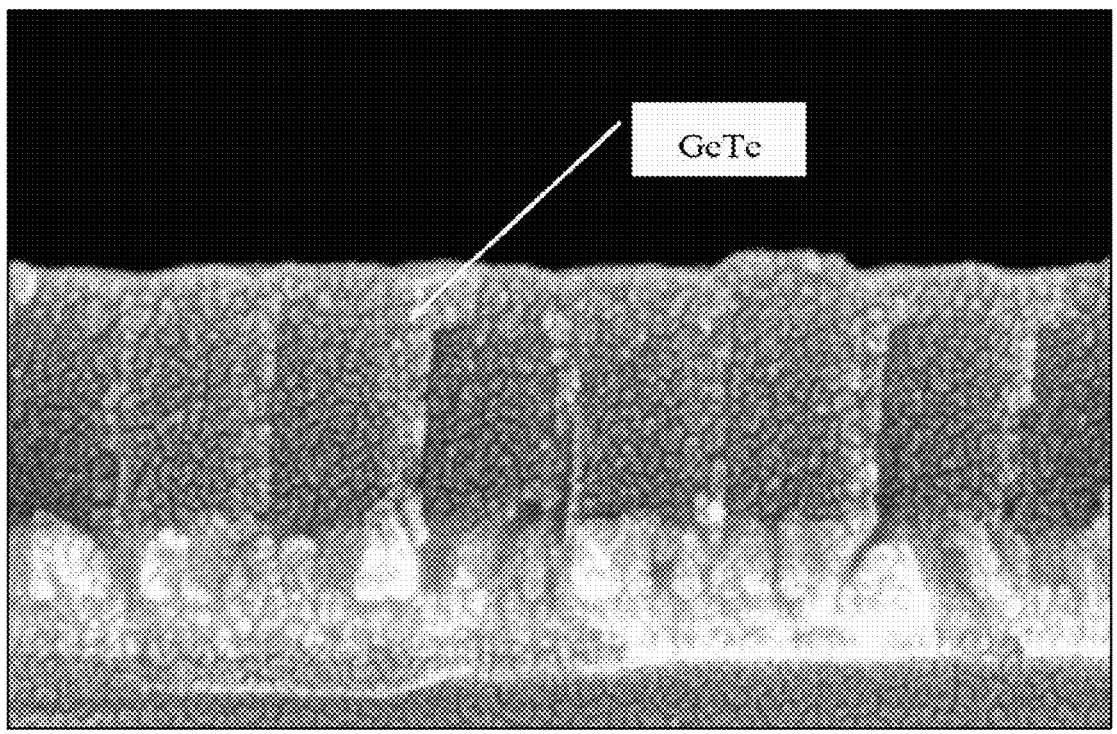
FIG. 19 is a scanning electron micrograph of a microelectronic device structure, as an example of an "aggressive" substrate on which GeTe has been deposited by chemical vapor deposition, using a germanium butyl amidinate precursor and a dialkyl tellurium precursor.

FIG. 19 is a scanning electron micrograph of a microelectronic device structure, as an example of an "aggressive" substrate on which GeTe has been deposited by chemical vapor deposition, using a germanium butyl amidinate precursor and a dialkyl tellurium precursor. The character of the GeTe material enables phase change random access memory (PCRAM) memory devices to be formed using amorphous germanium telluride films produced by use of the Ge BAMDN precursor of the invention.

By way of illustrative example, the GeTe film can be formed at temperature of 320° C., pressure of 7 torr, 5 micromoles/minute of GeBAMDN, 20 sccm carrier flow through a $Te(tBu)_2$ bubbler, and 50 sccm of ammonia. In general, advantageous process conditions may involve temperature in a range of from about 280 to about 350° C., flow of 1-10 micromoles/minute of Ge, 1-100 sccm carrier flow, 1-1000 sccm $NH_3$ and pressure in a range of 1-20 torr.

It will be appreciated that the process conditions involved in forming smooth amorphous films of germanium telluride using the [{nBuC(iPrN)$_2$}$_2$Ge] precursor of the invention may be widely varied in practice, and specific process conditions for forming such amorphous GeTe films can be readily determined by those skilled in the art, without undue experimentation, based on the disclosure herein.

Pre-Reaction Control

The invention in another aspect involves use of control agents to combat vapor phase pre-reaction of the precursors described herein, that otherwise causes uneven nucleation on the substrate, longer incubation times for deposition reactions, and lower quality product films. Such pre-reaction may for example be particularly problematic in applications involving chalcogenide films, related source materials (O, S, Se, Te, Ge, Sb, Bi, etc.), and/or manufacture of phase change memory and thermoelectric devices.

Pre-reaction may occur when the precursor reagents described herein are introduced to the deposition chamber, as in chemical vapor deposition, and may also occur in atomic layer deposition (ALD) processes, depending on the specific arrangement of ALD cycle steps and the specific reagents involved.

The invention therefore contemplates the use of control agents with precursors described herein, whereby detrimental gas phase pre-reactions are suppressed, mitigated or eliminated, so that deposition reactions are induced/enhanced on the substrate surface, and films of superior character are efficiently formed.

The control agents that can be utilized with precursors described herein for such purpose include agents selected from the group consisting of (i) heteroatom (O, N, S) organo Lewis base compounds, (ii) free radical inhibitors, and (iii) deuterium-containing reagents.

These agents can be utilized to lessen deleterious gas phase pre-reaction of the precursors described herein by various approaches, including:

(1) addition to the precursor composition of a pre-reaction suppressant comprising one or more heteroatom (O, N, S) organo Lewis base compounds such as 1,4-dioxane, thioxane, ethers, polyethers, triethylamine (TEA), triazine, diamines, N,N,N',N'-tetramethylethylenediamine, N,N,N'-trimethylethylenediamine, amines, imines, and pyridine;

(2) addition to the precursor composition of a free radical inhibitor, such as butylated hydroxy toluene (BHT), hydroquinone, butylated hydro anisole (BHA), diphenylamine, ethyl vanillin, etc.;

(3) use of modified chalcogenide precursors, in which hydrogen substituents have been replaced with deuterium (D) substituents, to provide deuterated analogs for vapor phase deposition; and (4) addition to the precursor composition of a deuterium source, to deuterate the precursor in situ.

The pre-reaction-combating agents described above (suppressants, free radical inhibitors, deuterium sources and/or deuterated precursors) can be introduced to any of the feed streams to the vapor deposition process in which the film is to be formed. For example, such pre-reaction-combating agents can be introduced to one or more of precursor feed stream(s), inert carrier gas stream(s) to which chalcogenide precursor(s) or other reagents are subsequently added for flow to the deposition chamber, co-reactant feed stream(s) flowed to the deposition chamber, and/or any other stream(s) that is/are flowed to the deposition chamber and in which the pre-reaction-combating agent(s) is/are useful for reduction or elimination of premature reaction of the precursors that would otherwise occur in the absence of such agent(s).

The aforementioned suppressants, free radical inhibitors and/or deuterium source reagents in specific embodiments are co-injected with the precursor(s), e.g., metal source reagent(s), to effect at least partial reduction of pre-reaction involving the precursor(s) and reagent(s).

The pre-reaction-combatting agent can alternatively be added directed to the deposition locus, e.g., the deposition chamber to which the precursor vapor is introduced for contacting with the substrate to deposit the film thereon, to suppress deleterious vapor phase pre-reaction involving the precursor(s) and/or other reagents.

As another approach, in the broad practice of the present invention, the suppressant, free radical inhibitor and/or deuterium source can be added to a solution containing the precursor and/or another metal source reagent, and the resulting solution can be utilized for liquid delivery processing, in which the solution is flowed to a vaporizer to form a source vapor for contacting with the substrate to deposit the deposition species thereon.

Alternatively, if the precursor and/or another metal source reagent are not in an existing solution, the suppressant, free radical inhibitor and/or deuterium source can be added to form a mixture or a solution with the precursor and/or another metal source reagent, depending on the respective phases of the materials involved, and their compatibility/solubility.

As a still further approach, the suppressant, free radical inhibitor and/or deuterium source can be utilized for surface treatment of the substrate prior to contacting of the substrate with the precursor and/or other metal source reagent.

The invention therefore contemplates various vapor deposition compositions and processes for forming films on substrates, in which pre-reaction of the precursors is at least partially attenuated by one or more pre-reaction-combating agents selected from among heteroatom (O, N, S) organo Lewis base compounds, sometimes herein referred to as suppressor agents, free radical inhibitors, and/or deuterium source reagents. Use of previously synthesized deuterated precursors or organometal compounds is also contemplated, as an alternative to in situ deuteration with a deuterium source. By suppressing precursor prereaction with these approaches, product films of superior character can be efficiently formed.

The control agent can be used for combating pre-reaction of chalcogenide precursor in a process in which multiple feed streams are flowed to a deposition locus to form a film on a substrate, wherein at least one of the multiple feed streams includes a precursor susceptible to pre-reaction adversely affecting the film, in which the method involves introducing the control agent to at least one of such multiple feed streams or supplied materials therefor, or to the deposition locus.

The pre-reaction combating reagent alternatively can be introduced to passivate the surface of a growing chalcogenide film or slow the deposition rate, followed by reactivation using an alternative precursor or co-reactant (for example $H_2$, $NH_3$, plasma, $H_2O$, hydrogen sulfide, hydrogen selenide, diorganotellurides, diorganosulfides, diorganoselenides, etc.), thereby carrying out passivation/retardation followed by reactivation steps, e.g., as an alternating repetitive sequence. Such sequence of passivation/retardation followed by reactivation can be carried out for as many repetitive cycles as desired, in ALD or ALD-like processes. The steps may be carried out for the entire deposition operation, or during some initial, intermediate or final portion thereof.

The invention therefore contemplates precursor compositions including the precursor and the pre-reaction-combating reagent. Within the categories of pre-reaction combating reagents previously described, viz., (i) heteroatom (O, N, S) organo Lewis base compounds, (ii) free radical inhibitors, and (iii) deuterium-containing reagents, suitable pre-reaction-combating reagents for specific applications may be readily determined within the skill of the art, based on the disclosure herein.

Heteroatom (O, N, S) organo Lewis base compounds may be of varied type, e.g., containing an oxo (—O—) moiety, a nitrogen ring atom or pendant amino or amide substituent, a sulfur ring atom or pendant sulfide, sulfonate or thio group, as effective to at least partially lessen pre-reaction of the precursor and other organo metal reagents in the process system. Illustrative examples of heteroatom (O, N, S) organo Lewis base compounds having utility in specific applications of the invention include, without limitation, 1,4-dioxane, thioxane, ethers, polyethers, triethylamine, triazine, diamines, N,N,N', N'-tetramethylethylenediamine, N,N,N'-trimethylethylenediamine, amines, imines, pyridine, and the like.

The heteroatom organo Lewis base compound in various specific embodiments of the invention may include a guanidinate compound, e.g., $(Me_2N)_2C=NH$.

One preferred class of heteroatom organo Lewis base compounds for such purpose includes $R_3N$, $R_2NH$, $RNH_2$, $R_2N(CH_2)_xNR_2$, $R_2NH(CH_2)_xNR_2$, $R_2N(CR_2)_xNR_2$, and cyclic amines —$N(CH_2)_x$—, imidazole, thiophene, pyrrole, thiazole, urea, oxazine, pyran, furan, indole, triazole, triazine, thiazoline, oxazole, dithiane, trithiane, crown ethers, 1,4,7-triazacyclononane, 1,5,9-triazacyclododecane, cyclen, succinamide, and substituted derivatives of the foregoing, wherein R can be hydrogen or any suitable organo moieties, e.g., hydrogen, $C_1$-$C_8$ alkyl, $C_1$-$C_8$ alkoxy, $C_1$-$C_8$ alkene, $C_1$-$C_8$ alkyne, and $C_1$-$C_8$ carboxyl, and wherein x is an integer having a value of from 1 to 6.

The heteroatom organo Lewis base compounds may be utilized in the precursor composition at any suitable concentration, as may be empirically determined by successive deposition runs in which the heteroatom organo Lewis base compound concentration is varied, and character of the resulting film is assessed, to determine an appropriate concentration. In various embodiments, the heteroatom organo Lewis base compound may be utilized in the concentration of 1-300% of the amount of precursor. Specific sub-ranges of concentration values within a range of 0.01-3 equivalents of the heteroatom organo Lewis base compound may be established for specific classes of precursors, without undue experimentation, based on the disclosure herein.

The pre-reaction-combating reagent may additionally or alternatively comprise free radical inhibitors that are effective to lessen the extent of pre-reaction between the precursor and another organo metal reagent. Such free radical inhibitors may be of any suitable type, and may for example include hindered phenols. Illustrative free radical inhibitors include, without limitation, free radical scavengers selected from the group consisting of: 2,6-ditert-butyl-4-methyl phenol, 2,2,6,6-tetramethyl-1-piperidinyloxy, 2,6-dimethylphenol, 2-tert-butyl-4-hydroxyanisole, 3-tert-butyl-4-hydroxyanisole, propyl ester 3,4,5-trihydroxy-benzoic acid, 2-(1,1-dimethylethyl)-1,4 benzenediol, diphenylpicrylhydrazyl, 4-tert-butylcatechol, N-methylaniline, 2,6-dimethylaniline, p-methoxydiphenylamine, diphenylamine, N,N'-diphenyl-p-phenylenediamine, p-hydroxydiphenylamine, phenol, octadecyl-3-(3,5-di-tert-butyl-4-hydroxyphenyl) propionate, tetrakis (methylene (3,5-di-tert-butyl-4-hydroxy-hydrocinnamate) methane, phenothiazines, alkylamidonoisoureas, thiodiethylene bis(3,5-di-tert-butyl-4-hydroxy-hydrocinnamate, 1,2-bis (3,5-di-tert-butyl-4-hydroxyhydrocinnamoyl) hydrazine, tris (2-methyl-4-hydroxy-5-tert-butylphenyl) butane, cyclic neopentanetetrayl bis (octadecyl phosphite), 4,4'-thiobis (6-tert-butyl-m-cresol, 2,2'-methylenebis (6-tert-butyl-p-cresol), oxalyl bis(benzylidenehydrazide) and mixtures thereof. Preferred free radical inhibitors include BHT, BHA, diphenylamine, ethyl vanillin, and the like.

Useful concentrations of the free radical inhibitor may be in a range of from 0.001 to about 0.10% by weight of the weight of the precursor, in various specific embodiments. More generally, any suitable amount of free radical inhibitor may be employed that is effective to combat the pre-reaction of the precursor in the delivery and deposition operations involved in the film formation process.

The deuterium source compounds afford another approach to suppressing pre-reaction of the chalcogenide precursor. Such deuterium source compounds may be of any suitable type, and may for example include deuterated pyridine, deuterated pyrimidine, deuterated indole, deuterated imidazole, deuterated amine and amide compounds, deuterated alkyl reagents, etc., as well as deuterated analogs of the precursors that would otherwise be used as containing hydrogen or protonic substituents.

Deuterides that may be useful in the general practice of invention as pre-reaction-combating reagents include, without limitation, germanium and antimony compounds of the formulae $R_xGeD_{4-x}$ and $R_xSbD_{3-x}$, wherein R can be hydrogen or any suitable organo moieties, e.g., hydrogen, $C_1$-$C_8$ alkyl, $C_1$-$C_8$ alkoxy, $C_1$-$C_8$ alkene, $C_1$-$C_8$ alkyne, and $C_1$-$C_8$ carboxyl, and wherein x is an integer having a value of from 1 to 6.

The deuterium source reagent may be utilized at any suitable concentration that is effective to combat pre-reaction of the precursor. Illustrative deuterium source reagent concentrations in specific embodiments of the invention can be in a range of 0.01 to about 5% by weight, based on the weight of precursor.

Thus, a deuterium source compound may be added to one or more of the feed streams to the vapor deposition process, and/or one of the precursors or other feed stream components may be deuterated in the first instance.

The concentrations of the pre-reaction-combating agents utilized in the practice of the present invention to at least partially eliminate pre-reaction of the precursors can be widely varied in the general practice of the present invention, depending on the temperatures, pressures, flow rates and specific compositions involved. The above-described ranges of concentration of the pre-reaction-combating reagents of the invention therefore are to be appreciated as being of an illustrative character only, with applicable concentrations being readily determinable within the skill of the art, based on the disclosure herein.

The specific mode of introduction or addition of the pre-reaction-combating agent to one or more of the feed streams to the deposition process may correspondingly be varied, and may for example employ mass flow controllers, flow control valves, metering injectors, or other flow control or modulating components in the flow circuitry joining the source of the pre-reaction-combating agent with the streams being flowed to the deposition process during normal film-forming operation. The process system may additionally include analyzers, monitors, controllers, instrumentation, etc., as may be necessary or appropriate to a given implementation of the invention.

In lieu of introduction or addition of the pre-reaction-combating agent to one or more of the flow streams to the vapor deposition process, the pre-reaction-combating agent may be mixed with precursor in the first instance, as a starting reagent material for the process. For example, the pre-reaction-combating agent may be mixed in liquid solution with the precursor, for liquid delivery of the resulting precursor solution to a vaporizer employed to generate precursor vapor for contact with the substrate to deposit the film thereon.

As mentioned, the pre-reaction-combating agent may be added to the deposition locus to provide active gas-phase suppression of pre-reaction of the precursor vapor(s) that would otherwise be susceptible to such deleterious interaction.

As a still further alternative, the pre-reaction-combating agent may be used as a preliminary surface treatment following which the precursor and co-reactants (e.g., $H_2$, $NH_3$, plasma, $H_2O$, hydrogen sulfide, hydrogen selenide, diorganotellurides, diorganosulfides, diorganoselenides, etc.) are delivered to the substrate surface to effect deposition on such surface. For such purpose, the pre-reaction-combating agent may be introduced into one of more of the flow lines to the deposition process and flow to the substrate in the deposition process chamber, prior to initiation of flow of any precursors. After the requisite period of contacting of the substrate with such pre-reaction-combating agent has been completed, the flow of the pre-reaction-combating agent can be terminated, and normal feeding of flow streams to the deposition chamber can be initiated.

It will be apparent from the foregoing description that the pre-reaction-combating agent may be introduced in any of a wide variety of ways to effect diminution of the pre-reaction of the precursor in the deposition system.

In one embodiment of the invention, a vapor phase deposition system is contemplated, comprising:

a vapor deposition chamber adapted to hold at least one substrate for deposition of a film thereon;

chemical reagent supply vessels containing reagents for forming the film;

first flow circuitry arranged to deliver said reagents from said chemical reagent supply vessels to the vapor deposition chamber;

a pre-reaction-combating agent supply vessel containing a pre-reaction-combating agent;

second flow circuitry arranged to deliver the pre-reaction-combating agent from the pre-reaction-combating agent supply vessel to the first flow circuitry, to said chemical reagent supply vessels and/or to the vapor deposition chamber.

Figure 20:
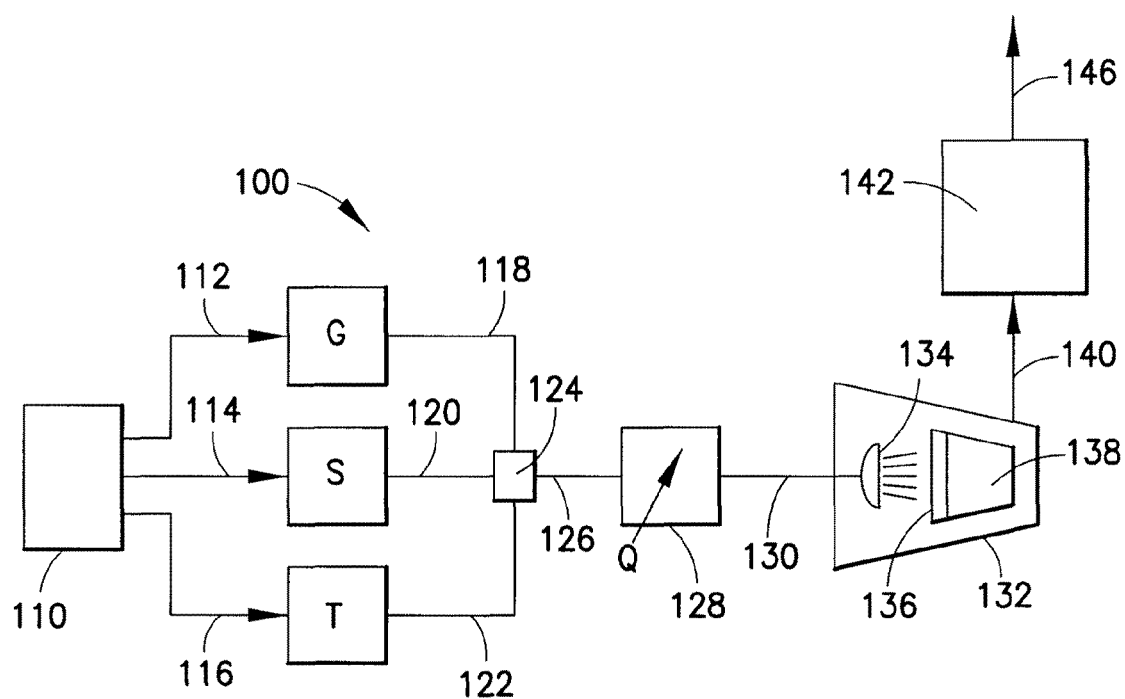
FIG. 20 is a schematic representation of a vapor deposition system according to one embodiment of the present invention, wherein suppression of pre-reaction of the precursors is achieved by addition of pre-reaction-combating reagent to one or more feed streams in the vapor deposition system.

Referring again to the drawings, FIG. 20 is a schematic representation of a vapor deposition system 100 in one embodiment thereof.

In this illustrative system, a pre-reaction-combating agent is contained in a supply vessel 110. The pre-reaction-combating agent can comprise a pre-reaction suppressant, a free radical inhibitor, a deuterium source, or a combination of two or more of such agents and/or types of such agents.

The pre-reaction-combating agent supply vessel is joined by respective flow lines 112, 114 and 116, to germanium, antimony and tellurium reagent supply vessels, labeled "G," "S" and "T," respectively. The germanium precursor in vessel "G" may be a tetraalkyl or tetraamido germanium compound, such as tetramethyl germanium, tetraethyl germanium, tetraallyl germanium, tetrakis(dimethylamino)germane or other organo germanium compounds. Furthermore, precursor "G" may be a germylene compound wherein the lone pair on Ge(II) can react in the gas-phase with chalcogen precursors in the absence of a pre-reaction suppressant. The antimony precursor in vessel "S" can be a trialkyl or triamido antimony compound, such as tributyl antimony, triisopropyl antimony, tris(dimethylamino)antimony or other organo antimony compound. The tellurium precursor in vessel "T" can be a dialkyl or diamido tellurium compound, such as diisopropyl tellurium, dibutyl tellurium, bis[bis(trimethylsilyl)amino]tellurium or other organo tellurium compound.

The pre-reaction-combating agent therefore can be added to any of the germanium, antimony and/or tellurium precursors in the respective "G," "S" and "T" vessels, via the corresponding flow line(s), which for such purpose may have flow control valves or other flow-modulating components therein.

In the specific process embodiment shown, the germanium, antimony and tellurium precursors are flowed in liquid form in feed lines 118, 120 and 122, respectively, to the mixing chamber 124, and the resulting precursor mixture then is flowed from the mixing chamber 124 in line 126 to vaporizer 128. In the vaporizer, the liquid precursor mixture and pre-reaction-combating agent are volatilized to form a precursor vapor. The precursor vapor then flows in line 130 to the showerhead disperser 134 in vapor deposition chamber 132, for discharge of precursor mixture onto the wafer substrate 136 mounted on susceptor 138 in the deposition chamber.

The precursor vapor contacting the wafer substrate 136 serves to deposit the germanium, antimony and tellurium metals on the substrate, to form a thin film of germanium-antimony-tellurium (GST) material, e.g., for manufacture of a phase change random access memory device.

The contacted precursor vapor, depleted in metals content, is discharged from the vapor deposition chamber 132 in line 140, and flows to the effluent abatement unit 142. In the effluent abatement unit 142, the discharged effluent vapor is treated, e.g., by scrubbing, catalytic oxidation, electrochemical treatment, or in other manner, to yield a final effluent that is discharged from the abatement unit in line 146.

It will be appreciated that the schematic representation of the vapor deposition system shown in FIG. 20 is of an illustrative character, and that numerous other arrangements could be utilized for deployment and use of the pre-reaction-combating agent, including those previously illustratively discussed herein. For example, the pre-reaction-combating agent could be introduced directly to the mixing chamber 124, for blending therein with the respective GST precursors. Alternatively, the pre-reaction-combating agent could be introduced into manifold 118, or other mixing chamber, blender, etc., for combination with the precursor that is being transported to the deposition locus.

The system shown in FIG. 20 employs liquid delivery of the respective precursors. It will be recognized that if solid-phased precursors are employed, then solid delivery techniques may be employed, in which solid precursor is volatilized, e.g., by sublimation of the solid starting material.

In lieu of using a deuterating agent as the pre-reaction-combating agent in the FIG. 20 system, one or more of the germanium, antimony and tellurium precursors could be supplied in the first instance as a deuterated analog of an organo germanium, antimony or tellurium precursor, in which hydrogen substituents of the organo moiety have been replaced with deuterium.

The pre-reaction-combating reagents may be employed in the broad practice of the present invention to produce improved films for the manufacture of semiconductor products. In general, the pre-reaction-combating reagents described herein may be utilized in various combinations in specific applications, to suppress or eliminate pre-reaction of the precursor and provide superior nucleation and final film properties.

While the invention has been has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

What is claimed is:

1. A method of forming a smooth, amorphous germanium-containing film on a substrate by a vapor deposition process, comprising volatilizing a germanium precursor to form a germanium precursor vapor, optionally combining the precursor vapor with a component selected from the group consisting of ammonia, hydrogen, helium, argon, and nitrogen, and contacting the precursor vapor with a substrate for vapor deposition of the germanium-containing film thereon, wherein the germanium precursor is of the formula

2. The method of claim 1, wherein the germanium-containing film further comprises tellurium, said method comprising volatilizing a tellurium precursor to form a tellurium precursor vapor, and contacting the tellurium precursor vapor with the substrate for vapor deposition of the film thereon.

3. The method of claim 2, wherein the tellurium precursor is selected from the group consisting of tellurium compositions of the formulae:

wherein:
$R_1$ and $R_2$ may be the same as or different from one another, and are independently selected from among H, $C_1$-$C_6$ alkyl, $C_5$-$C_{10}$ cycloalkyl, $C_6$-$C_{10}$ aryl, and —Si($R^3$)$_3$ wherein each $R^3$ is independently selected from $C_1$-$C_6$ alkyl;

wherein:
$R_1$, $R_2$ and $R_3$ may be the same as or different from one another, and are independently selected from among H, $C_1$-$C_6$ alkyl, $C_5$-$C_{10}$ cycloalkyl, $C_6$-$C_{10}$ aryl, and —Si($R_3$)$_3$ wherein each $R_3$ is independently selected from $C_1$-$C_6$ alkyl;

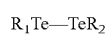

wherein:
R₁ and R₂ may be the same as or different from one another, and are independently selected, from among H, $C_1$-$C_6$ alkyl, $C_5$-$C_{10}$ cycloalkyl, $C_6$-$C_{10}$ aryl, and —Si($R^3$)₃ wherein each $R^3$ is independently selected from $C_1$-$C_6$ alkyl;
tellurium complexes with beta-diketiminate ligands,

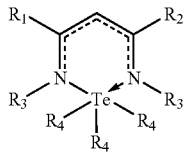

(I)

wherein R₁, R₂ and R₃ they be the same as or different from one another, and each is independently selected from $C_1$-$C_6$ alkyl, $C_6$-$C_{10}$ aryl, silyl and $C_1$-$C_{12}$ alkylamine (which includes both monoalkylamine as well as dialkylamine); and

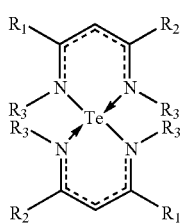

(II)

wherein R₁, R₂ and R₃ they be the same as or different from one another, and each is independently selected from $C_1$-$C_6$ alkyl, $C_6$-$C_{10}$ aryl, silyl and $C_1$-$C_{12}$ alkylamine (which includes both monoalkylamine as well as dialkylamine).

4. The method of claim 2, wherein the germanium- and tellurium-containing film further comprises antimony, said method comprising volatilizing an antimony precursor to form an antimony precursor vapor, and contacting the antimony precursor vapor with the substrate for vapor deposition of the film thereon.

5. The method of claim 4, wherein the antimony precursor is selected from the group consisting of antimony compositions of the formulae:

Sb(NR¹R²)(R³N(CR⁵R⁶)ₘNR⁴)

wherein:
R¹, R², R³, and R⁴ may be the same as or different from one another, and are independently selected from $C_1$-$C_6$ alkyl, $C_3$-$C_6$ cycloalkyl, $C_2$-$C_6$ alkenyl, $C_3$-$C_6$ alkylsilyl, $C_6$-$C_{10}$ aryl,
each of R⁵ and R⁶ may be the same as or different from one another and are independently selected from hydrogen, $C_1$-$C_6$ alkyl, $C_3$-$C_6$ cycloalkyl, $C_2$-$C_6$ alkenyl (e.g., vinyl, allyl, etc.), $C_3$-$C_6$ alkylsilyl, and $C_6$-$C_{10}$ aryl; and
m is an integer from 1 to 4 inclusive;

Sb(R₁)(R²N(CR⁴R⁵)ₘNR³)

wherein:
R¹, R², and R³ may be the same as or different from one another, and are independently selected from $C_1$-$C_6$ alkyl, $C_3$-$C_6$ cycloalkyl, $C_2$-$C_6$ alkenyl (e.g., vinyl, allyl, etc.), $C_3$-$C_6$ alkylsilyl, and $C_6$-$C_{10}$ aryl;
each of R⁴ and R⁵ may be the same as or different from one another and is independently selected from hydrogen, $C_1$-$C_6$ alkyl, $C_3$-$C_6$ cycloalkyl, $C_2$-$C_6$ alkenyl (e.g., vinyl, allyl, etc.), $C_3$-$C_6$ alkylsilyl, and $C_6$-$C_{30}$ aryl; and
m is an integer from 1 to 4 inclusive;

Sb(R¹)₃₋ₙ(NR²R³)ₙ wherein:
R¹, R² and R³ may be the same as or different from one another and are independently selected from hydrogen, $C_1$-$C_6$ alkyl, $C_3$-$C_6$ cycloalkyl, $C_2$-$C_6$ alkenyl (e.g., vinyl, allyl, etc.), silyl, $C_3$-$C_6$ alkylsilyl, $C_6$-$C_{10}$ aryl and —NR⁴R⁵, wherein each of R⁴ and R⁵ is selected from among H and $C_1$-$C_4$; and
n is an integer from 0 to 3 inclusive.

(R⁴)ₙSb(E(R¹R²R³))₃₋ₙ wherein:
R¹, R², R³, and R⁴ may be the same as or different from one another, and are independently selected from $C_1$-$C_6$ alkyl, $C_3$-$C_6$ cycloalkyl, $C_3$-$C_6$ alylsilyl, $C_6$-$C_{10}$ aryl, and alkylamino of the formula —NR⁵R⁶ wherein each of R⁵ and R⁶ is independently selected from H and $C_1$-$C_4$ alkyl;
E is silicon (Si) or germanium (Ge); and
n is an integer from 0 to 3 inclusive;
amimidates, guanidates and isoureates of the formula:

R⁷ₙSb[R¹NC(X) NR²]₃₋ₙ where each R¹ and R² is independently selected from among H, $C_1$-$C_6$ alkyl, $C_5$-$C_{10}$ cycloalkyl, $C_6$-$C_{10}$ aryl, and —Si($R^3$)₃ wherein each $R^3$ is independently selected from $C_1$-$C_6$ alkyl;
each X is independently selected from among $C_1$-$C_6$ alkoxy, —NR⁴R⁵, and —C(R⁶)₃, wherein each of R⁴, R⁵ and R⁶ is independently selected from H, $C_1$-$C_6$ alkyl, $C_5$-$C_{10}$ cycloalkyl, $C_6$-$C_{10}$ aryl, and —Si(R³)₃ wherein each R³ is independently selected from $C_1$-$C_6$ alkyl;
each R⁷ is independently selected from among $C_1$-$C_6$ alkoxy, —NR⁸R⁹, and —C(R¹⁰)₃, wherein each of R⁸, R⁹ and R¹¹) is independently selected from H, $C_1$-$C_6$ alkyl, $C_5$-$C_{10}$ cycloalkyl, $C_6$-$C_{10}$ aryl, —Si(R³)₃, and —Ge(R³)₃ wherein each R³ is independently selected from $C_1$-$C_6$ alkyl; and
n is an integer from 0 to 3;
tetra-alkyl guanidates of the formula:

R⁵ₙSb[(R¹R²)NC(NR³R⁴)N)]₃₋ₙ wherein:
each of R¹ and R² is independently selected from among H, $C_1$-$C_6$ alkyl, $C_5$-$C_{10}$ cycloalkyl, $C_6$-$C_{10}$ aryl, and —Si(R⁹)₃ wherein each R⁹ is independently selected from $C_1$-$C_6$ alkyl;
each of R³ and R⁴ is independently selected from H, $C_1$-$C_6$ alkyl, $C_5$-$C_{10}$ cycloalkyl, $C_6$"$C_{10}$ aryl, and —Si(R⁹)₃ wherein each R⁹ is independently selected from $C_1$-$C_6$ alkyl;
each R⁵ is independently selected from among $C_1$-$C_6$ alkoxy, —NR⁶R⁷, and —C(R⁸)₃, wherein each of R⁶, R⁷ and R⁸ is independently selected from H, $C_1$-$C_6$ alkyl, $C_5$-$C_{10}$ cycloalkyl, $C_6$-$C_{10}$ aryl, —Si(R⁹)₃, and —Ge(R⁹)₃ wherein each R⁹ is independently selected from $C_1$-$C_6$ alkyl; and
n is an integer from 0 to 3;
carbamates and thiocarbamates of the formula:

R⁴ₙSb[(EC(X)E]₃₋ₙ wherein:
- each X is independently selected from among $C_1$-$C_6$ alkoxy, —NR$^1$R$^2$, and —C(R$^3$)$_3$, wherein each of R$^1$, R$^2$ and R$^3$ is independently selected from H, $C_1$-$C_6$ alkyl, $C_5$-$C_{10}$ cycloalkyl, $C_6$-$C_{10}$ aryl, and —Si(R$^5$)$_3$ wherein each R$^5$ is independently selected from $C_1$-$C_6$ alkyl;
- each R$^4$ is independently selected from among $C_1$-$C_6$ alkoxy, —NR$^1$R$^2$, and —C(R$^3$)$_3$, wherein each of R$^1$, R$^2$ and R$^3$ is independently selected from H, $C_1$-$C_6$ alkyl, $C_5$-$C_{10}$ cycloalkyl, $C_6$-$C_{10}$ aryl, and —Si(R$^5$)$_3$, —Ge(R$^5$)$_3$ wherein each R$^5$ is independently selected from $C_1$-$C_6$ alkyl;
- E is either O or S; and
- n is an integer from 0 to 3;

beta-diketonates, diketoiminates, and diketiiminates, of the formulae:

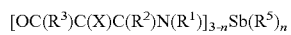

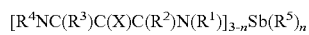

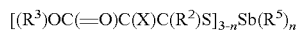

where each of R$^1$, R$^2$, R$^3$ and R$^4$ is independently selected from among H, $C_1$-$C_6$ alkyl, $C_5$-$C_{10}$ cycloalkyl, $C_6$-$C_{10}$ aryl, and —Si(R$^6$)$_3$ wherein each R$^6$ is independently selected from $C_1$-$C_6$ alkyl;

each X is independently selected from among $C_1$-$C_6$ alkoxy, —NR$^6$R$^7$, and —C(R$^8$)$_3$, wherein each of R$^6$, R$^7$ and R$^8$ is independently selected from H, $C_1$-$C_6$ alkyl, $C_5$-$C_{10}$ cycloalkyl, $C_6$-$C_{10}$ aryl, and —Si(R$^6$)$_3$ wherein each R$^6$ is independently selected from $C_1$-$C_6$ alkyl;

each R$^5$ is independently selected from among guanidinate, amimidate, isoureate, allyl, $C_1$-$C_6$ alkoxy, —NR$^9$R$^{10}$, and —C(R$^{11}$)$_3$, wherein each of R$^9$, R$^{10}$ and R$^{11}$ is independently selected from H, $C_1$-$C_6$ alkyl, $C_5$-$C_{10}$ cycloalkyl, $C_6$-$C_{10}$ aryl, —Si(R$^6$)$_3$, and —Ge(R$^6$)$_3$ wherein each R$^6$ is independently selected from $C_1$-$C_6$ alkyl; and n is an integer from 0 to 3.

allyls of the formulae:

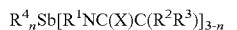

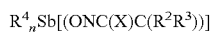

where each R$^1$, R$^2$, R$^3$ and R$^5$ is independently selected from among H, $C_1$-$C_6$ alkyl, $C_5$-$C_{10}$ cycloalkyl, $C_6$-$C_{10}$ aryl, and —Si(R$^6$)$_3$ wherein each R$^6$ is independently selected from $C_1$-$C_6$ alkyl;

each X is independently selected from among $C_1$-$C_6$ alkoxy, —NR$^1$R$^2$, and —C(R$^3$)$_3$, wherein each of R$^1$, R$^2$ and R$^3$ is independently selected from H, $C_1$-$C_6$ alkyl, $C_5$-$C_{10}$ cycloalkyl, $C_6$-$C_{10}$ aryl, and —Si(R$^6$)$_3$ wherein each R$^6$ is independently selected from $C_1$-$C_6$ alkyl;

each R$^4$ is independently selected from among guanidinates, amimidates, isoureates, beta-diketonates, diketoiminates, diketiiminates, $C_1$-$C_6$ alkoxy, —NR$^7$R$^8$, and —C(R$^9$)$_3$, wherein each of R$^7$, R$^8$ and R$^9$ is independently selected from H, $C_1$-$C_6$ alkyl, $C_5$-$C_{10}$ cycloalkyl, $C_6$-$C_{10}$ aryl, —Si(R$^6$)$_3$, and —Ge(R$^6$)$_3$ wherein each R$^6$ is independently selected from $C_1$-$C_6$ alkyl; and n is an integer from 0 to 3;

cyclopentadienyl (Cp) antimony compounds wherein the Cp moiety is of the formulae:

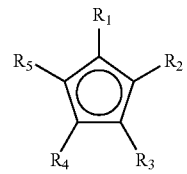

wherein each of R$_1$, R$_2$, R$_3$, R$_4$ and R$_5$ can be the same as or different from the others, and each is independently selected from among hydrogen, $C_1$-$C_{12}$ alkyl, $C_1$-$C_{12}$ alkylamino, $C_6$-$C_{10}$ aryl, $C_1$-$C_{12}$ alkoxy, $C_3$-$C_6$ alkylsilyl, $C_2$-$C_{12}$ alkenyl, R$^1$R$^2$NNR$^3$, wherein R$^1$, R$^2$ and R$^3$ may be the same as or different from one another and each is independently selected from $C_1$-$C_6$ alkyl, and pendant ligands including functional group(s) providing further coordination to the antimony central atom, and selected from among aminoalkyl, alkoxyalkyl, aryloxyalkyl, imidoalkyl, and acetylalkyl, having the following formulae:

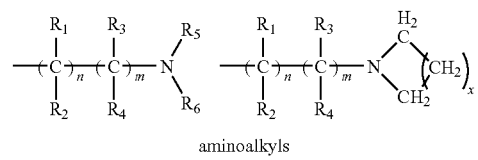

aminoalkyls wherein: the methylene (—CH$_2$—) moiety could alternatively be another divalent hydrocarbyl moiety; each of R$_1$-R$_4$ is the same as or different from one another, with each being independently selected from among hydrogen, $C_1$-$C_6$ alkyl and $C_6$-$C_{10}$ aryl; each of R$_5$ and R$_6$ is the same as or different from the other, with each being independently selected from among $C_1$-$C_6$ alkyl; n and m are each selected independently as having a value of from 0 to 4, with the proviso that m and n cannot be 0 at the same time, and x is selected from 1 to 5;

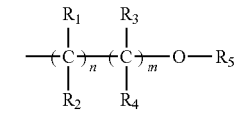

alkoxyalkyls and aryloxyalkyls wherein each of R$_1$-R$_4$ is the same as or different from one another, with each being independently selected from among hydrogen, $C_1$-$C_6$ alkyl, and $C_6$-$C_{10}$ aryl; R$_5$ is selected from among $C_1$-$C_6$ alkyl, and $C_6$-$C_{10}$ aryl; and n and m are selected independently as having a value of from 0 to 4, with the proviso that m and n cannot be 0 at the same time;

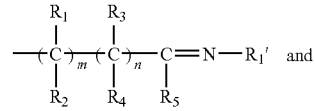

and

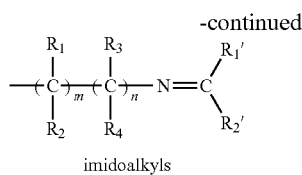

imidoalkyls wherein each of $R_1$, $R_2$, $R_3$, $R_4$, $R_5$ is the same as or different from one another, with each being independently selected from among hydrogen, $C_1$-$C_6$ alkyl, and $C_6$-$C_{10}$ aryl; each of $R_1'$, $R_2'$ is the same as or different from one another, with each being independently selected from $C_1$-$C_6$ alkyl, and $C_6$-$C_{10}$ aryl; and n and m are selected independently from 0 to 4, with the proviso that m and n cannot be 0 at the same time;

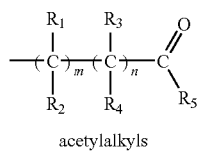

acetylalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, $C_6$-$C_{10}$ aryl, and $C_1$-$C_5$ alkoxy; and n and m are selected independently from 0 to 4, with the proviso that m and n cannot be 0 at the same time;

wherein non-Cp ligand(s) of the antimony Cp compound can optionally include ligands selected from the group consisting of guanidinates, amimidates, isoureates, allyls, beta-diketonates, diketoiminates, and diketiiminates; and (M) alkyls, alkoxides and silyls with pendent ligands, of the formulae:

 (i)

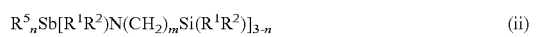 (ii)

 (iii)

where each of $R^1$ and $R^2$ is independently selected from among H, $C_1$-$C_6$ alkyl, $C_5$-$C_{10}$ cycloalkyl, $C_6$-$C_{10}$ aryl, and —Si($R^3$)$_3$ wherein each $R^3$ is independently selected from $C_1$-$C_6$ alkyl;

each $R^5$ is independently selected from among guanidinates, amimidates, isoureates, beta-diketonates, diketoiminates, diketiiminates, $C_1$-$C_6$ alkoxy, —NR$^6$R$^7$, and —C($R^8$)$_3$, wherein each of $R^6$, $R^7$ and $R^8$ is independently selected from H, $C_1$-$C_6$ alkyl, $C_5$-$C_{10}$ cycloalkyl, $C_6$-$C_{10}$ aryl, —Si($R^3$)$_3$, and —Ge($R^3$)$_3$ wherein each $R^3$ is independently selected from $C_1$-$C_6$ alkyl;

n is an integer from 0 to 3;

m is integer from 0 to 4.

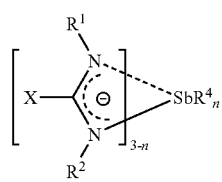 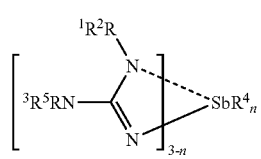

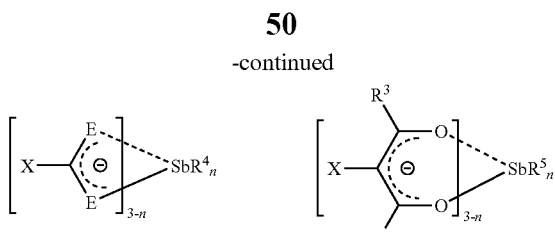

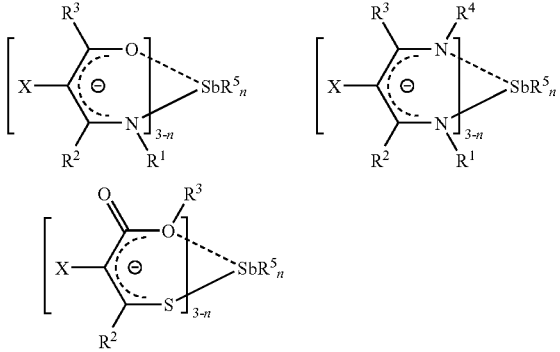

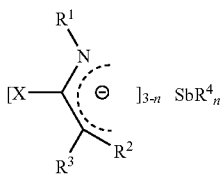

A

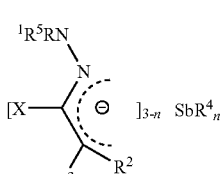

B

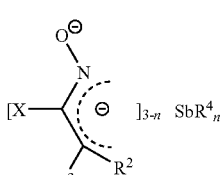

C

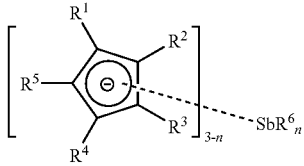

D

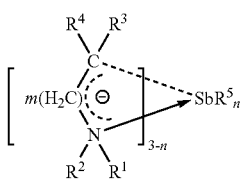

A

-continued

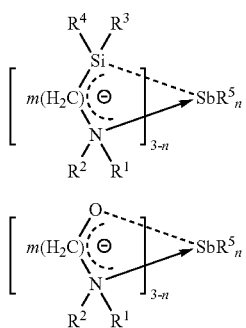

antimony amides of the formulae

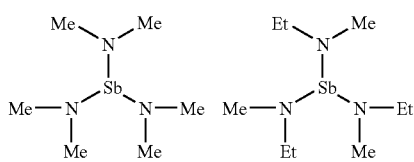

antimony (III) alkyl/amino precursors of the formulae:

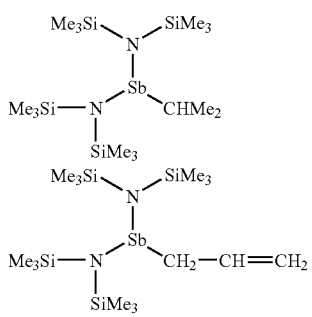

and stibenes with germanium anions, of the formulae:

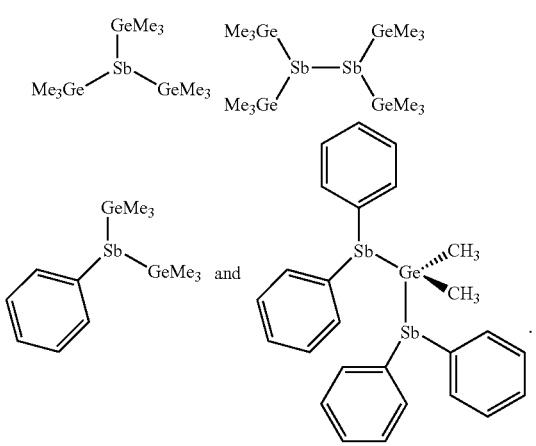

6. The method of claim 1, comprising combining the precursor vapor with a component selected from the group consisting of ammonia, hydrogen, helium, argon, and nitrogen.

7. The method of claim 1, wherein the substrate is also contacted with precursor vapor of an antimony precursor and with precursor vapor of a tellurium precursor, so that the germanium-containing film comprises a GeSbTe film, and wherein the method is carried out so as to combat precursor pre-reaction of at least one of said germanium, antimony and tellurium precursors.

8. The method of claim 1, wherein the film is a smooth, amorphous GeTe or a GeSbTe film.

9. The method of claim 2, wherein the tellurium precursor comprises a dialkyl tellurium compound selected from among di-tert-butyl tellurium and diisopropyl tellurium.

10. The method of claim 1, wherein said film is deposited in a fill trench or via structure on the substrate.

11. The method of claim 1, comprising forming a phase change random access memory device including a germanium- and tellurium-containing film of smooth, amorphous character.

12. The method of claim 1, comprising combating pre-reaction of precursor by introducing to said process a pre-reaction-combating agent selected from the group consisting of (i) (O, N, S) organo Lewis base compounds, (ii) free radical inhibitors, and (iii) deuterium-containing reagents.

13. The method of claim 1, for forming a smooth amorphous germanium telluride film, comprising volatilizing the germanium precursor and a diakyl tellurium precursor to form the precursor vapor and contacting the precursor vapor with the substrate to form the smooth amorphous germanium telluride film on the substrate.

14. The method of claim 1, for forming a phase change random access memory device, comprising forming a germanium telluride film of smooth, amorphous character, including vapor deposition of germanium from said germanium precursor, wherein said vapor deposition comprises use of a dialkyl tellurium precursor, and is carried out with a co-reactant comprising ammonia.

15. The method of claim 14, wherein said dialkyl tellurium precursor is selected from the group consisting of di-tert-butyl tellurium and diisopropyl tellurium.

16. The method of claim 1, wherein said germanium precursor is contacted with said substrate in manufacturing a phase change random access memory device.

17. The method of claim 16, comprising contacting the substrate with vapor of an antimony precursor comprising a trialkyl or triamido antimony compound.

18. The method of claim 17, wherein the trialkyl or triamido antimony compound comprises tris(dimethylamino)antimony.

19. The method of claim 16, further comprising the use of a pre-reaction-combating agent selected from the group consisting of (i) (O, N, S) organo Lewis base compounds, (ii) free radical inhibitors, and (iii) deuterium-containing reagents.

20. The method of claim 16, wherein said germanium precursor is contacted with said substrate at temperature not exceeding 350° C.

* * * * *

UNITED STATES PATENT AND TRADEMARK OFFICE
CERTIFICATE OF CORRECTION

| | | |
|---|---|---|
| PATENT NO. | : 8,093,140 B2 | Page 1 of 1 |
| APPLICATION NO. | : 12/263403 | |
| DATED | : January 10, 2012 | |
| INVENTOR(S) | : Philip S. H. Chen | |

It is certified that error appears in the above-identified patent and that said Letters Patent is hereby corrected as shown below:

Column 44, line 64: "...$(R_3)_3$ wherein each $R_3$..." should be -- ...$(R^3)_3$ wherein each $R^3$... --.

Column 45, line 2: "...independently selected, from..." should be -- independently selected from --.

Column 45, line 18: "...wherein $R_1$, $R_2$ and $R_3$, they be..." should be -- ...wherein $R_1$, $R_2$ and $R_3$ may be... --.

Column 45, line 35: "...wherein $R_1$, $R_2$ and $R_3$, they be..." should be -- ...wherein $R_1$, $R_2$ and $R_3$ may be... --.

Column 46, line 4: "...and $C_8$-$C_{30}$ aryl..." should be -- ...and $C_8$-$C_{10}$ aryl... --.

Column 46, line 42: "...$R^8$, $R^9$ and $R^{11}$..." should be -- ...$R^8$, $R^9$ and $R^{10}$... --.

Column 46, line 56: "...$C_8$"$C_{10}$ aryl..." should be -- ...and $C_8$-$C_{10}$ aryl... --.

Column 52, line 30: "...and a diakyl tellurium precursor..." should be -- ... and a dialkyl tellurium precursor... --.

Signed and Sealed this
Fourth Day of September, 2012

David J. Kappos
*Director of the United States Patent and Trademark Office*